United States Patent
Modak et al.

(10) Patent No.: US 9,687,429 B2
(45) Date of Patent: Jun. 27, 2017

(54) ANTIMICROBIAL COMPOSITIONS CONTAINING LOW CONCENTRATIONS OF BOTANICALS

(75) Inventors: Shanta Modak, River Edge, NJ (US); Nayana Baiju, New York, NY (US); Lauserpina Caraos, Hollis, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 12/694,119

(22) Filed: Jan. 26, 2010

(65) Prior Publication Data
US 2010/0172847 A1    Jul. 8, 2010

Related U.S. Application Data

(63) Continuation-in-part of application No. 12/367,851, filed on Feb. 9, 2009, now abandoned, which is a continuation-in-part of application No. PCT/US2008/072006, filed on Aug. 1, 2008, which is a continuation-in-part of application No. 12/134,918, filed on Jun. 6, 2008, and a continuation-in-part of application No. 12/016,788, filed on Jan. 18, 2008, now abandoned, said application No. PCT/US2008/072006 is a continuation-in-part of application No. 12/016,788, filed on Jan. 18, 2008, now abandoned.

(60) Provisional application No. 60/945,288, filed on Jun. 20, 2007, provisional application No. 60/953,654, filed on Aug. 2, 2007.

(51) Int. Cl.
| | |
|---|---|
| *A61K 8/97* | (2006.01) |
| *A61K 8/365* | (2006.01) |
| *A61K 8/92* | (2006.01) |
| *A61K 31/19* | (2006.01) |
| *A61Q 5/02* | (2006.01) |
| *A61Q 11/02* | (2006.01) |
| *A61Q 15/00* | (2006.01) |
| *A61Q 17/00* | (2006.01) |
| *A61Q 19/10* | (2006.01) |

(52) U.S. Cl.
CPC .............. *A61K 8/365* (2013.01); *A61K 8/922* (2013.01); *A61K 31/19* (2013.01); *A61Q 5/02* (2013.01); *A61Q 11/02* (2013.01); *A61Q 15/00* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 4,022,605 A | 5/1977 | Konya et al. |
| 4,049,802 A | 9/1977 | Fox, Jr. |
| 4,330,531 A | 5/1982 | Alliger |
| 4,404,197 A | 9/1983 | Fox, Jr. et al. |
| 4,563,485 A | 1/1986 | Fox, Jr. et al. |
| 4,579,731 A | 4/1986 | Fox, Jr. et al. |
| 4,581,028 A | 4/1986 | Fox, Jr. et al. |
| 4,612,337 A | 9/1986 | Fox, Jr. et al. |
| 4,723,950 A | 2/1988 | Lee |
| 4,859,359 A | 8/1989 | DeMatteo et al. |
| 4,867,898 A | 9/1989 | Spaulding et al. |
| 4,956,354 A | 9/1990 | Gutierrez |
| 4,975,217 A | 12/1990 | Brown-Skrobot et al. |
| 5,019,096 A | 5/1991 | Fox, Jr. et al. |
| 5,033,488 A | 7/1991 | Curtis et al. |
| 5,073,366 A | 12/1991 | Beck |
| 5,091,442 A | 2/1992 | Milner |
| 5,100,652 A | 3/1992 | Kross et al. |
| 5,135,747 A | 8/1992 | Faryniarz et al. |
| 5,180,605 A | 1/1993 | Milner |
| 5,200,194 A | 4/1993 | Edgren et al. |
| 5,209,251 A | 5/1993 | Curtis et al. |
| 5,261,421 A | 11/1993 | Milner |
| 5,310,546 A | 5/1994 | Douglas |
| 5,334,588 A | 8/1994 | Fox, Jr. et al. |
| 5,567,495 A | 10/1996 | Modak et al. |
| 5,614,538 A | 3/1997 | Nelson, Jr. |
| 5,616,338 A | 4/1997 | Fox, Jr. et al. |
| 5,772,640 A | 6/1998 | Modak et al. |
| 5,854,266 A | 12/1998 | Nelson, Jr. |
| 5,866,527 A | 2/1999 | Mertens |

(Continued)

FOREIGN PATENT DOCUMENTS

| | | |
|---|---|---|
| CH | 654327 | 2/1986 |
| DE | 202008002718 U1 | 7/2009 |

(Continued)

OTHER PUBLICATIONS

Skin Care, Retrieved from URL:<https://web.archive.org/web/20050119140921/http://www.morganics.com/store/page8.html>, Jan. 19, 2005.*
U.S. Appl. No. 12/016,788, filed Jan. 18, 2008.
U.S. Appl. No. 12/134,918, filed Jun. 6, 2008.
U.S. Appl. No. 12/367,851, Feb. 9, 2009.
U.S. Appl. No. 12/694,141, filed Jan. 26, 2010.
U.S. Appl. No. 12/136,530, filed Jun. 10, 2008.
U.S. Appl. No. 12/134,911, filed Jun. 6, 2008.
U.S. Appl. No. 12/136,530, Jun. 16, 2010 Non-Final Office Action.
U.S. Appl. No. 12/136,530, Jun. 2, 2010 RCE and Response to Final Office Action.
U.S. Appl. No. 12/136,530, Mar. 2, 2010 Final Office Action.
U.S. Appl. No. 12/136,530, Dec. 11, 2009 Response to Non-Final Office Action.

(Continued)

*Primary Examiner* — Nannette Holloman
(74) *Attorney, Agent, or Firm* — Tarter Krinsky & Drogin LLP

(57) ABSTRACT

The present invention relates to a preservative or antimicrobial compositions with broad spectrum antimicrobial activity comprising low concentrations of essential oil (and/or one or more component thereof) and a botanical extract in synergistic combination with a fruit acid and alkanediol, and optionally a solvent. The compositions of the invention may be used in personal care products such as creams or soap products.

15 Claims, No Drawings

(56) References Cited

U.S. PATENT DOCUMENTS

| | | |
|---|---|---|
| 5,891,422 A | 4/1999 | Pan et al. |
| 5,968,539 A | 10/1999 | Beerse et al. |
| 5,985,819 A | 11/1999 | Lu et al. |
| 5,985,918 A | 11/1999 | Modak et al. |
| 6,075,056 A | 6/2000 | Quigley, Jr. et al. |
| 6,083,208 A | 7/2000 | Modak et al. |
| 6,106,505 A | 8/2000 | Modak et al. |
| 6,120,758 A | 9/2000 | Siddiqui et al. |
| 6,258,368 B1 | 7/2001 | Beerse et al. |
| 6,270,811 B1 | 8/2001 | Fregonese |
| 6,280,758 B1 | 8/2001 | Warren et al. |
| 6,287,583 B1 | 9/2001 | Warren et al. |
| 6,312,675 B1 | 11/2001 | Deane |
| 6,319,958 B1 | 11/2001 | Johnson et al. |
| 6,323,166 B1 | 11/2001 | Kamiya |
| 6,348,501 B1 | 2/2002 | Holt et al. |
| 6,397,224 B1 | 5/2002 | Zubeldia et al. |
| 6,420,326 B1 | 7/2002 | Maile et al. |
| 6,451,748 B1 | 9/2002 | Taylor et al. |
| 6,537,955 B1 | 3/2003 | Raso et al. |
| 6,582,719 B2 | 6/2003 | Modak et al. |
| 6,616,922 B2 | 9/2003 | Taylor et al. |
| 6,630,163 B1 * | 10/2003 | Murad .................. 424/464 |
| 6,632,784 B2 | 10/2003 | Massaux et al. |
| 6,635,676 B2 | 10/2003 | Baker, Jr. et al. |
| 6,696,399 B1 | 2/2004 | Chernin et al. |
| 6,699,825 B2 | 3/2004 | Rees et al. |
| 6,716,883 B1 | 4/2004 | Casper et al. |
| 6,753,305 B2 | 6/2004 | Raso |
| 6,858,317 B2 | 2/2005 | Aamodt et al. |
| 6,921,745 B2 | 7/2005 | Yamada et al. |
| 6,951,833 B2 | 10/2005 | O'Neil |
| 6,969,522 B2 | 11/2005 | Bessette et al. |
| 6,974,584 B2 | 12/2005 | Bessette |
| 7,435,429 B2 | 10/2008 | Modak et al. |
| 7,563,461 B2 | 7/2009 | Modak et al. |
| 7,563,462 B2 | 7/2009 | Newmark et al. |
| 7,572,469 B2 | 8/2009 | Santo et al. |
| 7,985,773 B2 | 7/2011 | Greten et al. |
| 2001/0010016 A1 | 7/2001 | Modak et al. |
| 2001/0024661 A1 | 9/2001 | Modak et al. |
| 2002/0122876 A1 | 9/2002 | Modak et al. |
| 2002/0165130 A1 | 11/2002 | Johnson et al. |
| 2002/0173775 A1 | 11/2002 | Modak et al. |
| 2002/0192256 A1 | 12/2002 | Wu et al. |
| 2003/0113388 A1 | 6/2003 | Phan |
| 2003/0168077 A1 | 9/2003 | Brown et al. |
| 2003/0180233 A1 | 9/2003 | Anderson et al. |
| 2003/0195263 A1 | 10/2003 | Schmaus et al. |
| 2003/0213168 A1 | 11/2003 | Hesse et al. |
| 2004/0092482 A1 | 5/2004 | Gupta |
| 2004/0102429 A1 | 5/2004 | Modak et al. |
| 2004/0132667 A1 | 7/2004 | Lintner |
| 2004/0192551 A1 | 9/2004 | Bessette et al. |
| 2004/0247685 A1 | 12/2004 | Modak et al. |
| 2004/0253275 A1 | 12/2004 | Eini et al. |
| 2005/0019431 A1 | 1/2005 | Modak et al. |
| 2005/0026802 A1 | 2/2005 | Kilkenny et al. |
| 2005/0048139 A1 | 3/2005 | Modak et al. |
| 2005/0063939 A1 | 3/2005 | Ameer |
| 2005/0187124 A1 | 8/2005 | Li et al. |
| 2005/0222276 A1 | 10/2005 | Schmaus et al. |
| 2005/0238602 A1 | 10/2005 | Modak et al. |
| 2006/0018867 A1 | 1/2006 | Kawasaki et al. |
| 2006/0051384 A1 | 3/2006 | Scholz et al. |
| 2006/0099237 A1 | 5/2006 | Modak et al. |
| 2006/0198800 A1 | 9/2006 | Dilallo et al. |
| 2006/0216246 A1 | 9/2006 | Belanger et al. |
| 2006/0233901 A1 | 10/2006 | Jamieson et al. |
| 2006/0293201 A1 | 12/2006 | Simon et al. |
| 2006/0293214 A1 | 12/2006 | Cheng et al. |
| 2007/0003538 A1 | 1/2007 | Madhyastha |
| 2007/0014823 A1 | 1/2007 | Iwata |
| 2007/0020342 A1 | 1/2007 | Modak et al. |
| 2007/0027119 A1 | 2/2007 | Ahmed et al. |
| 2007/0190094 A1 | 8/2007 | Bessette et al. |
| 2007/0275070 A1 | 11/2007 | Ahmed et al. |
| 2007/0286813 A1 | 12/2007 | Toutounghi |
| 2008/0008729 A1 | 1/2008 | Swaine et al. |
| 2008/0038219 A1 * | 2/2008 | Mosbaugh et al. .............. 424/74 |
| 2008/0063607 A1 | 3/2008 | Tamarkin et al. |
| 2008/0166314 A1 | 7/2008 | Jochim et al. |
| 2008/0226568 A1 | 9/2008 | Rozsa et al. |
| 2008/0234173 A1 | 9/2008 | Warr et al. |
| 2008/0253976 A1 | 10/2008 | Scott et al. |
| 2008/0260708 A1 | 10/2008 | Hall |
| 2008/0299220 A1 | 12/2008 | Tamarkin et al. |
| 2008/0317737 A1 | 12/2008 | Patel et al. |
| 2008/0318784 A1 | 12/2008 | Koo et al. |
| 2009/0004122 A1 | 1/2009 | Modak et al. |
| 2009/0028751 A1 | 1/2009 | Robbins |
| 2009/0029961 A1 | 1/2009 | Modak et al. |
| 2009/0035228 A1 | 2/2009 | Modak et al. |
| 2009/0068255 A1 | 3/2009 | Yu et al. |
| 2009/0088358 A1 * | 4/2009 | Roso et al. ................... 510/130 |
| 2009/0165812 A1 | 7/2009 | Resnick et al. |
| 2009/0175806 A1 | 7/2009 | Modak et al. |
| 2009/0191288 A1 | 7/2009 | Squires et al. |
| 2009/0300864 A1 | 12/2009 | Adkins et al. |
| 2010/0034871 A1 | 2/2010 | Mikkelsen et al. |
| 2010/0140368 A1 | 6/2010 | De Lame et al. |
| 2010/0172847 A1 | 7/2010 | Modak et al. |
| 2010/0172848 A1 | 7/2010 | Modak et al. |
| 2010/0183524 A1 | 7/2010 | Zielinski et al. |
| 2010/0196494 A1 | 8/2010 | Van Beek |
| 2010/0216889 A1 | 8/2010 | Modak et al. |
| 2010/0234460 A1 | 9/2010 | Foret et al. |
| 2010/0248962 A1 | 9/2010 | Wilczynski et al. |
| 2010/0317743 A1 | 12/2010 | Macinga et al. |
| 2010/0323043 A1 | 12/2010 | Perla et al. |
| 2011/0028563 A1 | 2/2011 | Found |
| 2011/0070316 A1 | 3/2011 | Modak et al. |
| 2011/0070376 A1 | 3/2011 | Wales et al. |
| 2011/0142899 A1 | 6/2011 | Lagaron Abello et al. |
| 2012/0100231 A1 | 4/2012 | Perla et al. |
| 2012/0129950 A1 | 5/2012 | Macinga et al. |
| 2012/0171156 A1 | 7/2012 | Basketter et al. |
| 2012/0201902 A1 | 8/2012 | Modak et al. |
| 2012/0207862 A1 | 8/2012 | Morre et al. |
| 2013/0230609 A1 | 9/2013 | Modak et al. |
| 2014/0079819 A1 | 3/2014 | Debaun et al. |
| 2014/0178447 A1 | 6/2014 | Modak et al. |
| 2014/0242198 A1 | 8/2014 | Modak et al. |
| 2014/0243417 A1 | 8/2014 | Modak et al. |
| 2014/0322147 A1 | 10/2014 | Modak et al. |
| 2015/0118275 A1 | 4/2015 | Modak et al. |
| 2015/0265666 A1 | 9/2015 | Modak et al. |

FOREIGN PATENT DOCUMENTS

| | | | |
|---|---|---|---|
| EP | 0 054 205 | 6/1982 | |
| EP | 0 106 266 | 4/1984 | |
| EP | 1108419 | 6/2001 | |
| EP | 1 146 112 | 10/2001 | |
| EP | 1206933 * | 5/2002 | ............... A61K 7/48 |
| EP | 1 288 285 | 3/2003 | |
| FR | 2771632 | 6/1999 | |
| FR | 2874928 | 3/2010 | |
| GB | 1 060 447 | 3/1967 | |
| JP | 1997-323910 | 12/1997 | |
| JP | 2002-193717 | 7/2002 | |
| JP | 2002370958 | 12/2002 | |
| JP | 2004-217615 | 8/2004 | |
| JP | 04250331 | 9/2004 | |
| JP | 2004277554 | 10/2004 | |
| JP | 2004-322078 | 11/2004 | |
| JP | 2006-225289 | 8/2006 | |
| JP | 2007-291049 | 11/2007 | |
| JP | 2010-083806 | 4/2010 | |
| JP | 2010-184987 | 8/2010 | |
| KR | 10-2004-077206 | 9/2004 | |
| SU | 513676 | 5/1976 | |
| WO | WO 84/04556 | 11/1984 | |
| WO | WO 85/01208 | 3/1985 | |

(56) References Cited

FOREIGN PATENT DOCUMENTS

| WO | WO 89/06962 | 8/1989 |
|---|---|---|
| WO | WO 92/04029 | 3/1992 |
| WO | WO 93/02717 | 2/1993 |
| WO | WO 98/51273 | 11/1998 |
| WO | WO 99/22718 | 5/1999 |
| WO | WO 00/65011 | 11/2000 |
| WO | WO 01/72262 | 10/2001 |
| WO | WO 01/91555 | 12/2001 |
| WO | WO 02/22060 | 3/2002 |
| WO | WO/03/000303 | 1/2003 |
| WO | WO 03/018498 | 3/2003 |
| WO | WO 03/018743 | 3/2003 |
| WO | WO 03/077856 | 9/2003 |
| WO | WO 03/078367 | 9/2003 |
| WO | WO 2004/004631 | 1/2004 |
| WO | WO 2004014416 | 2/2004 |
| WO | WO/2006/010269 | 2/2006 |
| WO | WO 2006/023349 | 3/2006 |
| WO | WO 2006099359 | 9/2006 |
| WO | WO 2007/069214 | 6/2007 |
| WO | WO 2007/071089 | 6/2007 |
| WO | WO 2007/077573 | 7/2007 |
| WO | WO 2007/095041 | 8/2007 |
| WO | WO 2007/101848 | 9/2007 |
| WO | WO 2007/123790 | 11/2007 |
| WO | WO 2007/126651 | 11/2007 |
| WO | WO 2008/031087 | 3/2008 |
| WO | WO 2008/042197 | 4/2008 |
| WO | WO 2008/061187 | 5/2008 |
| WO | WO 2008/119841 | 10/2008 |
| WO | WO 2008/154395 | 12/2008 |
| WO | WO 2008/157847 | 12/2008 |
| WO | WO 2009/062746 | 3/2009 |
| WO | WO 2009/049208 | 4/2009 |
| WO | 2010091415 A1 | 8/2010 |
| WO | WO 2010/091415 | 8/2010 |
| WO | WO 2010/119369 | 10/2010 |
| WO | WO 2011/002929 | 1/2011 |
| WO | 2011002929 A1 | 6/2011 |
| WO | WO 2011/151835 | 12/2011 |
| WO | WO 2012/017349 | 2/2012 |
| WO | WO 2012/051204 | 4/2012 |
| WO | 2013066403 A1 | 5/2013 |
| WO | 2013103556 A1 | 7/2013 |
| WO | WO 2014/092999 | 6/2014 |

OTHER PUBLICATIONS

U.S. Appl. No. 12/136,530, Sep. 22, 2009 Non-Final Office Action.
Baiju et al., 2008, "Development of a Novel Surface Disinfectant Composition Containing Essential Oils and Fruit Acid Against Nosocomial Pathogens Commonly Associated with Environmental Surfaces," *International Journal of Essential Oil Therapeutics*, vol. 2; p. 9-14.
Bezic et al.; 2003; "Composition and antimicrobial activity of *Achillea clavennae* L. essential oil." Phytother. Res. 17(9):1037-1040.
Bion, 2008; "Acne Treatment Products" http://www.bion-research.com/acne_treatment_products.htm.
Bion, 2008; "Moderate to Severe Acne" http://www.bion-research.com/moderate_to_severe_acne.htm.
Brehm-Stecher et al.; 2003; "Sensitization of *Staphylococcus aureus* and *Escherichia coli* to antibiotics by the sesquiterpenoids nerolidol, farnesol, bisabolol, and apritone."Antimicrobial Agents and Chemotherapy; 47(10):3357-3360.
de Abreu Gonzaga et al.; 2003; "Composition and antibacterial activity of the essential oils from Zanthoxylum rhoifolium." Planta Med. 69(8):773-775.
Garcia et al.; 2003; "Virucidal activity of essential oils from aromatic plants of San Luis, Argentina." Phytother. Res. 17(9):1073-1075.
Gershon, et al., 2006, "Antifungal Properties of n-Alkanols, α, w-n-Alkanedoils, and w-Chloro-α-alkanols," *J. Pharm. Sci.*, vol. 64, No. 4: p. 381-384.
Goren et al.; 2003; "Analysis of essential oil of *Coridothymus capitatus* (L.) and its antibacterial and antifungal activity." Z. Naturforsch. 58(9-10):687-690.
Hajhashemi et al.; 2003; "Anti-inflammatory and analgesic properties of the leaf extracts and essential oil of Lavandula angustifolia Mill." J. Ethnopharmacol. 89(1):67-71.
Kupferwasser, et al., 1999, "Acetylsalicylic Acid Reduces Vegetation Bacterial Density, Hernatogenous Bacterial Dissemination, and Frequency of Embolic Events in Experimental *Staphylococcus aureus* Endocarditis Through Antiplatelet and Antibacterial Effects," *Circulation*, vol. 99: p. 2791-2797.
Kupferwasser, et al., 2003, "Salicylic Acid Attenuates Virulence in Endovascular Infections by Targeting Global Regulatory Pathways in *Staphylococcus aureus*," *Clin. Invest.*, vol. 112, No. 2: p. 222-233.
Minami et al.; 2003; "The inhibitory effect of essential oils on herpes simplex virus type-1 replication in vitro." Microbial Immunol. 47(a):681-684.
Paranagama et al.; 2003; "Fungicidal and anti-aflatoxigenic effects of the essential oil of *Cymbopogon citrates* (DC.) Stapf. (lemongrass) against Aspergillus flavus Link. isolated from stored rice." Lett. Appl. Microbiol.; 37(1):86-90.
Pommier, et al, "Phase III Randomized Trial of Calendula Officinalis Compared With Trolamine for the Prevention of Acute Dermatitis During Irradiation for Breast Cancer," J Clin Oncol:1447-1453, Apr. 15, 2004, p. 1447, Results, Conclusion.
Schuhmacher et al.; 2003; "Virucidal effect of peppermint oil on the enveloped viruses herpes simplex virus type 1 and type 2 in vitro." Phytomedicine 10:504-510.
Shin; 2003; "Anti-Aspergillus activities of plant essential oils and their combination effects with ketoconazole or amphotericin B."Arch. Pharm. Res. 26(5):389-393.
Silva et al.; 2003; "Analgesic and anti-inflammatory effects of essential oils of Eucalyptus." J. Ethnopharmacol. 89(2-3);277-283.
Valero and Salmera; 2003; "Antibacterial activity of 11 essential oils against Bacillus cereus in tyndallized carrot broth." Int. J. Food Microbiol. 85(1-2):73-81.
Velluti et al.; 2003; "Inhibitory effect of cinnamon, clove, lemongrass, oregano and palmarose essential oils on growth and fumonisin B1 production by Fusarium proliferatum in maize grain." Int. J. Food Microbiol.; 89:145-154.
Mohammad Najmul Ghani Khan; Khazaain-al-Advia, vol. II (20th century AD), Nadeem Yunus Printer/Sheikh Mohd Basheer & Sons, Lahore, 1911 AD p. 656.
Mohammad Najmul Ghani Khan; Qaraabaadeen Najm-al-Ghani (20th century AD), Munshi Nawal Kishore, Lucknow, (Second Edition) 1928 AD p. 566.
Mohammad Azam Khan; Muheet Azam vol. II (Part II) (19th century AD), Matba Nizami, Kanpur, 1898 AD p. 3.
Susruta; Susruta Samhita—Edited & translated by P.V. Sharma, vol. III: Chaukhamba Visvabharati, Varanasi, Edn. Ist, 2001. [Time of origin 1000 BC—5th century] p. 10.
Mohammad Shareef Khan; Ilaaj-al-Amraaz (18th centruy AD), Afzal-al-Matabe, Barqi Press, Delhi, 1921 AD p. 357.
Siddhayogasamgrahah—Compiled by Yadavji Trikamji Acharya, Sri Baidyanath Ayurved Bhawan, Allahabad, Edn. 1st 1978 pp. 131-132.
Mohammad Najmul Ghani Khan; Khazaain-al-Advia, vol. III (20th century AD), Nadeem Yunus Printer/Sheikh Mohd Basheer & Sons, Lahore, 1926 AD p. 568.
Sarngadharacarya; Saringadhara Samhita—Translated by Smt. Shailaja Srivastava: Chaukhamba Orientalia, Varansai, Edn. 2nd, 1998. [Time of origin 13th century] pp. 431-432.
Ziya Al-Din Abdullah Ibn Al-Baitar; Al-Jaam'e-li-Mufradaat-al-Advia-wal-Aghzia, vol. IV (13th century AD), Matba Amra, Cario, Egypt, 1874 AD p. 57.
U.S. Appl. No. 13/335,363, filed Dec. 22, 2011.
U.S. Appl. No. 12/134,911, May 2, 2012 Amendment and Request for Continued Examination (RCE).
U.S. Appl. No. 12/016,788, Apr. 24, 2012 Response to Non-Final Office Action.
U.S. Appl. No. 12/134,918, Mar. 28, 2012 Response to Non-Final Office Action.

(56) References Cited

OTHER PUBLICATIONS

U.S. Appl. No. 12/694,141, Mar. 28, 2012 Response to Non-Final Office Action.
U.S. Appl. No. 12/134,918, Nov. 15, 2011 Non-Final Office Action.
U.S. Appl. No. 12/134,911, Dec. 2, 2011 Final Office Action.
U.S. Appl. No. 12/134,911, Aug. 18, 2011 Reponse to Non-Final Office Action.
U.S. Appl. No. 12/134,911, Feb. 18, 2011 Non-Final Office Action.
U.S. Appl. No. 12/136,530, Jun. 29, 2011 Non-Final Office Action.
U.S. Appl. No. 12/136,530, May 19, 2011 Amendment and Request for Continued Examination (RCE).
U.S. Appl. No. 12/136,530, Nov. 19, 2010 Final Office Action.
U.S. Appl. No. 12/136,530, Sep. 15, 2010 Response to Non-Final Office Action.
U.S. Appl. No. 12/016,788, Oct. 24, 2011 Non-Final Office Action.
U.S. Appl. No. 12/694,141, Nov. 28, 2011 Non-Final Office Action.
Entry for "citral" Merck Index, 14th Edition.
Abu Bakr Mohammad, Bin Zakariyya Al-Razi; Kitaab-al-Haawi-fil-Tibb, vol. ii (9th century AD), Dayerah-Al-Ma' aarof Is,amoa. Juderabad. 1976 AD p. 434.
Mohammad Shareef Khan; Ilaaj-al-Amraaz (18th centruy AD), Afzal-al-Matabe, Barqi Press, Delhi, 1921 AD p. 335.
Mohammad Azam Khan; Muheet-e-Azam vol. III (19th century AD), Matba Nizami, Kanpur, 1887 AD p. 69.
Mohammad Najmul Ghani Khan; Khazaain-al-Advia, vol. II (20th century AD), Nadeem Yunus Printer/Sheikh Mohd Basheer & Sons, Lahore, 1911 AD p. 657.
Mohammad Azam Khan; Muheet-e-Azam vol. III (19th century AD), Matba Nizami, Kanpur, 1887 AD p. 261.
Mohammad Azam Khan; Muheet-e-Azam vol. I (19th century AD), Matba Nizami, Kanpur, 1896 AD p. 257.
Cakrapanidattah; Cakradattah—Translated by Indradeva Tripathi; Chaukhamba Sanskrit Samsthan (Varanasi), Ed. 4th 2002, p. 260.
U.S. Appl. No. 12/134,918, Nov. 7, 2013 Non-Final Office Action.
"Sheer Moisturizer Hand Sanitizer", *Mintel Global New Products Database*, pp. 1-4 (2010) Retrieved from the Internet: URL:www.gnpd.com [Retrieved on Aug. 34, 2013].
"Antibacterial Wet Wipes", *Mintel Global New Products Database*, pp. 1-2 (2008) Retrieved from the Internet: URL:www.gnpd.com [Retrieved on Sep. 24, 2013].
U.S. Appl. No. 13/335,363, Feb. 19, 2013 Non-Final Office Action.
U.S. Appl. No. 13/412,464, Feb. 8, 2013 Restriction Requirement.
U.S. Appl. No. 12/016,788, Feb. 22, 2013 Amendment and Request for Continued Examination (RCE).
Choudhary, et al., "Solvent-free selective oxidation of benzyl alcohol and benzaldehyde by *tert*-butyl hydroperoxide using $MnO_4^-$-exchanged Mg-Al-hydrotalcite catalsysts", *Catalysis Letters*, 86(4):229-233 (2003).
Zhang, et al., "Antifungal Activities of Major Tea Leaf Volatile Constituents toward Colletorichum Camelliae Massea", *Journal of Agricultural and Food Chemistry*, 54(11):3936-3940 (2006).
U.S. Appl. No. 12/016,788, Aug. 24, 2012 Final Office Action.
U.S. Appl. No. 12/694,141, Jul. 24, 2012 Final Office Action.
Bettini Mercia de Fatima M., "Purification of Orange Peel Oil and Oil Phase by Vacuum Distillation", *Functional Food Ingredients and Nutraceuticals, Processing Technologies*, Edited by john Shi, CRC Press 2006, pp. 157-172.
Cancio, et al., "Burn wound infections" In: *Surgical Treatment: Evidence-Based and Problem-Oriented*, 2001.
Fang, et al., "Prospective clinical study of Hydron, a synthetic dressing, in delivery of an antimicrobial drug to second-degree burns", *J. Burn Care Rehabil.*, 8(3):206-209 (1987).
Judžentiené, et al., "Characterisitcs of essential oil composition in the needles of young Scots pine (*Pinus sylvestris* L.) stands growing along an aerial ammonia gradient", *Chemija*, 17(4):67-73, 2006.
Entry for Lemongrass oil, downloaded Jul. 15, 2012 from internet site: https://www.essentialoils.co.za/essential-oils/lemongrass.htm.
Entry for Orange Oil, downloaded Jul. 15, 2012 from internet https://www.essentialoils.co.za/essential-oils/orange.htm.
Kurita, et al., "Synergistic Antimicrobial Effect of Ehtanol, Sodium Chloride, Acetic Acid and Essentail Oil Components", *Agricultural Biology Chemistry*, 47(1):67-75, 1983.
U.S. Appl. No. 13/412,464, filed Mar. 5, 2012.
U.S. Appl. No. 12/134,918, Jan. 31, 2013 Amendment and Request for Continued Examination (RCE).
Ayliffe, et al., "Hand disinfection: A comparison of various agents in laboratory and ward studies", *Journal of Hospital Infection*, 11(3):226-243 (1988).
Fox, et al., "Comparative evaluation of zinc sulfadiazine and silver sulfadiazine in burn wound infection", *J. Burn Care Rehabil.*, 11(2):112-117 (1990).
Gaonkar, et al., "In vivo efficacy of an alcohol-based surgical hand disinfectant containing a synergistic combination of ethylhexylglycerin and preservatives", *Journal of Hospital Infection*, 63(4):412-417 (2006).
Gaonkar, et al., "An alcohol hand rub containing a synergistic combination of an emollient and preservatives: prolonged activity against transient pathogens", *Journal of Hospital Infection*, 59(1):12-18 (2005).
European Supplementary Search Report for EP 08780771.5, dated Dec. 17, 2012.
International Search Report and Written Opinion for PCT/US2012/052793, dated Nov. 19, 2012.
International Search Report and Written Opinion for PCT/US2012/063013, dated Jan. 4, 2013.
International Search Report and Written Opinion for PCT/US2012/037135, dated Oct. 16, 2012.
U.S. Appl. No. 12/016,788, Aug. 1, 2013 Non-Final Office Action.
U.S. Appl. No. 13/335,363, Nov. 1, 2013 Final Office Action.
U.S. Appl. No. 13/335,363, Aug. 15, 2013 Response to Non-Final Office Action.
U.S. Appl. No. 13/412,464, Sep. 19, 2013 Notice of Non-Compliant.
U.S. Appl. No. 13/412,464, Aug. 8, 2013 Response to Restriction Requirement.
Nazer, et al., "Combinations of food antimicrobials at low levels to inhibit the growth of *Salmonella* sv. Typhimurium: a synergistic effect?", *Food Microbiology*, 22:391-398 (2005).
U.S. Appl. No. 14/267,606, filed May 1, 2014.
U.S. Appl. No. 14/267,403, filed May 1, 2014.
U.S. Appl. No. 14/294,933, filed Jun. 3, 2014.
U.S. Appl. No. 12/016,788, Jun. 19, 2014 Final Office Action.
U.S. Appl. No. 13/335,363, Apr. 1, 2014 Amendment and Request for Continued Examination (RCE).
U.S. Appl. No. 13/412,464, Jul. 7, 2014 Response to Non-Final Office Action.
U.S. Appl. No. 12/134,918, May 7, 2014 Response to Non-Final Office Action.
Cowan, "Plant product as antimicrobial agents", *Clinical Microbiology Reviews*, 12(4):564-582 (1999).
Nannapaneni et al., "Antimicrobial activity of commercial citrus-based natural extracts against *Escherichia coli* O157:H7 isolates and mutant strains", *Foodborne Pathog Dis.*, 5(5):695-699 (2008).
International Search Report and Written Opinion for PCT/US2013/071731, dated Feb. 12, 2014.
Keeven et al., "Evaluating the preservative effectiveness of RGP lens care solutions", *The Contact Lens Association of Ophthalmologists Journal*, 21(4):238-241 (1995).
El-Zemity et al., "Antifungal activity of some essential oils and their major chemical constituents against some phytopathogenic fungi", *Journal of Pest Control and Enviromental Science*, 13(1):87-99 (2005).
U.S. Appl. No. 12/134,918, Aug. 28, 2014 Final Office Action.
U.S. Appl. No. 13/335,363, Sep. 2, 2014 Non-Final Office Action.
U.S. Appl. No. 13/412,464, Oct. 17, 2014 Final Office Action.
Khazaain-al-Advia vol. III (20th century AD), Mohammad Najmul Ghani Khan, Nadeem Yunus Printer/Sheikh Mohd Basheer & Sons, Lahore, 1926 AD p. 1050.
Qaraabaadeen Najm-al-Ghani (20th century AD), Mohammad Najmul Ghani Khan, Munshi Nawal Kishore, Lucknow, (Second Edition) 1928 AD p. 492.

(56) References Cited

OTHER PUBLICATIONS

Khazaain-al-Advia vol. II (20th century AD), Mohammad Najmul Ghani Khan, Nadeem Yunus Printer/Sheikh Mohd Basheer & Sons, Lahore, 1911 AD p. 657.
Kitaab-al-Umdah-fil-Jeraahat, Part I (13th century AD), Aminuddaulah Abul Farj Ibn Al-Quff Maseehi; Dayerah-al-Ma'aarif Usmania, Hyberabad, 1937 AD p. 234-235.
Ziya Al-Din Abdullah Ibn Al-Baitar; al-Jaam'e-li-Mufradaat-al-Advia-wal-Aghzia, vol. II (13th century AD), Matba Amra, Cairo, Egypt, 1874 AD p. 84.
Sodhalanighantauh—(Namasamgraha Va Gunasamgraha) Sodhala; Edited by P.V. Sharma, Oriental Institute, Broda, Edn $1^{st}$ 1978 p. 116.
Khazaain-al-Advia vol. II (20th century AD), Mohammad Najmul Ghani Khan, Nadeem Yunus Printer/Sheikh Mohd Basheer & Sons, Lahore, 1911 AD p. 342-343.
Kitaab-al-Haawi-fil-Tibb, vol. IX (9th century AD), Abu Bakr Mohammad Bin Zakariyya Al-Razi; Dayerah-al-Ma'aarif Usmania, Hyberabad, (First Edition) 1960 AD p. 194.
Khazaain-al-Advia, vol. I ($20^{th}$ century AD) Mohammad Najmul Ghani Khan; Nadeem Yunus Printer/Sheikh Mohd Basheer & Sons, Lahore, 1911 AD p. 669.
Vagabhata; Astanga Hrdaya—(commentary by Arunadutta) edited by Bhisagacarya Harisastri Paradakara Vaidya; Chaukhamba Orientalia, Varanasi, edn. $8^{th}$, 1998 [Time of origin $5^{th}$ century] p. 890.
Mohammad Azam Khan; Muheet-e-Azam, vol. I ($19^{th}$ century AD), Matba Nizami, Kanpur, 1896 AD p. 197.
International Search Report and Written Opinion for PCT/US14/29486, dated Oct. 10, 2014.
Biosecur Lad Inc., "Biosecur™ Product Line Receives Self-Affirmed Gras Status for Use As An Antioxidant And Nutrient Supplement", Biosecur News Release 030811, Mar. 10, 2011, (2 pages).
Hazan et al., "Benzoic Acis, a Weak Organic Acid Food Preservative, Exerts specific Effects on Intracellular Membrane Trafficking Pathways in *Saccharomyces cerevisiae*", Appl. Environ. Microbiol., 70(8):4449 (2004).
Song, et al., "Volatiles from Ficus hispida and their attractiveness to fig wasps", Journal of Chemical Ecology, 27:1929-1942 (2001).
Komthong et al., "Ascending bubble extraction of terpenes from freshly squeezed orange juice", Food Research International, 39:53-58 (2006).
Kumar et al., "Assessment of *Thymus vulgaris* L. essential oil as a safe botanical preservative against post harvest fungal infestation of food commodities", Innovative Food Science & Emerging Technologies, 9(4):575-580 (Oct. 2008).
Gemeda et al., "Effect of essential oils on aspergillus spore germination, growth and mycotoxin production: a potential source of botanical food preservative", APJTB, 4(Suppl. 1):S373-381 (May 2014).
U.S. Appl. No. 12/016,788, Dec. 18, 2014 Amendment and Request for Continued Examination.
U.S. Appl. No. 12/016,788, Mar. 6, 2015 Non-Final Office Action.
U.S. Appl. No. 12/016,788, Jun. 2, 2015 Response to Non-Final Office Action.
U.S. Appl. No. 12/016,788, Oct. 22, 2015 Final Office Action.
U.S. Appl. No. 12/134,918, Jan. 26, 2015 Amendment and Request for Continued Examination.
U.S. Appl. No. 12/134,918, Apr. 22, 2015 Non-Final Office Action.
U.S. Appl. No. 12/134,918, Jul. 31, 2015 Response to Non-Final Office Action.
U.S. Appl. No. 12/134,918, Nov. 4, 2015 Final Office Action.
U.S. Appl. No. 13/412,464, Feb. 17, 2015 Amendment and Request for Continued Examination.
U.S. Appl. No. 13/412,464, Apr. 20, 2015 Non-Final Office Action.
U.S. Appl. No. 13/412,464, Jun. 8, 2015 Response to Non-Final Office Action.
U.S. Appl. No. 13/412,464, Jun. 22, 2015 Final Office Action.
U.S. Appl. No. 13/335,363, Dec. 18, 2014 Response to Non-Final Office Action.
U.S. Appl. No. 13/335,363, Mar. 4, 2015 Final Office Action.
U.S. Appl. No. 13/335,363, Apr. 28, 2015 Amendment and Request for Continued Examination.
U.S. Appl. No. 13/335,363, Jul. 8, 2015 Non-Final Office Action.
U.S. Appl. No. 12/134,911, Sep. 8, 2014 Notice of Allowance.
U.S. Appl. No. 12/134,911, Dec. 8, 2014 Issue Fee Payment.
"Lemongrass Oil: Lighten Up Your Mood with This All-Around Oil", Herbal Oil: Lemongrass Oil Benefits and Uses, 4 pages, 2015. http://articles.mercola.com/herbal-oils/lemongrass-oil.aspx.
Anand, et al., "Biological activities of curcumin and its analogues (Congeners) made by man and Mother Nature" Biochemical Pharmacology, 2008, vol. 76, pp. 1590-1611.
Bagamboula, et al., "Inhibitory effect of thyme and basil essential oils, carvacrol, thymol, estragol, linalool and p-cymene towards Shigella sonnei and S. flexneri" Food Microbiology 21 (2004) 33-42.
Baratta, et al., "Antimicrobial and antioxidant properties of somer commercial essential oils", Flavour Fragr. J., 13, 235±244 (1998).
Biosource Naturals, product sheet for Lemongrass oil. Downloaded Apr. 5, 2015, from http://www.biosourcenaturals.com/lemongrass-essential-oil.htm.
Chalchat, et al., Chemical Composition of Essential Oil of *Calendula oficinalis* L. (Pot Marigold). Flavour and Fragrance Journal, vol. 6, 189-192 (1991).
Chang, et al., Resources and bioactive substances from Taiwania (*Taiwania cryptomerioides*). J. Wood Sci (2003) 49:1-4.
Collins, et al., "A review of alternatives to organophosphorus compounds for the control of storage mites", Journal of Stored Products Research, vol. 42, No. 4, Jan. 1, 2006, pp. 395-426, XP028024314.
DailyMed Antiseptic skin cleanser—Chlorhexidine gluconate, Drug Label Information, updated Sep. 2012.
EP Office Action dated Dec. 2, 2014 in EP Application No. 10 794 733.5.
Fact Sheet on Basil oil from Chemical Book, Downloaded Apr. 5, 2015, from http://www.chemicalbook.com/ChemicalProductProperty_US_CB3405198.aspx.
Nerio, et al., "Repellant activity of essential oils: A review", Biosource Technology, vol. 101, No. 1, Jan. 1, 2010, pp. 372-378, XP026624017.
Panchatcharam, et al., "Curcumin improves wound healing by modulating collagen and decreasing reactive oxygen species", Molecular and Cellular Biochemistry, vol. 290, No. 1-2, Jun. 13, 2006, pp. 87-96, XP019436632.
Prabuseenivasan, et al., "In vitro antibacterial activity of some plant essential oils", BMC Complementary and Alternative Medicine 2006, 6:39, pp. 1-8.
Reagor, et al., "The Effectiveness of Processed Grapefruit-Seed Extract as An Antibacterial Agent: I. An In Vitro Agar Assay" The Journal of Alternative and Complementary Medicine, 2002, vol. 8, pp. 325-332.
Subba, et al., "Antimicrobial Action of Citrus Oils" J. Food Sci. 1967, vol. 32, pp. 225-227.
Supplementary Partial European Search Report dated Aug. 12, 2015 in Application No. 12846062.3.
Table of Acids with Ka and pKa, Downloaded Sep. 28 from the site: Downloaded Sep. 28, 2015, from http://clas.sa.ucsb.edu/staff/Resource%20folder/Chem109ABC/Acid,%20 Base%20Strength/Table%20of%20Acids%20w%20Kas%20and%20pKas.pdf.
Wilson, et al., "The quantification of citral in lemongrass and lemon oils by near-infrared spectroscopy", Journal of Pharmacy and Pharmacology 2002, 54: 1257-1263.
Zeus Quimica, "Zemea Propanediol", Information sheet, downloaded Jun. 24, 2015.
U.S. Appl. No. 13/412,464, Sep. 11, 2015 Notice of Appeal Filed.
U.S. Appl. No. 14/194,381, Jan. 4, 2016 Non-Final Office Action.
U.S. Appl. No. 14/267,403, Nov. 17, 2015 Non-Final Office Action.
U.S. Appl. No. 14/294,933, Dec. 17, 2015 Non-Final Office Action.
Klaric et al., "Antifungal activity of thyme (*Thymus vulgaris* L.) essential oil and thymol against moulds from damp dwellings", 2006, The Society for Applied Microbiology, Letters in Applied Microbiology 44 (2007) 36-42.

(56) References Cited

OTHER PUBLICATIONS

Tayyem et al., "Curcumin Content of Turmeric and Curry Powders", Nutrition and Cancer, 55(2), 126-131, 2006.
U.S. Appl. No. 14/267,606, Jan. 29, 2016 Non-Final Office Action.
Tecophilic TPU—LifeScience Polymers—The Lubrizol Corporation; "Tecophilic TPU"; https://web.archive.org/web/20140923074123/http://www.lubrizol.com/LifeScience/Products/Tecophilic.html; Sep. 23, 2014 [downloaded from internet Jan. 12, 2016]: entire document.
European Search Report dated Jan. 5, 2017.

\* cited by examiner

ANTIMICROBIAL COMPOSITIONS CONTAINING LOW CONCENTRATIONS OF BOTANICALS

PRIORITY CLAIMED

This application is a continuation in part of and claims priority to U.S. patent application Ser. No. 12/367,851, filed Feb. 9, 2009, which is a continuation in part of and claims priority to International Patent Application No. PCT/US08/72006, filed Aug. 1, 2008. PCT/US08/72006 is a continuation in part of and claims priority to U.S. patent application Ser. No. 12/134,918, filed Jun. 6, 2008, which claims priority to U.S. Provisional Application Ser. No. 60/945,288, filed Jun. 20, 2007, and which also is a continuation in part of and claims priority to U.S. patent application Ser. No. 12/016,788,filed Jan. 18, 2008, which claims priority to U.S. Provisional Application Ser. No. 60/953,654, filed Aug. 2, 2007. PCT/US08/72006 is also a continuation in part of and claims priority to U.S. patent application Ser. No. 12/016, 788, filed Jan. 18, 2008, which claims priority to U.S. Provisional Application Ser. No. 60/953,654, filed Aug. 2, 2007. The present application claims priority to each of the above-listed applications and hereby incorporates, by reference, the disclosures of each of the above-listed applications in their entireties herein.

GRANT INFORMATION

Not applicable.

1. INTRODUCTION

The present invention relates to broad spectrum antimicrobial and preservative compositions containing combinations of low concentrations of including one or more essential oil (and/or one or more component thereof), botanical extracts, including plant extracts and fruit extracts, in synergistic combinations with one or more fruit acids and alkanediols. The compositions of the invention may be used as non-toxic alternatives to conventional disinfectants or may be combined with other antimicrobial agents to enhance their activity. The invention provides effective alternatives to harsher products, and may be particularly useful in personal care and household product applications and where children and/or pet exposure may be a concern.

2. BACKGROUND OF THE INVENTION

Essential oils are volatile oils obtained from plant or animal sources and are composed of complex mixtures of several constituents, such as monoterpenes and sesquiterpene hydrocarbons, monoterpene and sesquiterpene alcohols, esters, ethers, aldehydes, ketones, oxides and the like. These essential oils and their isolated constituents are frequently utilized as fragrance and flavor agents, and have been widely used in folk medicine for wound healing properties.

Scientific research has corroborated the beneficial effects of essential oils. Essential oils of eucalyptus have been found to "possess central and peripheral analgesic effects as well as neutrophil-dependent and independent anti-inflammatory activities" (Silva et al., 2003, J. Ethnopharmacol. 89(2-3); 277-283), and similar activity has been observed in essential oils from *Lavendula angustifolia* Mill. (Hajhashemi et al., 2003, J. Ethnopharmacol. 89(1):67-71). Essential oils have been demonstrated to exhibit antibacterial (Bezic et al., 2003, Phytother. Res. 17(9:1037-1040; Goren et al., 2003, Z. Naturforsch. 58(9-10):687-690; de Abreu Gonzaga et al., 2003, Planta Med. 69(8:773-775; Valero and Salmera, 2003, Int. J. Food Microbiol. 85(1-2): 73-81) and antifungal (Paranagama et al., 2003, Lett. Appl. Microbiol. 37(1):86-90; Shin, 2003, Arch. Pharm. Res. 26(5):389-393; Velluti et al., 2003, Int. J. Food Microbiol. 89:145-154) activities. Virucidal activity of essential oils has also been observed, including direct virucidal effects against Herpes simplex viruses types 1 and 2 (Garcia et al., Phytother. Res. 17(9): 1073-1075; Minami et al., 2003, Microbial Immunol. 47(a): 681-684; Schuhmacher et al., 2003, Phytomedicine 10:504-510).

United States Patent Application Publication No. 20050048139 by Modak et al., published Mar. 3, 2005, relates to topical compositions comprising an emollient solvent and an essential oil, which may further comprise additional additives, among which citric acid, glycolic acid and lactic acid are cited. It does not recognize the synergistic activity between essential oils and fruit acids nor does it disclose the concentrations of fruit acids to be used to provide a synergistic effect.

U.S. Patent Application Publication No. 20050019431 by Modak et al., published Jan. 27, 2005, relates to compositions comprising a quaternary ammonium compound and an essential oil (or active component thereof).

A number of patent applications relate to compositions comprising an essential oil (or component thereof) where zinc salts are added to inhibit irritation associated with essential oils. Examples of such patent applications include United States Patent Application Publication No. 20040102429 by Modak et al., published May 27, 2004 and United States Patent Application Publication No. 20050238602 by Modak et al., published Oct. 27, 2005.

U.S. Pat. No. 6,858,317 by Aamodt et al., issued Feb. 22, 2005, relates to methods for protecting wood from mold and sapstaining fungi which employ a non-toxic mold inhibitor which may be a plant extract such as an essential oil.

U.S. Pat. No. 5,100,652 by Kross et al., issued Mar. 31, 1992, relates to low concentration chlorous-acid generating oral hygiene compositions which may comprise an essential oil as a flavoring agent.

U.S. Pat. No. 5,310,546 by Douglas, issued May 10, 1994, relates to a mouthrinse preparation comprising hydrogen peroxide, zinc chloride, sodium citrate, sodium lauryl sulfate, citric acid and ethanol and optionally an essential oil which is a denaturing agent.

BiON offers several skin care products comprising citric acid, botanicals, and other agents for topical use (San Diego, Calif., US).

Johnson et al. (U.S. Pat. No. 6,319,958 and US20020165130) relates to the use of sesquiterpenoids to promote uptake of exogenous antimicrobial compounds. Similarly, a related article discloses the use of sesquiterpenoids, such as nerolidol, farnesol, bisabolol and apritone, in enhancing bacterial permeability and susceptibility to exogenous antimicrobial compounds, suggesting that sesquiterpenoids have a non-specific and general effect (Brehm-Stecher et al. 2003, Antimicrobial Agents and Chemotherapy, 47(10):3357-3360). In particular, Brehm-Stecher et al. report that nerolidol, farnesol, bisabolol and apritone enhanced the susceptibility of *S. aureus* to the antibiotics erythromycin, gentamicin, vancomycin, ciprofloxin, clindamycin, and tetracycline.

U.S. Pat. No. 4,867,898 by Spaulding et al., issued Sep. 19, 1989, relates to a liquid hard surface cleaner comprising pine oil and organic, oil-soluble acids at a pH from 0-6.

U.S. Pat. No. 6,753,305 by Raso and Caselli, issued Jun. 22, 2004, relates to a hard surface disinfectant comprising up to 20 percent of cinnamon oil or a component thereof, 0.01-5 percent of an organic acid, and optionally an additional essential oil.

International Patent Application Publication No. WO2007/077573 by Mukhopadhyay, published Jul. 12, 2007, relates to antimicrobial compositions comprising an antimicrobial agent, such as triclosan, and a functionalized hydrocarbon, where the functionalized hydrocarbon can be an essential oil, and/or a solvent.

There is a continuing desire for an antimicrobial composition that is non-irritating, safe, and effective for repeated use in various professional and non-professional settings.

3. SUMMARY OF THE INVENTION

The present invention relates to skin or surface antimicrobial and preservative compositions with broad spectrum antimicrobial containing low concentrations of one or more essential oil (and/or one or more component (i.e., an "Individual Constituent" or "IC") thereof), and botanical extracts including plant and fruit extracts, in synergistic combinations of one or more fruit acids and alkanediols. It is based, at least in part, on the discovery that the low concentrations of specific combinations of these ingredients have an unexpected synergistic effect, namely the combinations can confer superior antimicrobial properties on personal care, veterinary, as well as household products.

In preferred, non-limiting embodiments, the compositions of the invention further comprise an alkanediol, particularly a bifunctional fatty alcohol, enhances antimicrobial activity still more. In various non-limiting embodiments, the compositions may include a solvent which includes alcohol, glycols, or vegetable oils.

In various non-limiting embodiments, the compositions of the present invention may include a total stock solution concentrations of essential oils and botanical extracts in concentrations ranging from about 0.5% to about 30% (w/w), preferably from about 2% to about 20% (w/w). In stock solutions, the compositions of the present invention contain from about 0.3% to about 15% (w/w), preferably from about 0.5% to about 6.0% (w/w) essential oil or individual constituent thereof; from about 0.3% to about 30% (w/w), preferably from about 1% to about 20% (w/w), more preferably from about 1% to about 15% (w/w) botanical extracts; from about 5% to about 20% (w/w), preferably from about 10% to about 20% (w/w) fruit acids; from about 1% to about 80% (w/w), preferably from about 20% to about 80% (w/w), more preferably from about 30% to about 80% (w/w), more preferably from about 30% to about 50% (w/w) alkanediols; and from about 0% to about 90% (w/w), preferably from about 0% to about 80% (w/w) solvents. In specific non-limiting embodiments, in final products (such as creams or soaps), the synergistic compositions of the present invention contain low total concentrations of essential oils ranging from about 0.01% to about 0.5% (w/w), more preferably from about 0.02% to about 0.1% (w/w); and botanical extracts are present in final products in amounts ranging from about 0.1 to about 0.5% (w/w); and with fruit acids in amounts ranging from 5% to about 20% (w/w). Solvent systems include alcohol, glycerol, diglycerol, propylene glycol, dipropylene glycol, and vegetable oils.

In various non-limiting embodiments, the present invention may be utilized in personal care products such as soaps, scrubs, cosmetics, topical creams and lotions, wound care products, disinfecting wipes, and veterinary products such as pet shampoos, and therapeutic ointments. The compositions of the invention may be used in concentrations from about 1% to about 5% in personal care products or topical creams. Alternatively, 10% to about 20% of the stock solutions of the compositions may be used in soap formulations. Additionally, the compositions contain no or little to very mild added fragrance.

The compositions of the invention may be used as non-toxic alternatives to conventional disinfectants or may be combined with to other antimicrobial agents to enhance their activity, particularly providing persistent antimicrobial protection without causing skin sensitivity. The invention provides effective alternatives to harsher products which may be particularly useful in personal care and household products and where children and/or pet exposure may be a concern.

4. DETAILED DESCRIPTION OF THE INVENTION

For clarity of description, and not by way of limitation, the detailed description of the invention is divided into the following subsections:

(4.1) essential oils;
(4.2) botanical extracts;
(4.3) fruit acids;
(4.4) alkanediols;
(4.5) solvents;
(4.6) combinations of essential oils/ICs and fruit acids;
(4.7) compositions comprising alkanediols;
(4.8) compositions comprising essential oils/ICs, botanical extracts, fruit acids and alkanediols;
(4.9) personal care products;
(4.10) veterinary products;
(4.11) household/industrial products; and
(4.12) preservative compositions.

4.1 Essential Oils

Essential oils ("EOs"), as defined herein, are volatile oils obtained from plant or animal sources, or their synthetic equivalents, and are composed of complex mixtures of several constituents as monoterpenes and sesquiterpene hydrocarbons, monoterpene and sesquiterpene alcohols, esters, ethers, aldehydes, ketones, oxides and the like. Examples of EOs include, but are not limited to, cinnamon oil, basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, eucalyptus oil, lemon oil, orange oil, sweet orange oil, pomegranate oil, manuka oil, and *calendula* oil. In preferred non-limiting embodiments of the invention, the EO is selected from one or more EO from the group consisting of cinnamon oil (bark or leaf), lemongrass oil, citronella oil, basil oil, and orange oil.

Individual constituents ("ICs") of essential oils may be isolated from the oil (natural) or entirely or partially synthetic, and include, but are not limited to, curcumin, 1-citronellol, α-amylcinnamaldehyde, lyral, geraniol, farnesol, hydroxycitronellal, isoeugenol, eugenol, camphor, eucalyptol, linalool, citral, thymol, limonene and menthol. Further examples of ICs include sesquiterpenoid compounds, which may be the active compounds in the essential oils. Sesquiterpenoid compounds, containing 15 carbons, are formed biosynthetically from three 5-carbon isoprene units. Sesquiterpenoid compounds include, but are not limited to, farnesol, nerolidol, bisabolol, apritone, chamazulene, santalol, zingiberol, carotol, and caryophyllen.

Mixtures of one or more EO, one or more IC, and one or more EO as well as one or more IC, are encompassed by the present invention. In specific non-limiting embodiments of the invention, an IC is selected from the (non-limiting) group consisting of camphor, curcumin, alpha-pinene, constituents of cinnamon leaf oil such as, cinnamaldehyde, cinnamylacetic ester, cinnamic acid, ethyl cinnamate, methyl chavicol, linalool, beta-caryophyllene, and eugenol; constituents of lemongrass oil such as d-limonene, geranyl acetate, nerol, geraniol, citral, and/or myrcene; constituents of citronella oil such as geraniol, citronellol, citronellal, geranyl acetate, limonene, methyl isoueugenol, and/or elemol; components of basil oil such as camphor, limonene, and/or β-selinene; and constituents of orange oil such as α-pinene, sabinene, myrcene, limonene, linalool, citronellal, neral and/or geranial. An EO or IC for use in the invention may be obtained from its natural source or may be chemically synthesized.

In various non-limiting embodiments, low concentrations of essential oils and ICs are used. Specifically, the concentrations of each essential oil or IC in the final products may range from about 0.01% to about 0.5% (w/w), preferably from about 0.02% to about 0.1% (w/w). Essential oils or ICs are present in stock solutions in amounts ranging from about 0.3% to about 15% (w/w), preferably from about 0.5% to about 6.0% (w/w). The total concentrations of essential oils and botanical extracts in stock solutions may range from about 0.5% to about 30% (w/w), preferably from about 2% to about 20% (w/w). These concentrations (and others recited throughout) may be increased in stock solutions intended for dilution, where the above ranges provide for the concentration after dilution.

4.2 Botanical Extracts

Botanical extracts, as defined herein, include plant, herbal, and fruit extracts, which are not "essential oils" as noted above. The botanicals utilized herein include but are not limited to *Camellia sinensis* (green tea), grapes, pomegranate, Echinacea, Centella Asiatica, Elderflower, Irish moss, Mallow, soap bark, Yucca, Clary sage, and mixtures thereof. The botanical utilized to obtain the botanical extract may be obtained from any of the plant parts including the leaves, pulp, seeds, or stems as well as the whole plant. Herbal extracts can be, for example, standardized extracts that are dispersible and/or soluble in aqueous medium.

Examples of herbal extracts include, without limitation, extracts of chamomile, rosemary, *aloe*, nettle, *Centella asiatica, ginkgo biloba, betula*, and witch hazel. Such extracts may be delivered in a carrier such as water, propylene glycol, hydroalcohol, glycerine, or butylene glycol. Additional extracts with nutritional quality can be used, including, without limitation, green tea, grape skin, grape seed, grapefruit, grapefruit seed, bilberry, blueberry, *Ginkgo biloba*, soy isoflavones, black cohosh, St. John's wort, *echinacea*, chamomile, rosemary, aloe, nettle, and *Centella asiatica*. Botanical extracts can be obtained from, for example, Active Organics (Lewisville, Tex.), New Age Botanicals (Garland, Tex.), Triarco Industries (Wayne, N.J.), and Aloecorp (Broomfield, Colo.).

Additional Examples of botanical extracts include natural blends of fatty acids which mimic those found in the stratum corneum, mixture of fatty acids with pigments such as carotenes, carotenoids or phytosterols that are known to facilitate repair to damaged skin, and the like. Specific examples of useful botanical extracts include avocado, which contains the sterol sitosterol; carrot, which contains beta carotene; sesame oil which contains a mixture of saturated and unsaturated fatty acids, and brazil nut oil. Because of its broad distribution of fatty acids, extracts such as brazil nut oil, can outperform single fatty acids with respect to incorporation into the lipid lamellar structures. Brazil nut oil (BNO) originates from the harvested fruit from the South American rain forest tree: *Bertholletia excelsa.*

In various non-limiting embodiments, low concentrations of botanical extracts are used. Specifically, the concentrations in final products may range from about 0.1% to about 0.5%. The total concentrations of essential oils and botanical extracts may range from about 0.5% to about 30% or from about 2% to about 20%. Botanical extracts are present in stock solutions in concentrations ranging from about 0.3% to about 30%, preferably from about 1% to about 20% (w/w), more preferably from about 1% to about 15% (w/w).

4.3 Fruit Acids

Fruit acids which may be used according to the invention include but are not limited to citric acid, glycolic acid, lactic acid, malic acid, tartaric acid and acetic acid. In preferred non-limiting embodiments of the invention, the fruit acid is citric acid. In other preferred non-limiting embodiments of the invention, the fruit acid is malic acid. In other preferred non-limiting embodiments, the fruit acid is Multifruit BSC from Arch Chemicals. Multifruit BSC is a mixture of lactic, citric, tartaric, glycolic, and malic acid extracted from plants.

A fruit acid for use in the invention may be obtained from its natural source or may be chemically synthesized.

In non-limiting embodiments of the invention, the stock solution concentrations of the fruit acids ranges from about 5% to about 20%, more preferably from about 10% to about 20%.

4.4 Alkanediols

In non-limiting embodiments, bifunctional alcohols which may be used according to the present invention are alkanediols. Suitable alkanediols include, but are not limited to, dodecanediol, decanediol, nonanediol, octanediol, heptanediol, hexanediol and pentanediol.

In particular non-limiting embodiments, the alkanediols have a carbon backbone of between 9 and 25 carbon atoms, including but not limited to 1,9 Nonanediol, 1,2-Decanediol, 1,10-Decanediol, 1,11-Undecanediol, 1,2-Dodecanediol, 1,12 Dodecanediol, Cyclododecanediol, 1,13-Tridecanediol, 1,2-Tetradecanediol, 1,14-Tetradecanediol, 1,15-Pentadecanediol, 1,16-Hexadecanediol, 1,17-Heptadecanediol, 1,18-Octadecanediol, 1,19-Nonadecanediol, 1,20-Eicosanediol, 1,21-Heneicosanediol, 1,22-Docosanediol, 1,23-Tricosanediol, 1,24-Tetracosanediol, 1,25-Pentacosanediol. The preferred alkanediols are 1,2-Decanediol, 1,10-Decanediol, 1,2-Dodecanediol, 1,12-Dodecanediol, Cyclododecanediol, 1,13-Tridecanediol, 1,2-Tetradecanediol, 1,14-Tetradecanediol and the most preferred alkanediols are 1,2-Decanediol, 1,2-Dodecanediol and 1,2-Tetradecanediol.

In non-limiting embodiments of the invention, the stock solution concentrations of the alkanediols ranges from about 1% to about 80% (w/w), preferably from about 20% to about 80% (w/w), more preferably from about 30% to about 80% (w/w), more preferably from about 30% to about 50% (w/w).

4.5 Solvents

In various non-limiting embodiments, the compositions of the present invention may include a solvent including but not limited to water, alcohols, glycols, glycerol, glycerine, diglycerol, propylene glycol, dipropylene glycol, and vegetable oils.

Preferred but non-limiting examples of non-alkanediol alcohols for solubilisation are aliphatic alcohols having carbon atoms about 1 to 8 such as methanol, ethanol, n-propanol, isopropyl alcohol, 2-methyl-2 propanol, hexanol, or combinations thereof. Aromatic alcohols, for example, but not by way of limitation, phenoxyethanol, benzyl alcohol, 1-phenoxy-2propanol, and/or phenethyl alcohol, may also optionally be used in combination with aliphatic alcohols.

The solvents are used in stock solution concentrations ranging from about 0% to about 90% (w/w), preferably from about 0% to about 80% (w/w). Alcohol concentrations range from about 0% to about 90%. Phenoxyethanol concentrations range from about 0% to about 40%. Propylene glycol concentrations range from about 0% to about 80%. Vegetable oil concentrations may range from about 0% to about 50%.

4.6 Combinations of Essential Oils/ICs and Fruit Acids

In various non-limiting embodiments, the present invention provides for compositions comprising a combination of one or more essential oil (and/or one or more IC thereof) and one or more fruit acid. Preferably, this combination produces a synergistic anti-microbial effect against at least one microbe selected from the group consisting of *Escherichia coli, Pseudomonas aeruginosa, Staphylococcus aureus*, methicillin-resistant *S. aureus*, and *Candida albicans* ("synergistic" means that the antimicrobial effect of the combination is greater than the sum of the antimicrobial effects of the individual components).

In particular, non-limiting embodiments of the invention, the compositions comprise between about 0.1 and 1.2 percent (weight/weight) or between 0.1 and 1.0 percent (weight/weight) ("w/w") of one or more essential oils, one or more ICs, or a combination thereof (where a combination is used, the total of essential oil(s) and/or IC(s) is between about 0.1 and 1.0 percent (weight/weight) and between about 0.125 and 2.0 percent (weight/weight) of one or more fruit acid (where more than one fruit acid is used, the total amount of fruit acids present is between about 0.125 and 2.0 percent (weight/weight)). "About" as used in this document means plus or minus 20 percent of the recited value, so that, for example, "between about 0.125 and 1.0 percent" means a range between 0.125±0.025 and 1.0±0.2.

In particular, non-limiting embodiments, the present invention provides for concentrates of essential oil/IC/fruit acid combinations which are concentrated and may be diluted to provide a composition for personal, household, or industrial use. In such concentrates, the ratio of fruit acid to essential oil(s)/IC(s) (weight/weight) is between about 1 and 16, for example, but not by way of limitation, fruit acid(s): EO(s)/IC(s) of between about 1:1 to 10:1, inclusive (weight/weight).

The present invention further provides for methods of providing an antimicrobial effect to a surface comprising applying, to the surface, an effective amount of a composition as described herein. An antimicrobial effect means killing and/or inhibiting the growth/proliferation of a microbe. In particular non-limiting embodiments of the invention, the microbe is selected from the group consisting of from the group consisting of *Escherichia coli, Pseudomonas aeruginosa, Staphylococcus aureus*, methicillin-resistant *S. aureus*, and *Candida albicans*. In specific non-limiting embodiments, the composition is exposed to the surface for at least 20 seconds, at least 30 seconds, or at least 60 seconds, or at least 5 minutes or at least 10 minutes. In various non-limiting embodiments, the surface may be the a skin or mucosal surface, a household surface (e.g., a surface of a countertop, Table sink, toilet, wall, floor, appliance, window, shower surface, rug, upholstery, fabric, etc.) or an industrial surface (e.g., a surface of a countertop, Table sink, toilet, wall, floor, appliance, window, shower surface, rug, upholstery, fabric, etc.).

In a first set of specific, non-limiting embodiments, the present invention provides for a composition comprising a component selected from the group consisting of cinnamon oil, cinnamaldehyde, eugenol, cinnamylacetic ester, and cinnamic acid, at a concentration of between about 0.1 and 1.2 percent (weight/weight) or between about 0.2 and 0.6 percent (weight/weight), as well as citric acid at a concentration of between about 0.5 and 1.5 percent (weight/weight), optionally further comprising triclosan at a concentration of between about 0.05 and 3 percent (weight/weight) or between about 0.05 and 0.1 percent (weight/weight) (this range, and all ranges herein, inclusive). In certain embodiments, the EO/IC is not cinnamon oil or pine oil or an IC thereof.

In a second set of non-limiting embodiments, the present invention provides for compositions comprising a EO/IC mixture comprising two or more EO or IC from the group consisting of cinnamon oil or an IC thereof, lemongrass oil and/or an IC thereof, orange oil and/or an IC thereof, basil oil and/or an IC thereof, and citronella oil and/or an IC thereof, at a total EO/IC concentration of between about 0.1 and 1 percent (weight/weight); together with one or more fruit acid (preferably citric acid), at a total fruit acid concentration of between about 0.125 and 2 percent (weight/weight); and an alcohol (preferably ethanol at a concentration of between about 5-20 percent (weight/weight), optionally further comprising triclosan at a concentration of between about 0.05 and 3 percent (weight/weight) or between about 0.05 and 0.1 percent (weight/weight), where the ratio of EO/IC to fruit acid is between about 1:1 to about 1:10. In certain embodiments, the EO/IC is not cinnamon oil or pine oil or an IC thereof.

In a third set of non-limiting embodiments, the present invention provides for compositions comprising a EO/IC mixture comprising lemongrass oil and/or an IC thereof, orange oil and/or an IC thereof, and optionally one or more additional EO and/or IC, at a total EO/IC concentration of between about 0.1 and 1 percent (weight/weight); together with one or more fruit acid (preferably citric acid), at a total fruit acid concentration of between about 0.125 and 2 percent; and an alcohol (preferably ethanol) at a concentration of between about 5-20 percent (weight/weight), optionally further comprising triclosan at a concentration of between about 0.05 and 1 percent (weight/weight) or between about 0.05 and 0.3 percent (weight/weight), where the ratio of EO/IC to fruit acid is between about 1:1 to about 1:10.

4.7 Compositions Comprising Alkanediols

In non-limiting embodiments, the present invention provides for compositions comprising an essential oil, a fruit acid, an alcohol which is not an alkanediol, and an alkanediol.

In particular, non-limiting embodiments, the carbon backbone of the alkanediol has between 9 and 25 carbon atoms.

In particular non-limiting embodiments, the present invention provides for compositions comprising (i) between about 0.2 and 0.7 percent (weight/weight) of one or more essential oil as set forth above and preferably selected from the group consisting of lemongrass, cinnamon oil, citronella oil, basil oil, orange oil and combinations thereof; (ii) a non-alkanediol alcohol solvent at a concentration between about 0.5 and 20 percent (weight/weight); (iii) an amount of alkanediol which increases the antimicrobial effect, for example at a concentration between about 0.3 and 1.0 percent (weight/weight), and (iv) one or more fruit acid at a total concentration between about 0.125 and 2.0 percent (weight/weight).

The preferred essential oils are the ones that show significant enhancement of antimicrobial activity in combination with citric acid. These oils include one or more selected from lemongrass oil, cinnamon oil, basil oil and citronella oil (preferably at a total concentration of between about 0.2 and 0.7 percent (weight/weight), with the optional further addition of orange oil to reduce the pungent odor of the other essential oils and to provide a fragrance which is mild and pleasant. Fruit acids which may be used in such compositions include citric acid or lactic acid (preferably citric acid) at a concentration between about 0.5 and 1.0 percent (weight/weight).

Preferred but non-limiting examples of non-alkanediol alcohols for solubilisation of both essential oils and citric acid are aliphatic alcohols having carbon atoms about 1 to 8 such as methanol, ethanol, n-propanol, isopropyl alcohol, 2-methyl-2 propanol, hexanol, or combinations thereof, at a concentration of between about 5 and 20 percent (weight/weight). Aromatic alcohols, for example, but not by way of limitation, phenoxyethanol, benzyl alcohol, 1-phenoxy-2propanol, and/or phenethyl alcohol, for example at a concentration of between about 0.5 and 5 percent (weight/weight) may also optionally be used in combination with aliphatic alcohols. A further solvent which optionally may be comprised in a composition of the invention is isopropyl myristate. Most preferred aliphatic alcohols include ethanol, denatured alcohol (SDA 40B and SDA 3C) and isopropanol. Most preferred aromatic alcohols include phenoxyethanol and phenethanol.

Compositions comprising lemongrass or cinnamon oils (0.2-0.5% (weight/weight)) and orange oil (0.1-0.2% (weight/weight)), exhibit a pleasant and mild fragrance. Furthermore these oils even at these lower concentrations have been observed to provide superior antibacterial activity (more than 3 log reduction when challenged with $10^8$ colony forming unit of a gram positive pathogen (*S. aureus*) in combination with a secondary alcohol (0.3-1.0% (weight/weight)) and alcohol (5-20% (weight/weight)).

In specific, non-limiting embodiments, the present invention provides for a skin or surface disinfectant composition comprising the essential oil lemongrass (0.3-0.5% (weight/weight)), orange oil (0.1-0.2% (weight/weight)), citric acid (0.5-2.0% (weight/weight)), SDA 40B alcohol (5-20% (weight/weight)) and 1,2 decanediol (0.3-1.0% (weight/weight)).

Preferably the pH of personal care products is between about 3.5-5.0, and preferably between about 4-4.7.

In addition to the above ingredients, a composition of the invention may optionally further comprise an emollient to further reduce irritation, such as, but not limited to, a fatty alcohol, behentrimonium methosulfate-cetyl alcohol (Incroquat TMS), or a polyol such as glycerol, propylene glycol, diglycerol, ethylene glycol, diethylene glycol, triethylene glycol, dipropylene glycol, tripropylene glycol, hexylene glycol, butylene glycol, etc.

Essential oils are volatile and therefore it is desirable that the antimicrobial composition containing essential oils is incorporated in a suitable base in which it is stable at higher temperature and over a long period of time. Accordingly, a composition of the invention may optionally comprise a hydrophilic or hydrophobic gel forming polymer, a fatty acids, a plant oils etc. Suitable hydrophilic gel polymers include, but are not limited to, hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), and chitosan pyrrolidone carboxylate (Kytamer PC), silica gel, carbomerpolymers etc. Suitable hydrophobic gel polymers include, but are not limited to, silicone polymers, for example polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C and Q2-5220 Silicone Fluid), silicone glycol (BASF 1066 DCG polyol), KSG series Silicone gels (Shin-etsu), and combinations thereof. Suitable plant oils include, but are not limited to, olive oil, almond oil, avocado oil, basil oil, primrose oil, peanut oil, safflower oil, sesame oil, soyabean oil, wheat germ oil.

4.8 Compositions Comprising Essential Oils/ICs, Botanical Extracts, Fruit Acids, and Alkanediols In non-limiting embodiments, the present invention provides for compositions comprising a low concentration essential oil or IC and a low concentration botanical extract in synergistic combination with a fruit acid and alkanediol. In various non-limiting embodiments, the compositions of the present invention include total stock solution concentrations of essential oils and botanical extracts in concentrations ranging from about 0.5% to about 30%, more preferably from about 2% to about 20%.

In particular, non-limiting embodiments of the invention, stock solutions containing the compositions comprise from about 0.3% to about 15% (w/w), preferably from about 0.5% to about 6.0% (w/w) of essential oils or ICs; from about 0.3% to about 30%, preferably from about 1% to about 20% (w/w), more preferably from about 1% to about 15% (w/w) of botanical extracts; from about 5% to about 20% (w/w), more preferably from about 10% to about 20% (w/w) fruit acids; from about 1% to about 80% (w/w), preferably from about 20% to about 80% (w/w) alkanediols, more preferably from about 30% to about 80% (w/w), more preferably from about 30% to about 50% (w/w) alkanediols; from about 0% to about 90% (w/w), preferably from about 0% to about 80% (w/w) solvents. In other specific non-limiting embodiments, the synergistic compositions of the present invention in final products contain low concentrations of essential oils or ICs ranging from about 0.01% to about 0.5%, more preferably from about 0.02% to about 0.1%; and botanical extracts ranging from about 0.1 to about 0.5%. Solvent systems include, but are not limited to, alcohol, glycerol, diglycerol, propylene glycol, dipropylene glycol, and vegetable oils.

The low concentration compositions of the invention may be used in concentrations from about 1% to about 5% in personal care products or topical creams. Alternatively, from about 10% to about 20% of the stock solutions of the compositions may be used in soap formulations. Additionally, the compositions contain no or little to very mild fragrance.

The compositions of the invention may be used as alternatives to conventional disinfectants or may be combined with to other antimicrobial agents to enhance their activity, particularly providing persistent antimicrobial protection without causing skin sensitivity.

4.9 Personal Care Products

In non-limiting embodiments, the present invention provides for personal care product compositions comprising low concentrations of one or more essential oil and/or IC and botanical extracts including plant and fruit extracts, in synergistic combination with one or more fruit acids and alkanediols, as set forth in section 4.8 above. In preferred, non-limiting embodiments, the low concentrations of the active agents are such that regular exposure of skin to the personal care product does not produce skin irritation in a normal subject.

Non-limiting examples of personal care products which may utilize the invention include bar soap, liquid soap (e.g., hand soap), hand sanitizer, cleansing wipes, disinfecting wipes, body wash, acne treatment products, shampoo, conditioner, cosmetics (including but not limited to liquid or powder foundation, liquid or solid eyeliner, mascara, cream eye shadow, tinted powder, "pancake" type powder to be used dry or moistened, etc.) deodorant, antimicrobial creams, body lotion, hand cream, topical cream, aftershave lotion, skin toner, mouth wash, toothpaste, sunscreen lotion, and baby products such as, but not limited to, cleansing wipes, baby shampoo, baby soap, and diaper cream. The present invention may also be applied to wound care items, such as, but not limited to, wound healing ointments, wound coverings, bandages, tape, and steri-strips, and medical articles such as medical gowns, caps, face masks, and shoe-covers, surgical drops, etc.

Personal care compositions according to the invention, in addition to one or more essential oil and/or IC together with one or more fruit acid, may further comprise one or (preferably) more than one component selected from the group consisting of emollients, stabilizing agents, thickening agents, humectants, anti-inflammatory agents, antimicrobial agents, neutralizing agents, surfactants, water, silicone polymers, alcohols, and hydrogels, as well as additional components as may be known in the art. Non-limiting examples of such components are set forth below.

In various non-limiting embodiments of the invention, a personal care product comprising a combination of one or more essential oil and/or IC together with one or more fruit acid may further comprise an emollient, for example PEG 20 almond glycerides, Probutyl DB-10, Glucam P-20, Glucam E-10, Glucam P-10, Glucam E-20, Glucam P-20 distearate, glycerin, propylene glycol, octoxyglycerine, cetyl acetate, acetylated lanolin alcohol (e.g., Acetulan), cetyl ether (e.g., PPG-10), myristyril ether (e.g., PPG-3), hydroxylated milk glycerides (e.g., Cremeral HMG), polyquaternium compounds (e.g., U-care compounds), copolymers of dimethyl dialyl ammonium chloride and acrylic acid (e.g., Merquat), dipropylene glycol methyl ethers (e.g., Dowanol DPM, Dow Corning), polypropylene glycol ethers (e.g., Ucon 50-HB-600, Union Carbide) and silicon polymers. Other suitable emollients may include hydrocarbon-based emollients such as petrolatum or mineral oil, fatty ester-based emollients, such as methyl, isopropyl and butyl esters of fatty acids such as isopropyl palmitate, isopropyl myristate, isopropyl isostearate, isostearyl isostearate, diisopropyl sebacate, and propylene dipelargonate, 2-ethylhexyl isononoate, 2-ethylhexyl stearate, $C_{12}$-$C_{16}$ fatty alcohol lactates such as cetyl lactate and lauryl lactate, isopropyl lanolate, 2-ethylhexyl salicylate, cetyl myristate, oleyl myristate, oleyl stearate, oleyl oleate, hexyl laurate, and isohexyl laurate. Additional useful emollients include lanolin, olive oil, cocoa butter, and shea butter.

In various non-limiting embodiments of the invention, a personal care product comprising a combination of one or more essential oil and/or IC together with one or more fruit acid may further comprise a stabilizing agent consisting of antioxidants, including but not limited to vitamin C (ascorbic acid) and vitamin E (tocopherol), and surfactants, including but not limited to incromide or silicone-based surfactants (Masil SF-19, BASF).

In various non-limiting embodiments of the invention, a personal care product comprising a combination of one or more essential oil and/or IC together with one or more fruit acid may further comprise a thickening and/or gelling agent such as stearyl alcohol, cationic hydroxy ethyl cellulose (Ucare; JR30), hydroxy propyl methyl cellulose, hydroxy propyl cellulose (Klucel), chitosan pyrrolidone carboxylate (Kytamer), behenyl alcohol, zinc stearate, emulsifying waxes, including but not limited to Incroquat and Polawax, an addition polymer of acrylic acid, a resin such as Carbopol® ETD™ 2020, guar gum, acacia, acrylates/steareth-20 methacrylate copolymer, agar, algin, alginic acid, ammonium acrylate co-polymers, ammonium alginate, ammonium chloride, ammonium sulfate, amylopectin, attapulgite, bentonite, C9-15 alcohols, calcium acetate, calcium alginate, calcium carrageenan, calcium chloride, caprylic alcohol, carbomer 910, carbomer 934, carbomer 934P, carbomer 940, carbomer 941, carboxymethyl hydroxyethyl cellulose, carboxymethyl hydroxypropyl guar, carrageenan, cellulose, cellulose gum, cetearyl alcohol, cetyl alcohol, corn starch, damar, dextrin, dibenzlidine sorbitol, ethylene dihydrogenated tallowamide, ethylene diolamide, ethylene distearamide, gelatin, guar gum, guar hydroxypropyltrimonium chloride, hectorite, hyaluronic acid, hydrated silica, hydroxybutyl methylcellulose, hydroxyethylcellulose, hydroxyethyl ethylcellulose, hydroxyethyl stearamide-MIPA, isocetyl alcohol, isostearyl alcohol, karaya gum, kelp, lauryl alcohol, locust bean gum, magnesium aluminium silicate, magnesium silicate, magnesium trisilicate, methoxy PEG-22/dodecyl glycol copolymer, methylcellulose, microcrystalline cellulose, montmorillonite, myristyl alcohol, oat flour, oleyl alcohol, palm kernel alcohol, pectin, PEG-2M, PEG-5M, polyacrylic acid, polyvinyl alcohol, potassium alginate, potassium aluminium polyacrylate, potassium carrageenan, potassium chloride, potassium sulfate, potato starch, propylene glycol alginate, sodium acrylate/vinyl alcohol copolymer, sodium carboxymethyl dextran, sodium carrageenan, sodium cellulose sulfate, sodium chloride, sodium polymethacylate, sodium silicoaluminate, sodium sulfate, stearalkonium bentonite, stearalkonium hectorite, stearyl alcohol, tallow alcohol, TEA-hydrochloride, tragacanth gum, tridecyl alcohol, tromethamine magnesium aluminium silicate, wheat flour, wheat starch, xanthan gum, abietyl alcohol, acrylinoleic acid, aluminum behenate, aluminum caprylate, aluminum dilinoleate, aluminum salts, such as distearate, and aluminum isostearates, beeswax, behenamide, butadiene/acrylonitrile copolymer, C29-70 acid, calcium behenate, calcium stearate, candelilla wax, carnauba, ceresin, cholesterol, cholesterol hydroxystearate, coconut alcohol, copal, diglyceryl stearate malate, dihydroabietyl alcohol, dimethyl lauramine oleate, dodecanoic acid/cetearyl alcohol/glycol copolymer, erucamide, ethylcellulose, glyceryl triacetyl hydroxystearate, glyceryl tri-acetyl ricinolate, glycol dibehenate, glycol di-octanoate, glycol distearate, hexanediol distearate, hydrogenated C6-14 olefin polymers, hydrogenated castor oil, hydrogenated cottonseed oil, hydrogenated lard, hydrogenated menhaden oil, hydrogenated palm kernel glycerides, hydrogenated palm kernel oil, hydrogenated palm oil, hydrogenated polyisobutene, hydrogenated soybean oil, hydrogenated tallow amide, hydrogenated tallow glyceride, hydrogenated vegetable glyceride, hydrogenated vegetable oil, Japan wax, jojoba wax, lanolin alcohol, shea butter, lauramide, methyl dehydroabietate, methyl hydrogenated rosinate, methyl rosinate, methylstyrene/vinyltoluene copolymer, microcrystalline wax, montan acid wax, montan wax, myristyleicosanol, myristyloctadecanol, octadecene/maleic anhyrdine copolymer, octyldodecyl stearoyl stearate, oleamide, oleostearine, ouricury wax, oxidized polyethylene, ozokerite, paraffin, pentaerythrityl hydrogenated rosinate, pentaerythrityl tetraoctanoate, pentaerythrityl rosinate, pentaerythrityl tetraabietate, pentaerythrityl tetrabehenate, pentaerythrityl tetraoleate, pentaerythrityl tetrastearate, ophthalmic anhydride/ glycerin/glycidyl decanoate copolymer, ophthalmic/ trimellitic/glycols copolymer, polybutene, polybutylene terephthalate, polydipentene, polyethylene, polyisobutene, polyisoprene, polyvinyl butyral, polyvinyl laurate, propylene glycol dicaprylate, propylene glycol dicocoate, propylene glycol diisononanoate, propylene glycol dilaurate, propylene glycol dipelargonate, propylene glycol distearate, propylene glycol diundecanoate, PVP/eiconsene copolymer, PVP/hexadecene copolymer, rice bran wax, stearlkonium bentonite, stearalkonium hectorite, stearamide, stearamide DEA-distearate, stearamide DIBA-stearate, stearamide MEA-stearate, stearone, stearyl erucamide, stearyl stearate, stearyl stearoyl stearate, synthetic beeswax, synthetic wax, trihydroxystearin, triisononanoin, triisostearin, tri-isostearyl trilinoleate, trilaurin, trilinoleic acid, trilinolein, trimyristin, triolein, tripalmitin, tristearin, zinc laurate, zinc myristate, zinc neodecanoate, zinc rosinate, and mixtures thereof. The gelling agents used in vehicles may be natural gelling agents such as natural gums, starches, pectins, agar and gelatin. Often, the gelling agents are based on polysaccharides or proteins Examples include but are not limited to guar gum, Xanthum gum, Alginic acid (E400), sodium alginate (E401), potassium alginate (E402), ammonium alginate (E403), calcium alginate (E404, —polysaccharides from brown algae), Agar (E406, a polysaccharide obtained from red seaweeds), Carrageenan (E407, a polysaccharide obtained from red seaweeds), Locust bean gum (E410, a natural gum from the seeds of the Carob tree), Pectin (E440, a polysaccharide obtained from apple or citrus-fruit), and Gelatin (E441, made by partial hydrolysis of animal collagen).

In various non-limiting embodiments of the invention, a personal care product comprising a combination of one or more essential oil and/or IC together with one or more fruit acid may further comprise a humectant, such as, for example, glycerin, 1-2-propylene glycol, dipropylene glycol, polyethylene glycol, 1,3-butylene glycol, or 1,2,6-hexanetriol.

In certain non-limiting embodiments of the invention, essentially the entire antimicrobial effect of the inventive composition is achieved by an antimicrobial composition consisting of one or more essential oil and/or one or more IC, together with a fruit acid and optionally an alcohol. In alternative embodiments of the invention, one or more additional antimicrobial agent may be comprised, for example, in the amount of between about 0.05 and 2.0 percent (weight/weight), where such antimicrobial agent may be selected from the group consisting of iodophors, iodine, benzoic acid, dihydroacetic acid, propionic acid, sorbic acid, methyl paraben, ethyl paraben, propyl paraben, butyl paraben, cetrimide, benzalkonium chloride, dequalinium chloride, chlorhexidine, chloroeresol, chlorxylenol, benzyl alcohol, bronopol, chlorbutanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, silver sulfadiazine, octoxyglycerine, biguanides such as, but not limited to, chlorhexidine free base, chlorhexidine palmitate, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, and parahexamethylenebiguanide ("PHMB").

In various non-limiting embodiments of the invention, a personal care product comprising a combination of one or more essential oil and/or IC together with one or more fruit acid may further comprise a neutralizing agent to neutralize carboxyl groups present in one or more other component, such as carboxyl groups in a thickening agent. Suitable neutralizing agents include diisopropylamine and triethanolamine.

In various non-limiting embodiments of the invention, a personal care product comprising a combination of one or more essential oil and/or IC together with one or more fruit acid may further comprise a surfactant. The surfactant may be an anionic surfactant, a cationic surfactant, an ampholytic surfactant, or a nonionic surfactant. Examples of nonionic surfactants include polyethoxylates, fatty alcohols (e.g., ceteth-20 (a cetyl ether of polyethylene oxide having an average of about 20 ethylene oxide units) and other "BRIJ"® nonionic surfactants available from ICI Americas, Inc. (Wilmington, Del.)), cocamidopropyl betaine, alkyl phenols, fatty acid esters of sorbitol, sorbitan, or polyoxyethylene sorbitan. Suitable anionic surfactants include ammonium lauryl sulfate and lauryl ether sulfosuccinate. A preferred surfactant is lauroyl ethylenediamine triacetic acid sodium salt at a concentration between about 0.5-2.0% (weight/weight). In particular non-limiting embodiments of the invention, concentrations of surfactant are between about 0.05% and 2% (weight/weight).

In various non-limiting embodiments of the invention, a personal care product may comprise water.

In various non-limiting embodiments of the invention, a personal care product comprising a combination of one or more essential oil and/or IC together with one or more fruit acid may further comprise a hydrogel comprising, for example, a compound such as hydroxypropylmethyl cellulose, cationic hydroxyethyl cellulose (U-care polymers), ethyl cellulose, hydroxypropyl cellulose, hydroxymethyl cellulose, carboxy methyl cellulose, polyethylene oxide (polyox resins), and chitosan pyrrolidone carboxylate (Kytomer PC).

In various non-limiting embodiments of the invention, a personal care product comprising a combination of one or more essential oil and/or IC together with one or more fruit acid may further comprise an alcohol or a mixture of alcohols, for example, ethanol, isopropyl DMDM hydantoin, and sunscreens such as aminobenzoic acid, arobenzone, cinoxate, diioxybenzone, homosalate, menthyl anthranilate, octocrylene, octyl methoxycinnamate, octyl salicylate, oxybenzoate, padimate 0, phenylbenzimidazole, sulfonic acid, sulisobenzone, titanium dioxide, trolamine salicylate and zinc oxide.

In one set of non-limiting embodiments, the present invention provides for personal care compositions comprising one or more EO/IC, preferably where the EO(s)/IC(s) are selected from the group consisting of lemongrass oil and/or an IC thereof, orange oil and/or an IC thereof, cinnamon leaf oil and/or an IC thereof, basil oil and/or an IC thereof, eugenol, cinnamaldehyde, cinnamylacetic ester, and cinnamic acid, at a total concentration of between about 0.1 and 1% (weight/weight); a fruit acid, preferably citric acid, at a concentration of between about 0.125 and 1% (weight/weight); an alcohol, preferably ethanol, at a concentration of between about 5 and 20% (weight/weight); and optionally triclosan at a concentration of between about 0.05 and 1% (weight/weight), where the ratio of EO(s)/IC(s) to the fruit acid(s) is between about 1:1 to 1:10 and the pH is between about 3 and about 7, preferably between about 5 and 6.

In another set of non-limiting embodiments, the present invention provides for personal care compositions comprising lemongrass oil or an IC thereof and orange oil or an IC thereof at a total concentration of between about 0.2 and 0.7% (weight/weight); a fruit acid, preferably citric acid, at a concentration of between about 0.25 and 1% (weight/weight); an alcohol, preferably ethanol, at a concentration of between about 5 and 20% (weight/weight); and optionally triclosan at a concentration of between about 0.05 and 1% (weight/weight), where the ratio of EO(s)/IC(s) to fruit acid(s) is between about 1:1 to 1:5 and the pH is between about 3 and about 7, preferably between 5 and 6.

In various non-limiting embodiments of the invention, a personal care product comprising a combination of one or more essential oil and/or IC together with one or more fruit acid may further comprise various anti-inflammatory, antimicrobial agents, anti-irritants, and gelling ingredients. Such compositions may be included in, for example, wound healing ointments. The antimicrobial botanicals contemplated for wound treatment include 0.2-0.7% (weight/weight) essential oils such as lemongrass oil (LG) or orange oil (O), and 0.2-1.0% (weight/weight) fruit acids such as citric acid (Cit) and lactic acid (L), and 0.5-1.0% (weight/weight) phenoxyethanol, which is a constituent of sage oil (PXE). Anti-irritant, anti inflammatory botanicals include, but are not limited to 0.3-0.7% (weight/weight) *Calendula* oil (Co), 0.1-0.5% (weight/weight) turmeric extract (curcumin (Cr)), 0.2-2.0% (weight/weight) salicylic acid (S), 0.2-0.5% (weight/weight) Camphor (Cm) and 2-30% (weight/weight) honey (H). Gelling agents would include, but are not limited to, Guar gum, Xanthum gum Alginic acid, and Pectin in amounts of 0.2-3.0% (weight/weight).

In one specific, non-limiting embodiment, the present invention provides for a liquid soap product called "CN1-A" having one of the following compositions (CN1-A1 OR CN1-A2).

TABLE 1

| CN1-A Compositions | | |
|---|---|---|
| | Ingredient | % (weight/weight) |
| CN1-A1: | Deionized water | 59.15 |
| | Polyox N 60K | 0.2 |
| | Pluronic F 87 Prill | 2.0 |
| | Ucare Jr 30 | 0.4 |
| | D,L Panthenol 50 W | 1.0 |
| | Incromide oxide L | 3.0 |
| | Crosultane C-50 | 3.0 |
| | Montalene C 40 | 3.0 |
| | 2-Phenoxy-ethanol | 1.0 |
| | Zinc gluconate | 0.1 |
| | Glycerine | 2.0 |
| | SDA-40B alcohol | 15.5 |
| | Cinnamon leaf oil | 0.5 |
| | Citric acid | 1.0 |
| | Orange oil | 0.2 |
| | Distilled water | 7.95 |
| CN1-A2: | Deionized water | 59.25 |
| | Polyox N 60K | 0.2 |
| | Pluronic F 87 Prill | 2.0 |
| | Ucare Jr 30 | 0.4 |
| | D,L Panthenol 50 W | 1.0 |
| | Incromide oxide L | 3.0 |
| | Crosultane C-50 | 3.0 |
| | Montalene C 40 | 3.0 |
| | 2-Phenoxy-ethanol | 1.0 |
| | Glycerine | 2.0 |
| | SDA-40B alcohol | 15.5 |
| | Cinnamon leaf oil | 0.5 |
| | Citric acid | 1.0 |
| | Orange oil | 0.2 |
| | Distilled water | 7.95 |

In another specific, non-limiting embodiment, the present invention provides for a liquid soap product called "CN1-B" having the following composition.

TABLE 2

| CN1-B | |
|---|---|
| Ingredient | % (weight/weight) |
| Deionized water | 63.2 |
| Methocel 40-101 | 0.1 |
| Pluronic F 87 Prill | 0.1 |
| Ucare Jr 30 | 0.1 |
| D,L Panthenol 50 W | 1.0 |
| Incromide oxide L | 3.0 |
| Crosultane C-50 | 3.0 |
| Montalene C 40 | 1.5 |
| 2-Phenoxy-ethanol | 1.0 |
| Glycerine | 2.0 |
| SDA-40B alcohol | 15.5 |
| Cinnamon leaf oil | 0.5 |
| Citric acid | 1.0 |
| Orange oil | 0.2 |
| Distilled water | 7.8 |

In another specific, non-limiting embodiment, the present invention provides for a liquid soap product called "CN1-C" having the following composition.

TABLE 3

| Ingredient | % (weight/weight) |
| --- | --- |
| CN1-C | |
| Deionized water | 63.2 |
| Methocel 40-101 | 0.1 |
| Pluronic F 87 Prill | 0.1 |
| Ucare Jr 30 | 0.1 |
| D,L Panthenol 50 W | 1.0 |
| Incromide oxide L | 3.0 |
| Crosultane C-50 | 3.0 |
| Montalene C 40 | 1.5 |
| 2-Phenyl-ethanol | 1.0 |
| Glycerine | 2.0 |
| SDA-40B alcohol | 15.5 |
| Cinnamon leaf oil | 0.5 |
| Citric acid | 1.0 |
| Orange oil | 0.2 |
| Distilled water | 7.8 |

In a subset of non-limiting embodiments, the present invention provides for a soap comprising one or more essential oil, 1% citric acid, and a soap base comprising a surfactant, an emollient, and a thickener, and having a pH between about 3-5. Specific non-limiting examples of such soaps follow.

TABLE 4

Soap Containing Lemongrass oil, and Citric acid (LG-Cit-4)
(4 represents total oil 0.4%)

| Ingredient | % (w/w) |
| --- | --- |
| Deionized Water | 63.5 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Lemongrass oil | 0.4 |

TABLE 5

Soap Containing Lemongrass oil, and Citric acid (LG-Cit-6)
(6 represents total oil 0.6%)

| Ingredient | % (w/w) |
| --- | --- |
| Deionized Water | 63.3 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Lemongrass oil | 0.6 |

TABLE 6

Soap Containing Lemongrass oil, Orange oil (O oil) and Citric acid
(LGO-Cit 6) (6 represents total oil 0.6%)

| Ingredient | % (w/w) |
| --- | --- |
| Deionized Water | 63.3 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Lemongrass oil | 0.4 |
| Citric acid | 1.0 |
| Orange oil | 0.2 |

TABLE 7

Soap Containing Lemon grass oil, Orange oil and Citric acid (LGO-Cit 7)
(7 represents total oil 0.7%)

| Ingredient | % (w/w) |
| --- | --- |
| Deionized Water | 63.2 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Lemongrass oil | 0.5 |
| Citric acid | 1.0 |
| Orange oil | 0.2 |

TABLE 8

Soap Containing Cinnamon oil, Orange oil and Citric acid (CO -Cit 6)
(6 represents total oil 0.6%)

| Ingredient | % (w/w) |
| --- | --- |
| Deionized Water | 63.3 |
| Methocel 40-101 | 0.1 |
| Pluronic F 87 Prill | 0.1 |
| Ucare Jr 30 | 0.1 |
| DL Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Cinnamon oil | 0.4 |
| Citric acid | 1.0 |
| Orange oil | 0.2 |

TABLE 9

Soap Containing Cinnamon oil, Orange oil and Citric acid (CO -Cit 7)
(7 represent total oil 0.7%)

| Ingredient | % (w/w) |
| --- | --- |
| Deionized Water | 63.2 |
| Methocel 40-101 | 0.1 |

TABLE 9-continued

Soap Containing Cinnamon oil, Orange oil and Citric acid (CO -Cit 7)
(7 represent total oil 0.7%)

| Ingredient | % (w/w) |
|---|---|
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Cinnamon oil | 0.5 |
| Citric acid | 1.0 |
| Orange oil | 0.2 |

TABLE 10

Soap Containing Orange oil and Citric acid (O-Cit 2)
(2 represents total oil 0.2%)

| Ingredient | % (w/w) |
|---|---|
| Deionized Water | 63.7 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Orange oil | 0.2 |
| Citric acid | 1.0 |

TABLE 11

Soap Containing Basil oil ("B oil"), Orange oil ("O oil")
and Citric acid (BO-Cit 6) (6 represents total oil 0.6%)

| Ingredient | Percentage (w/w) |
|---|---|
| Deionized Water | 63.3 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Basil oil | 0.4 |
| Citric acid | 1.0 |
| Orange oil | 0.2 |

TABLE 12

Soap containing Citronella oil ("CR oil"), Orange oil("O oil"),
Citric acid (CRO-Cit6) (6 represents total oil 0.6%)

| Ingredient | Percentage (w/w) |
|---|---|
| Deionized Water | 63.3 |
| Methocel 40-101 | 0.1 |
| Pluronic F 87 Prill | 0.1 |
| Ucare Jr 30 | 0.1 |
| D,L Panthenol 50 W | 1.0 |
| Incromide Oxide L | 3.0 |
| Crosultane C-50 | 3.0 |
| Montalene C 40 | 1.5 |
| 2-Phenoxy-Ethanol | 1.0 |
| Glycerin | 2.0 |
| SDA 40B | 15.5 |
| Citronella oil | 0.4 |
| Citric acid | 1.0 |
| Orange oil | 0.2 |

In further specific, non-limiting embodiments, the present invention provides for the following combinations of agents in a soap base (percentages weight/weight):

0.15% TC+0.4% lemongrass oil+0.2% orange oil+1% citric acid;

0.4% lemongrass oil+0.2% orange oil+1% citric acid; or 0.15% TC+0.4% cinnamon oil+0.2% orange oil+1% citric acid; or 0.4% cinnamon oil+0.2% orange oil+1% citric acid.

In still further specific, non-limiting embodiments, the present invention provides for the following combinations of agents in a soap base (percentages w/w):

Cinnamon oil 0.5%+Orange Oil 0.2%+Citric acid 1.0%+alcohol (e.g., denatured ethyl alcohol, such as SDA 40 B) 5.5%+TC 0.14% (or TC 0.15%); or Lemongrass oil 0.5%+Orange Oil 0.2%+Citric acid 1.0%+alcohol (e.g., denatured ethyl alcohol, such as SDA 40B) 5.5%+TC 0.14% (or TC 0.15%); or Lemongrass oil 0.5%+Citric acid 1.0%+alcohol (e.g. denatured ethyl alcohol such as SDA 40 B) 5.5%+TC 0.14% (or TC 0.15%).

In specific non-limiting embodiments, the present invention provides for compositions comprising (0.2-0.3% (weight/weight)) of essential oils such as lemongrass or cinnamon and 0.1-0.2% (weight/weight) orange oil when used in combination with 1% citric acid and alkanediols such as 1,2 decanediol, 1,2 dodecanediol and 1,12 dodecanediol, as set forth above. In a specific, non-limiting embodiment, the present invention provides for a soap formulation comprising 0.3% (weight/weight) of lemongrass oil or cinnamon oil in combination with 0.1% (weight/weight) orange oil, and 1% (weight/weight) citric acid with and without alkanediols, where the pH preferably is between 4.5-4.6. The following Tables provide non-limiting embodiments of the present invention.

TABLE 13

Soap containing Lemon grass oil, Orange oil and Citric acid
(LG-O-Cit 5) (5 represents total oil 0.5%)

| Ingredient | Percentage (w/w) |
|---|---|
| Deionized Water | 64.8 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |

TABLE 13-continued

Soap containing Lemon grass oil, Orange oil and Citric acid (LG-O-Cit 5) (5 represents total oil 0.5%)

| Ingredient | Percentage (w/w) |
| --- | --- |
| Lemon grass oil | 0.3 |
| Citric acid | 1.0 |
| Orange oil | 0.2 |
| pH 4.55 | |

TABLE 14

Soap Containing Lemon grass oil, Orange oil and Citric acid (LG-O-Cit 4) (4 represents total oil 0.4%)

| Ingredient | Percentage (w/w) |
| --- | --- |
| Deionized Water | 64.9 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.1 |
| pH 4.64 | |

TABLE 15

Soap Containing LG-O-Cit 5 and 0.3%1,2 Decanediol

| Ingredient | Percentage (w/w) |
| --- | --- |
| Deionized Water | 64.5 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.2 |
| 1,2 Decanediol | 0.3 |
| pH 4.6 | |

TABLE 16

Soap Containing LG-O-Cit-4 and 0.3%1,2 Decanediol

| Ingredient | Percentage (w/w) |
| --- | --- |
| Deionized Water | 64.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.1 |
| 1,2 Decanediol | 0.3 |
| pH 4.6 | |

TABLE 17

Soap Containing LG-O-Cit 4, 0.3% 1,2 Decanediol + 0.5% Incroquat behenyl TMS

| Ingredient | Percentage (w/w) |
| --- | --- |
| Deionized Water | 64.1 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.1 |
| 1,2 Decanediol | 0.3 |
| Incroquat TMS | 0.5 |
| pH 4.6 | |

TABLE 18

Soap Containing LG-O-Cit 4 and 0.3%1,2 Dodecanediol

| Ingredient | Percentage (w/w) |
| --- | --- |
| Deionized Water | 64.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.1 |
| 1,2 Decanediol | 0.3 |
| pH 4.6 | |

TABLE 19

Soap Containing LG-O-Cit 4 and 0.3%1,12 Dodecanediol

| Ingredient | Percentage (w/w) |
| --- | --- |
| Deionized Water | 64.6 |
| Methocel 40-101 | 0.2 |
| Pluronic F 87 Prill | 1.0 |
| Polyox WSR-N-60K | 0.2 |

TABLE 19-continued

Soap Containing LG-O-Cit 4 and 0.3%1,12 Dodecanediol

| Ingredient | Percentage (w/w) |
|---|---|
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.1 |
| 1,12 Dodecanediol | 0.3 |
| pH 4.6 | |

TABLE 20

Soap Containing LG-O-Cit 4 and 0.3% 1,2 tetradecanediol

| Ingredient | Percentage (w/w) |
|---|---|
| Deionized Water | 64.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 15.0 |
| Lemon grass oil | 0.3 |
| Citric acid | 1.0 |
| Orange oil | 0.1 |
| 1,2 Tetradecanediol | 0.3 |
| pH 4.6 | |

TABLE 21

Soap Containing LG-O-Cit 4A
(Same as LG-O-Cit 4 but contains 17% SDA-40B alcohol instead of 15%)

| Ingredient | Percentage (w/w) |
|---|---|
| Deionized Water | 62.9 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Lemon grass oil | 0.3 |
| Citric acid | 1.0 |
| Orange oil | 0.1 |
| pH 4.64 | |

TABLE 22

Soap Containing LG-O-Cit 4A and 0.5%1,2 Decanediol

| Ingredient | Percentage (w/w) |
|---|---|
| Deionized Water | 62.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Lemon grass oil | 0.3 |
| Citric acid | 1.0 |
| Orange oil | 0.1 |
| 1,2 Decanediol | 0.5 |
| pH 4.6 | |

TABLE 23

Soap Containing LG-O-Cit 4A and 0.5%1,2 Dodecanediol

| Ingredient | Percentage (w/w) |
|---|---|
| Deionized Water | 62.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Lemon grass oil | 0.3 |
| Citric acid | 1.0 |
| Orange oil | 0.1 |
| 1,2 Dodecanediol | 0.5 |
| pH 4.6 | |

TABLE 24

Soap Containing LG-O-Cit 4A and 0.5%1,12 Dodecanediol

| Ingredient | Percentage (w/w) |
|---|---|
| Deionized Water | 62.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Lemon grass oil | 0.3 |
| Citric acid | 1.0 |
| Orange oil | 0.1 |
| 1,12 Dodecanediol | 0.5 |
| pH 4.6 | | alcohol, n-propyl alcohol, and mixtures thereof; fatty alcohols, including, but not limited to, cetyl alcohol, myristol alcohol, stearyl alcohol, octyl alcohol, decyl alcohol and lauryl alcohol, and mixtures thereof; and hexanol.

In various non-limiting embodiments of the invention, a personal care product comprising a combination of one or more essential oil and/or IC together with one or more fruit acid may further comprise a silicone polymer, for example one or more than one polydimethylsiloxane polymer (Dow Corning 225 Silicone Fluid), dimethiconol fluid in dimethicone (Dow Corning 1403 Silicone Fluid), cyclomethicone and dimethicone copolyl (Dow Corning 3225C Silicone Fluid), and silicone glycol (BASF 1066 DCG polyol). In particular, non-limiting embodiments, the amount of silicone polymer is between about 0.1 and 1.0 percent (volume/volume).

In various non-limiting embodiments of the invention, a personal care product comprising a combination of one or more essential oil and/or IC together with one or more fruit acid may further comprise an emollient solvent such as a glycidyl ether having an alkyl chain up to and including 18 carbon molecules and ethoxylates and propoxylates thereof; a glyceryl ether having an alkyl chain up to and including 18 carbon molecules and ethoxylates and propoxylates thereof, a mono- or diglyceryl ether having an alkyl chain up to and including 18 carbon molecules and ethoxylates and propoxylates thereof, ethoxylate and propoxylate ethers, ethoxy diglycol esters, ethyl hexyl alcohol propoxylate, and propylene glycol esther ethoxylates and propoxylates, and Arlamol (Altas).

In various non-limiting embodiments of the invention, a personal care product comprising a combination of one or more essential oil and/or IC together with one or more fruit acid may further comprise additives such as dyes, fragrances, pH adjusters, including basic pH adjusters such as ammonia, mono-, di- and tri-alkyl amines, mono-, di- and tri-alkanolamines, alkali metal and alkaline earth metal hydroxides (e.g., ammonia, sodium hydroxide, potassium hydroxide, lithium hydroxide, monoethanolamine, triethylamine, isopropylamine, diethanolamine and triethanolamine); acid pH adjusters such as mineral acids and polycarboxylic acids (e.g., hydrochloric acid, nitric acid, phosphoric acid, sulfuric acid, citric acid, glycolic acid, and lactic acid); vitamins such as vitamin A, vitamin E and vitamin C; polyamino acids and salts, such as ethylenediamine tetraacidic acid (EDTA), preservatives such as German plus and

TABLE 25

Soap Containing LG-O-Cit 4A and 0.5%1,2 Tetradecanediol

| Ingredient | Percentage (w/w) |
| --- | --- |
| Deionized Water | 62.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Lemon grass oil | 0.3 |
| Citric acid | 1.0 |
| Orange oil | 0.1 |
| 1,2 tetradecanediol | 0.5 |
| pH 4.6 | |

TABLE 26

Soap Containing Cn-O-Cit 4A

| Ingredient | Percentage (w/w) |
| --- | --- |
| Deionized Water | 62.9 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Cinnamon oil | 0.3 |
| Citric acid | 1.0 |
| Orange oil | 0.1 |
| pH 4.64 | |

TABLE 27

Soap Containing Cn-O-Cit 4A + 0.5% 1,2 decanediol

| Ingredient | Percentage (w/w) |
| --- | --- |
| Deionized Water | 62.6 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| SDA 40B | 17.0 |
| Cinnamon oil | 0.3 |
| Citric acid | 1.0 |
| Orange oil | 0.1 |
| 1,2 Decanediol | 0.5 |
| pH 4.64 | |

TABLE 28

Soap Base

| Ingredient | Percentage (w/w) |
| --- | --- |
| Deionized Water | 81.3 |
| Methocel 40-101 | 0.2 |
| Pluronic F 87 Prill | 1.0 |
| Polyox WSR-N-60K | 0.2 |
| Ucare Jr 30 | 0.3 |
| D,L Panthenol 50 W | 1.0 |
| Incromide Oxide L | 8.0 |
| Crosultaine C-50 | 3.0 |
| Montalene C 40 | 2.0 |
| 2-Phenoxy-Ethanol | 1.0 |
| Glycerin | 2.0 |
| pH 4.64 (adjusted with 10N hydrochloric acid) | |

In certain non-limiting embodiments of the invention, where the compositions are used in soap formulations, the compositions may contain from about 0.5% to about 55% (w/w), preferably from about 0.5% to about 15% (w/w) essential oils or ICs; from about 1% to about 30% (w/w), preferably from about 1% to about 5% (w/w) botanical extracts; from about 1% to about 20% (w/w), preferably from about 1% to about 10% (w/w) alkanediols; from about 5% to about 20% (w/w), preferably from about 5% to about 15% (w/w) fruit acids; and from about 0% to about 90% (w/w) solvents. The following tables provide non-limiting embodiments of the present invention that contain a soap base.

TABLE 29

LG-6-O

| Ingredient | % (w/w) |
|---|---|
| Lemongrass oil | 0.3 |
| Grapefruit seed extract | 0.2 |
| Orange oil | 0.1 |
| Octanediol | 0.5 |
| SDA 3C | 4.9 |
| Citric Acid | 1.0 |
| Softsoap Base (Colgate Palmolive) | 93.0 |

TABLE 30

LG-6-S

| Ingredient | % (w/w) |
|---|---|
| Lemongrass oil | 0.3 |
| Grapefruit seed extract | 0.2 |
| Orange oil | 0.1 |
| Symclariol | 0.5 |
| Phenoxyethanol | 1.0 |
| SDA 3C | 3.9 |
| Citric Acid | 1.0 |
| Softsoap Base (Colgate Palmolive) | 93.0 |

TABLE 31

LG-6-O-TC

| Ingredient | % (w/w) |
|---|---|
| Lemongrass oil | 0.3 |
| Grapefruit seed extract | 0.2 |
| Orange oil | 0.1 |
| Octanediol | 0.5 |
| SDA 3C | 4.75 |
| Citric Acid | 1.0 |
| Triclosan | 0.15 |
| Softsoap Base (Colgate Palmolive) | 93.0 |

TABLE 32

LG-19-O

| Ingredient | % (w/w) |
|---|---|
| Water | 63.1 |
| Methocil (40-101) | 0.2 |
| U-care Jr | 0.3 |
| Pluronic F-87 | 1.0 |
| Montalene C-40 | 2.0 |
| Incromine oxide L | 8.0 |
| Crosultane C-50 | 3.0 |
| Glycerine | 2.0 |
| Polyoxyl SR-N-60K | 0.2 |
| SDA 40 B | 17.1 |
| Citric acid | 1.0 |
| Lemongrass oil | 0.3 |
| Orange oil | 0.1 |
| Grapefruit seed extract | 0.2 |
| Phenoxy ethanol | 1.0 |
| Octanediol | 0.5 |

TABLE 32-continued

LG-19-O

| Ingredient | % (w/w) |
|---|---|

TABLE 33

LG-19-S

| Ingredient | % (w/w) |
|---|---|
| Water | 63.1 |
| Methocil (40-101) | 0.2 |
| U-care Jr | 0.3 |
| Pluronic F-87 | 1.0 |
| Montalene C-40 | 2.0 |
| Incromine oxide L | 8.0 |
| Crosultane C-50 | 3.0 |
| Glycerine | 2.0 |
| Polyoxyl SR-N-60K | 0.2 |
| SDA 40 B | 17.1 |
| Citric acid | 1.0 |
| Lemongrass oil | 0.3 |
| Orange oil | 0.1 |
| Grapefruit seed extract | 0.2 |
| Phenoxy ethanol | 1.0 |
| Symclariol | 0.5 |

The following Tables provide non-limiting lotion embodiments of the present invention.

TABLE 34

Antibacterial topical lotion comprising LG-O-Cit A + 1,2Decanediol ("LG-O-Cit A-D Lotion")

| Ingredient | Percentage (w/w) |
|---|---|
| Water | 65.9 |
| U Care-JR 30M | 0.25 |
| PolyoxWSR-205 | 0.1 |
| Incroquat TMS Behenyl | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerin | 2.0 |
| Allantoin | 0.2 |
| Dimethicone copolyol (Q2-5220) | 2.5 |
| Citric acid | 1.0 |
| 1,2 decanediol | 0.5 |
| Tocopheryl acetate | 0.5 |
| Glyceryl stearate (Arlacel165) | 1.0 |
| Butylene glycol | 3.0 |
| SDA-40-B | 15 |
| Lemongrass oil | 0.5 |
| Tea tree oil | 0.5 |
| Orange oil | 0.1 |
| 1,2 Decanediol(Symclairol) | 0.5 |
| (pH adjusted to 4.5-5.0) | |

TABLE 35

Antibacterial topical lotion comprising LG-O-Cit A + 1,2Decanediol + Triclosan ("LG-O-Cit A-D-T Lotion")

| Ingredient | Percentage (w/w) |
|---|---|
| Water | 65.6 |
| U Care-JR 30M | 0.25 |
| PolyoxWSR-205 | 0.1 |
| Incroquat TMS Behenyl | 2.0 |

TABLE 35-continued

Antibacterial topical lotion comprising
LG-O-Cit A + 1,2Decanediol + Triclosan ("LG-O-Cit A-D-T Lotion")

| Ingredient | Percentage (w/w) |
| --- | --- |
| Isopropyl myristate | 1.0 |
| Acetulan | 1.0 |
| Vitamin E | 0.2 |
| Zinc stearate | 0.2 |
| Polawax NF | 2.75 |
| Glycerin | 2.0 |
| Allantoin | 0.2 |
| Dimethicone copolyol (Q2-5220) | 2.5 |
| Citric acid | 1.0 |
| 1,2 decanediol | 0.5 |
| Tocopheryl acetate | 0.5 |
| Glyceryl stearate (Arlacel165) | 1.0 |
| Butylene glycol | 3.0 |
| SDA-40-B | 15 |
| Lemongrass oil | 0.5 |
| Tea tree oil | 0.5 |
| Orange oil | 0.1 |
| 1,2 Decanediol(Symclairol) | 0.5 |
| Triclosan | 0.3 |
| (pH adjusted to 4.5-5.0) | |

TABLE 36

Antibacterial-anti inflammatory topical lotion comprising
LG-O-CitA + 1,2 Decanediol ("LG-O-Cit A-D AB/AIF Lotion")

| Ingredient | Percentage (w/w) |
| --- | --- |
| Water | 65.6 |
| U Care-JR 30M | 0.25 |
| PolyoxWSR-205 | 0.1 |
| Incroquat TMS Behenyl | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerin | 2.0 |
| Allantoin | 0.2 |
| Dimethicone copolyol (Q2-5220) | 2.5 |
| Citric acid | 1.0 |
| 1,2 decanediol | 0.5 |
| Tocopheryl acetate | 0.5 |
| Glyceryl stearate (Arlacel165) | 1.0 |
| Butylene glycol | 3.0 |
| SDA-40-B | 15 |
| Lemongrass oil | 0.5 |
| Tea tree oil | 0.5 |
| Orange oil | 0.1 |
| 1,2 Decanediol(Symclairol) | 0.5 |
| Curcumin | 0.2 |
| Camphor | 0.1 |
| (pH adjusted to 4.5-5.0) | |

Specific non-limiting examples of antimicrobial formulations follow below.

TABLE 37

Antimicrobial Impregnation solution

| Ingredient | Percentage (w/w) |
| --- | --- |
| Lemongrass oil | 0.3 |
| Orange oil | 0.1 |
| Tea tree oil | 0.5 |
| Calandula oil | 0.5 |
| Citric acid | 1.0 |
| Olive oil | 5.0 |
| Propylene glycol | 10 |
| Decanediol | 0.5 |
| SDA 40 B alcohol | 51.7 |
| U care JR 30 | 0.4 |
| Water | 30 |

TABLE 38

Antimicrobial/anti-inflammatory Impregnation solution

| Ingredient | Percentage (w/w) |
| --- | --- |
| Lemongrass oil | 0.3 |
| Orange oil | 0.1 |
| Tea tree oil | 0.3 |
| Calandula oil | 0.5 |
| Citric acid | 1.0 |
| Olive oil | 5.0 |
| Propylene glycol | 10 |
| Decanediol | 0.5 |
| SDA 40 B alcohol | 51.0 |
| U care JR 30 | 0.4 |
| Curcumin | 0.3 |
| Water | 29.7 |

In specific, non-limiting embodiments, the present invention provides for the preparation of topical cream formulations containing anti-irritant, anti-inflammatory agents, gelling agents, and botanicals for minor cuts and wounds. Specific cream formulations are as follows.

TABLE 39

Cream 1 (LGO-L-PXE-Co)

| Ingredients | Percentage (w/w) |
| --- | --- |
| Water | 65.74 |
| Xanthum gum | 0.5 |
| Glycerin | 15.0 |
| Panthenol (75W) | 0.66 |
| Lemon grass oil | 0.4 |
| Orange oil | 0.1 |
| Calandula oil | 0.5 |
| Lactic acid | 0.5 |
| Phenoxy ethanol | 0.7 |
| Safflower oil | 15.0 | pH adjusted to 4.5 with 10 N NaOH

TABLE 40

Cream 2 (LGO-L-PXE-Co-S)

| Ingredients | Percentage (w/w) |
| --- | --- |
| Water | 65.54 |
| Xanthum gum | 0.5 |
| Glycerin | 15.0 |
| Panthenol (75W) | 0.66 |
| Lemon grass oil | 0.4 |
| Orange oil | 0.1 |
| Calandula oil | 0.5 |
| Lactic acid | 0.5 |
| Phenoxy ethanol | 0.7 |
| Safflower oil | 15.0 |
| Salicylic acid | 0.2 | pH adjusted to 4.5 with 10 N NaOH

TABLE 41

Cream 3 (LGO-L-PXE-Co-Cr)

| Ingredients | Percentage (w/w) |
| --- | --- |
| Water | 59.25 |
| Xanthum gum | 0.5 |
| Glycerin | 15.0 |
| Panthenol (75W) | 0.66 |
| Lemon grass oil | 0.4 |
| Orange oil | 0.1 |
| Calendula oil | 0.5 |
| Lactic acid | 0.5 |
| Phenoxy ethanol | 0.7 |
| Safflower oil | 15.0 |
| Curcumin | 0.2 | pH adjusted to 4.5 with 10 N NaOH

TABLE 42

Cream 4 (LGO-L-PXE-Co-Cm-H)

| Ingredients | Percentage (w/w) |
| --- | --- |
| Water | 55.54 |
| Xanthum gum | 0.5 |
| Glycerin | 15.0 |
| Panthenol (75W) | 0.66 |
| Lemon grass oil | 0.4 |
| Orange oil | 0.1 |
| Calendula oil | 0.5 |
| Lactic acid | 0.5 |
| Phenoxy ethanol | 0.7 |
| Safflower oil | 15.0 |
| Camphor | 0.2 |
| Honey | 10.0 | pH adjusted to 4.5 with 10 N NaOH

TABLE 43

Cream 5 (LGO-L-PXE-Co-S)

| Ingredients | Percentage (w/w) |
| --- | --- |
| Water | 65.04 |
| Xanthum gum | 0.5 |
| Glycerin | 15.0 |
| Panthenol (75W) | 0.66 |
| Lemon grass oil | 0.4 |
| Orange oil | 0.1 |
| Calendula oil | 0.5 |
| Lactic acid | 0.5 |
| Phenoxy ethanol | 0.7 |
| Safflower oil | 15.0 |
| Salicylic acid | 0.2 |
| 1,2-decanediol | 0.5 | pH adjusted to 4.5 with 10 N NaOH

4.10 Veterinary Products

In a subset of non-limiting embodiments, the present invention provides for veterinary products comprising a combination of one or more essential oil and/or IC together with one or more fruit acid, as set forth in section 4.4 or 4.5, above. The term "veterinary", as used here, means "pet care", and includes home use as well as use in a veterinary office or other pet care establishment.

Non-limiting examples of veterinary care products which may utilize the invention include pet shampoo, pet cleansing wipes including body wipes, ear wipes, and eye wipes, ear cleaning liquid, cage cleaner, surface cleaner for housebreaking accidents, topical creams, ointments, teat dip therapeutic for mastitis and liquid to be applied to pet's skin (as in a "body splash").

Veterinary care compositions according to the invention, in addition to one or more essential oil and/or IC together with one or more fruit acid, may further comprise one or (preferably) more than one component selected from the group consisting of emollients, stabilizing agents, thickening agents, humectants, antimicrobial agents, neutralizing agents, surfactants, water, silicone polymers, alcohols, and hydrogels, anti-inflammatory agents, wound healing agents, salicylic acid, as well as additional components as may be known in the art.

Specific, non-limiting examples of additional components which may be comprised in pet care products include the components listed above for personal care products.

In certain non-limiting embodiments of the invention, the compositions may be prepared for teat dip to treat mastitis. A general formulation for teat dip compositions is as follows.

TABLE 44

General formulation for teat dip

| Ingredient | Percentage (w/w) |
| --- | --- |
| anti-irritants | 0.1-5.0% |
| a vehicle containing gelling agent | 0.2-1.0% |
| glycerin | 5-15% |
| water | 50-80% |
| antimicrobial agents consisting of botanicals | 0.2-2%), |
| aliphatic and aromatic alcohols | 0.5-15% |
| alkanediol | 0.3-1% |
| solvents such as vegetable oils | |

The anti-irritants used for teat dip may include but are not limited to zinc salts with panthenol, or Bisabolol with ginger root extract (symrelief), or symrelief with a zinc salt. The gelling agents in the vehicle may include but are not limited to natural gelling agents such as natural gums, starches, pectins, agar and gelatin. Antimicrobial botanicals may include but are not limited to lemongrass oil, orange oil and fruit acids such as citric and lactic acid, phenoxyethanol (constituent of sage oil). The following Tables summarize various non limiting examples of formulations.

TABLE 45

Veterinary Composition 1

| Ingredients | Percentage (w/w) |
| --- | --- |
| Water | 72.14 |
| Xanthum gum | 0.4 |
| Glycerin | 15.0 |
| Zinc gluconate | 0.1 |
| Zinc lactate | 0.1 |
| Zinc acetate | 0.1 |
| Panthenol (75W) | 0.66 |
| Lemon grass oil | 0.3 |
| Orange oil | 0.1 |
| Citric acid | 0.5 |
| Phenoxyethanol | 0.7 |
| Safflower oil | 10.0 | pH adjusted to 5.0 with 10 N NaOH

TABLE 46

Veterinary Composition 2

| Ingredients | Percentage (w/w) |
| --- | --- |
| Water | 71.04 |
| Xanthum gum | 0.5 |
| Glycerin | 15.0 |
| Bisabolol, ginger root extract (symrelief) | 0.2 |
| Panthenol (75W) | 0.66 |
| Lemon grass oil | 0.3 |
| Orange oil | 0.1 |
| Citric acid | 1.0 |
| Phenoxyethanol | 0.7 |
| 1,2 decanediol (symclairol) | 0.5 |
| Safflower oil | 10.0 | pH adjusted to 5.0 with 10 N NaOH

TABLE 47

Veterinary Composition 3

| Ingredients | Percentage (w/w) |
| --- | --- |
| Water | 71.04 |
| Xanthum gum | 0.5 |
| Glycerin | 15.0 |
| Bisabolol, ginger root extract (symrelief) | 0.2 |
| Panthenol (75W) | 0.66 |
| Lemon grass oil | 0.3 |
| Orange oil | 0.1 |
| Lactic acid | 1.0 |
| Phenoxyethanol | 0.7 |
| 1,2 decanediol (symclairol) | 0.5 |
| Fatty acid ester (PCL Liquid 100) | 0.5 |
| Safflower oil | 10.0 |

TABLE 48

Veterinary Composition 4 (teat dip)

| Ingredients | Percentage (w/w) |
| --- | --- |
| Water | 71.7 |
| Xanthum gum | 0.5 |
| DC Silicone Q2 5220 | 0.5 |
| Glycerin | 15.0 |
| Bisabolol, ginger root extract (symrelief) | 0.2 |
| Panthenol (75W) | 0.66 |
| Lemon grass oil | 0.3 |
| Orange oil | 0.1 |
| Citric acid | 1.0 |
| Phenoxyethanol | 0.7 |
| 1,2 decanediol (symclairol) | 0.5 |
| Fatty acid ester (PCL Liquid 100) | 0.5 |
| Safflower oil | 10.0 | pH adjusted to 5.0 with 10 N NaOH

TABLE 49

Veterinary Composition 5 (teat dip)

| Ingredients | Percentage (w/w) |
| --- | --- |
| Water | 71.7 |
| Xanthum gum | 0.5 |
| DC Silicone Q2 5220 | 0.5 |
| Glycerin | 15.0 |
| Bisabolol, ginger root extract (symrelief) | 0.2 |
| Lemon grass oil | 0.3 |
| Orange oil | 0.1 |
| Citric acid | 1.0 |
| Phenoxyethanol | 0.7 |
| 1,2 decanediol (symclairol) | 0.5 |
| Fatty acid ester (PCL Liquid 100) | 0.5 |
| Safflower oil | 10.0 | pH adjusted to 5.0 with 10 N NaOH

4.11 Household/Industrial Products

In a subset of non-limiting embodiments, the present invention provides for household/industrial products comprising a combination of one or more essential oil and/or IC together with one or more fruit acid, as set forth in section 4.6, 4.7, and 4.8, above.

Non-limiting embodiments of household/industrial products which may utilize the invention include householder cleaners such as concentrated liquid cleaners and spray cleaners, cleaning wipes, dish washing liquid, dish washer detergent, spray-mop liquid, furniture polish, indoor paint, outdoor paint, dusting spray, laundry detergent, fabric softener, rug/fabric cleaner, window and glass cleaner, toilet bowl cleaner, liquid/cream cleanser, etc. In a particular embodiment, the invention may be used in a food wash product, designed to clean fruits and vegetables prior to consumption. "Household products" are products, other than personal care products, that would be used by individual consumers. "Industrial products" refers to products that are used in industry.

Household-industrial compositions according to the invention, in addition to one or more essential oil and/or IC together with one or more fruit acid, may further comprise one or (preferably) more than one component selected from the group consisting of surfactants, builders (e.g., sequestering builders, precipitating builders, ion exchange builders), solvents, thickeners, abrasives, acids, bases (alkalis), antimicrobial agents, soaps, bleaching agents, enzymes, preservatives, and sudsing agents, as well as additional components as may be known in the art.

In various non-limiting embodiments of the invention, a household/industrial product comprising a combination of one or more essential oil and/or IC together with one or more fruit acid may further comprise a surfactant, for example, but not limited to, an anionic surfactant such as an alkyl sulfate, an alkyldiphenyloxide disulfonate salt (e.g., the DOWFAX series by the Dow Chemical Company), an alkylbenzenesulfonate, an alcohol ethoxysulfate; a cationic surfactant; a non-ionic surfactant, such as a secondary alcohol ethoxylate (e.g., the TERGITAOL series by the Dow Chemical Company) or an alkyl polyglucoside (e.g., the TRITON series by the Dow Chemical Company); or an amphoteric surfactant such as an imidazoline or betaine compound.

In various non-limiting embodiments of the invention, a household/industrial product comprising a combination of one or more essential oil and/or IC together with one or more fruit acid may further comprise a builder, for example, but not limited to, a sequestering builder (chelating agent) such as ethylenediaminetetraacetic acid ("EDTA"), sodium citrate, or a complex phosphate; an ion exchange builder such as zeolite, or a precipitating builder such as sodium carbonate or sodium silicate.

In various non-limiting embodiments of the invention, a household/industrial product comprising a combination of one or more essential oil and/or IC together with one or more fruit acid may further comprise a solvent, for example, but not limited to, water, an alcohol such as methanol, ethanol, isopropyl alcohol, or butanol; a hydrocarbon such as an aromatic hydrocarbon, propylene glycol, methylene chloride, acetone, a petroleum distillate, and/or a glycol ether.

In various non-limiting embodiments of the invention, a household/industrial product comprising a combination of one or more essential oil and/or IC together with one or more fruit acid may further comprise a thickener, for example, but not limited to, a polyethylene glycol. a methoxypolyethylene glycol, and/or hydroxyethyl cellulose.

In various non-limiting embodiments of the invention, a household/industrial product comprising a combination of one or more essential oil and/or IC together with one or more fruit acid may further comprise an abrasive, such as, but not limited to, silica, feldspar or calcite.

In various non-limiting embodiments of the invention, a household/industrial product comprising a combination of one or more essential oil and/or IC together with one or more fruit acid may further comprise an acid, such as, but not limited to, acetic acid, hydroacetic acid, phosphoric acid or hydrochloric acid.

In various non-limiting embodiments of the invention, a household/industrial product comprising a combination of one or more essential oil and/or IC together with one or more fruit acid may further comprise a base (alkali) such as, but not limited to, ammonia or sodium bicarbonate.

In various non-limiting embodiments of the invention, a household/industrial product comprising a combination of one or more essential oil and/or IC together with one or more fruit acid may further comprise an antimicrobial agent, for example, but not limited to, compounds as set forth above for personal care compositions, and also pine oil and sodium hypochlorite.

In various non-limiting embodiments of the invention, a household/industrial product comprising a combination of one or more essential oil and/or IC together with one or more fruit acid may further comprise a bleaching agent, for example, but not limited to, sodium hypochlorite, hydrogen peroxide, sodium percarbonate and sodium perborate.

In various non-limiting embodiments of the invention, a household/industrial product comprising a combination of one or more essential oil and/or IC together with one or more fruit acid may further comprise an enzyme, such as, but not limited to, a protease or a lipase.

In various non-limiting embodiments of the invention, a household/industrial product comprising a combination of one or more essential oil and/or IC together with one or more fruit acid may further comprise a preservative, such as, but not limited to, butylated hydroxytoluene, glutaraldehyde, and EDTA.

In various non-limiting embodiments of the invention, a household/industrial product comprising a combination of one or more essential oil and/or IC together with one or more fruit acid may further comprise a sudsing agent, such as, but not limited to, diethanolamine or triethanolamine.

In one set of non-limiting embodiments, the present invention provides for surface cleaner compositions comprising (i) one or more EO/IC, preferably where the EO(s)/IC(s) are selected from the group consisting of lemongrass oil and/or an IC thereof; orange oil and/or an IC thereof; cinnamon leaf oil and/or an IC thereof; basil oil and/or an IC thereof; and/or pine oil and/or an IC thereof; at a total concentration of between about 0.1 and 1 percent (weight/weight); (ii) a fruit acid, preferably citric acid, at a concentration of between about 1 and 2 percent (weight/weight); (iii) an alcohol, preferably ethanol, at a concentration of between about 5 and 20 percent (weight/weight); and (iv) optionally triclosan at a concentration of between about 0.05 and 1 percent (weight/weight), where the ratio of EO(s)/IC(s) to fruit acid is between about 1:1 to 1:10 (inclusive) and the pH is between about 3 and about 7, preferably between 3 and 5. In certain non-limiting embodiments of the invention, cinnamon leaf oil or an IC thereof and/or pine oil or an IC thereof is not present.

In specific, non-limiting embodiments, the present invention provides for the following surface cleaners, having concentrations of active ingredients as indicated, as well as concentrated stock solutions of these formulations which may be diluted to achieve the respective concentrations.

TABLE 50

Surface Cleaners

| Surface Cleaner | Active ingredients |
| --- | --- |
| Surface Disinfectant-LG cit 2 | 0.2% Lemon grass oil |
|  | 2% Citric acid |
|  | 7.65% Alcohol |
|  | 0.15% surfactants |
| Surface Disinfectant-LG P cit 4 | 0.3% Pine oil |
|  | 0.1% Lemon grass oil |
|  | 2% Citric Acid |
|  | 7.45% alcohol |
|  | 0.15% Surfactants |
| Surface Disinfectant-P cit 5 | 0.5% Pine oil |
|  | 2% Citric acid |
|  | 7.45% alcohol |
|  | 0.15% surfactants |
| Surface Disinfectant-PO Cit 7 | 0.5% Pine oil |
|  | 0.2% Orange oil |
|  | 1% Citric Acid |
|  | 5.35% alcohol |
|  | 0.15% Surfactants |
| Surface Disinfectant-LGO Cit 7 | 0.5% lemongrass oil |
|  | 0.2% Orange oil |
|  | 1% Citric Acid |
|  | 5.35% alcohol |
|  | 0.15% Surfactants |

TABLE 51

Stock solution of hard surface Disinfectant-LG-O-Cit1 + Dodecanediol:

| Ingredient | Percentage (w/w) |
| --- | --- |
| Lemon Grass oil | 3.0 |
| Orange oil | 1.0 |
| Citric Acid | 10.0 |
| 1,12 Dodecanediol | 5.0 |
| SDA 40B alcohol | 79.5 |
| Pluronic Surfactant L-61 | 0.5 |
| Pluronic Surfactant F-127 | 0.5 |
| Pluronic Surfactant F-87 | 0.5 |

Before use, this solution is diluted 10 fold with water.

TABLE 52

Stock solution of hard surface Disinfectant-LG-O-Cit 2 + Dodecanediol

| Ingredient | Percentage (w/w) |
| --- | --- |
| Lemon Grass oil | 3.0 |
| Orange oil | 1.0 |
| Citric Acid | 20.0 |
| 1,12 Dodecanediol | 5.0 |
| SDA 40B alcohol | 69.5 |
| Pluronic Surfactant L-61 | 0.5 |
| Pluronic Surfactant F-127 | 0.5 |
| Pluronic Surfactant F-87 | 0.5 |

Before use, this solution is diluted 10 fold with water.

The detailed description hereby incorporates, by reference, the specific working examples of the invention set forth below.

The working examples sometimes refer to Softsoap® or Dial® soaps.

Softsoap® is a commercially sold liquid soap comprising water, sodium laureth sulfate, cocamidopropyl betaine, decylglucoside, sodium chloride, fragrance, DMDM hydantoin, PEG-120 methyl glucose dioleate, tetrasodium ethylene diamine tetracetic acid, sodium sulfate, polyquaternium-7, citric acid, poloxamer 124, PEG-7 glyceryl, cocoate, benzophenine-4, and colors.

Dial® soap is a commercially sold liquid soap, where Dial® Antibacterial hand soap comprises, as active agent, 0.15 percent triclosan, and the inactive agents are water, sodium laureth sulfate, ammonium lauryl sulfate, decyl glucoside, cocamidopropyl betaine, glycerine, sodium chloride, PEG-18 gylceryl oleate/cocoate, fragrance, cocamide MEA, DMDM hydantoin, tetrasodium ethylene diamine tetracetic acid and colors.

4.12 Preservative Compositions

In certain non-limiting embodiments of the invention, the compositions may be formulated as preservative compositions to be used alone or in conjunction with personal care, household or veterinary, products for preservation purposes. Such compositions may contain lemongrass oil, orange oil, lactic or citric acid, phenoxyethanol and/or an alkanediol. Alkanediols include but are not limited to 1,2-decanediol, 1,12-dodecanediol, and/or 1,2-octanediol. The ingredients are combined in an appropriate solvent including but not limited to ethanol, butanol, 3-methoxy-3-methyl-1-butanol, or combinations thereof. The pH of these solutions are adjusted to 5.0, with an appropriate buffer, including for example sodium hydroxide (NaOH). 0.5-5.0% of the preservative compositions can be used in various formulations, preferably 2.0-3.0% of the preservative compositions.

One general formulation for preservative compositions (which may optimally be in the form of stock solutions, which may be diluted prior to use) is as follows. For all preservative compositions, pH is adjusted to 5.0.

TABLE 53

General compositions of preservatives

| Ingredient | Composition of stock solution % (w/w) | Composition in products % (w/w) |
| --- | --- | --- |
| Lemongrass oil | 2-25 | 0.04-0.5 |
| Orange oil | 0.5-10 | 0.01-0.1 |
| Lactic acid/Citric acid | 3.3-25 | 0.1-0.5 |
| Phenoxyethanol | 0-40 | 0-1.0 |
| Alkanediols | 0-50 | 0-1.2 |
| 3-methoxy-3-methyl-1-butanol | 0-50 | 0-1.5 |
| SDA 40 B alcohol | 0-70 | 0-2.1 |
| Propylene glycol | 0-50 | 0-1.3 |

Various non-limiting examples of specific preservative formulations follow below.

TABLE 54

Preservative composition A

| Ingredient | Percentage (w/w) |
| --- | --- |
| Lemongrass oil | 10 |
| Farnesol | 10 |
| Orange oil | 5 |
| lactic acid | 7 |
| 1,2 decanediol | 7 |
| SDA 40 B alcohol | 61 |

TABLE 55

Preservative composition B

| Ingredient | Percentage (w/w) |
| --- | --- |
| Lemongrass oil | 15 |
| Farnesol | 15 |
| Orange oil | 10 |
| lactic acid | 10 |
| SDA 40 B alcohol | 50 |

TABLE 56

Preservative composition C

| Ingredient | Percentage (w/w) |
| --- | --- |
| Farnesol | 17 |
| Citric acid | 7 |
| 1,2 decanediol | 7 |
| SDA 40 B alcohol | 69 |

TABLE 57

Preservative composition D

| Ingredient | Percentage (w/w) |
| --- | --- |
| Lemongrass oil | 15 |
| Orange oil | 5 |
| Lactic acid | 10 |
| 1,2 decanediol | 20 |
| 1,2 Octanediol | 20 |
| SDA 40 B alcohol | 30 |

TABLE 58

Preservative composition E

| Ingredient | Percentage (w/w) |
| --- | --- |
| Lemongrass oil | 15 |
| Orange oil | 5 |
| Lactic acid | 10 |
| 1,2 Octanediol | 40 |
| SDA 40 B alcohol | 30 |

Additional specific non-limiting examples of preservative compositions follow below, with the compositions of stock solutions as well as varying percentages of the preservative compositions in products.

TABLE 59

Preservative composition F

| Ingredient | Composition of stock solution % (w/w) | Products containing 2% of preservative % (w/w) |
| --- | --- | --- |
| Lemongrass oil | 25 | 0.5 |
| Orange oil | 5 | 0.1 |
| Lactic acid | 10 | 0.2 |
| Phenoxyethanol | 35 | 0.7 |
| SDA 40 B alcohol | 25 | 0.5 |

TABLE 60

Preservative composition G

| Ingredient | Composition of stock solution % (w/w) | Products containing 3% of preservative % (w/w) |
| --- | --- | --- |
| Lemongrass oil | 10 | 0.3 |
| Orange oil | 3.3 | 0.1 |
| Lactic acid | 6.7 | 0.2 |
| Phenoxyethanol | 23.3 | 0.7 |
| 1,2-decanediol | 16.7 | 0.5 |
| SDA 40 B alcohol | 40 | 1.2 |

TABLE 61

Preservative composition H

| Ingredient | Composition of stock solution % (w/w) | Products containing 3% of preservative % (w/w) |
| --- | --- | --- |
| Lemongrass oil | 10 | 0.3 |
| Orange oil | 3.3 | 0.1 |
| Lactic acid | 6.7 | 0.2 |
| Phenoxyethanol | 23.3 | 0.7 |
| 1,12-dodecanediol | 16.7 | 0.5 |
| 3-methoxy-3-methyl-1-butanol | 40 | 1.2 |

TABLE 62

Preservative composition I

| Ingredient | Composition of stock solution % (w/w) | Products containing 3% of preservative % (w/w) |
| --- | --- | --- |
| Lemongrass oil | 16.7 | 0.5 |
| Orange oil | 3.3 | 0.1 |
| Lactic acid | 6.7 | 0.2 |
| Phenoxyethanol | 23.3 | 0.7 |
| 1,12-dodecanediol | 16.7 | 0.5 |
| 3-methoxy-3-methyl-1-butanol | 33.3 | 1.0 |

TABLE 63

Preservative composition J

| Ingredient | Composition of stock solution % (w/w) | Products containing 2.5% of preservative % (w/w) |
| --- | --- | --- |
| Lemongrass oil | 16.7 | 0.5 |
| Orange oil | 3.3 | 0.1 |
| Lactic acid | 6.7 | 0.2 |
| 1,12-dodecanediol | 33.3 | 0.5 |
| 3-methoxy-3-methyl-1-butanol | 40 | 1.2 |

TABLE 64

Preservative composition K

| Ingredient | Composition of stock solution % (w/w) | Products containing 2.5% of preservative % (w/w) |
| --- | --- | --- |
| Lemongrass oil | 20 | 0.5 |
| Orange oil | 4 | 0.1 |
| Lactic acid | 8 | 0.2 |
| Octanediol | 40 | 1.0 |
| SDA 40 B | 28 | 0.7 |

TABLE 65

Preservative composition L

| Ingredient | Composition of stock solution % (w/w) | Products containing 3% of preservative % (w/w) |
| --- | --- | --- |
| Lemongrass oil | 16.7 | 0.5 |
| Orange oil | 3.3 | 0.1 |
| Lactic acid | 6.7 | 0.2 |
| 1,12-decanediol | 33.3 | 1.0 |
| SDA 40 B | 40.0 | 1.2 |

TABLE 66

Preservative composition M

| Ingredient | Composition of stock solution % (w/w) | Products containing 3% of preservative % (w/w) |
| --- | --- | --- |
| Lemongrass oil | 10 | 0.3 |
| Orange oil | 3.3 | 0.1 |
| Farnesol | 10 | 0.3 |
| Lactic acid | 6.7 | 0.2 |
| Phenoxyethanol | 20 | 0.6 |
| 1,12-dodecanediol | 16.7 | 0.5 |
| 3-methoxy-3-methyl-1-butanol | 33.3 | 1.0 |

TABLE 67

Preservative composition N

| Ingredient | Composition of stock solution % (w/w) | Products containing 2% of preservative % (w/w) |
|---|---|---|
| Lemongrass oil | 25 | 0.5 |
| Orange oil | 5 | 0.1 |
| Citric acid | 25 | 0.5 |
| SDA 40 B | 45 | 0.9 |

TABLE 68

Preservative composition O

| Ingredient | Composition of stock solution % (w/w) | Products containing 2.5% of preservative % (w/w) |
|---|---|---|
| Lemongrass oil | 20 | 0.5 |
| Orange oil | 4.0 | 0.1 |
| Citric acid | 20 | 0.5 |
| Phenoxyethanol | 28 | 0.7 |
| SDA 40 B | 28 | 0.7 |

TABLE 69

Preservative composition P

| Ingredient | Composition of stock solution % (w/w) | Products containing 2.5% of preservative % (w/w) |
|---|---|---|
| Lemongrass oil | 20 | 0.5 |
| Orange oil | 4.0 | 0.1 |
| Citric acid | 20 | 0.5 |
| 1,2-octanediol | 28 | 0.7 |
| SDA 40 B | 28 | 0.7 |

TABLE 70

Preservative composition Q

| Ingredient | Composition of stock solution % (w/w) | Products containing 2.5% of preservative % (w/w) |
|---|---|---|
| Lemongrass oil | 20 | 0.5 |
| Orange oil | 4.0 | 0.1 |
| Citric acid | 20 | 0.5 |
| 1,2-decanediol | 28 | 0.7 |
| SDA 40 B | 28 | 0.7 |

TABLE 71

Preservative composition - 1

| Ingredients | Stock (% w/w) | Products containing 1.75% stock (% w/w) |
|---|---|---|
| Lemongrass oil | 5.6 | 0.1 |
| Orange oil | 2.8 | 0.05 |
| Lactic acid | 11.4 | 0.2 |
| Octanediol | 40 | 0.7 |
| Phenoxyethanol | 40 | 0.7 |
| (pH of Stock solution 5.0) | | |

TABLE 72

Preservative composition - 2

| Ingredients | Stock (% w/w) | Products containing 2.0% stock (% w/w) |
|---|---|---|
| Lemongrass oil | 3.75 | 0.075 |
| Orange oil | 1.25 | 0.025 |
| Lactic acid | 15 | 0.3 |
| Octanediol | 40 | 0.8 |
| Phenoxyethanol | 40 | 0.8 |
| (pH of Stock solution 5.0) | | |

TABLE 73

Preservative composition - 3

| Ingredients | Stock (% w/w) | Products containing 2.0% stock (% w/w) |
|---|---|---|
| Lemongrass oil | 2.0 | 0.04 |
| Orange oil | 0.5 | 0.01 |
| Lactic acid | 10 | 0.2 |
| Octanediol | 60 | 1.2 |
| Phenoxyethanol | 27.5 | 0.55 |
| (pH of Stock solution 5.0) | | |

TABLE 74

Preservative composition - 4

| Ingredients | Stock (% w/w) | Products containing 2.0% stock (% w/w) |
|---|---|---|
| Lemongrass oil | 5 | 0.1 |
| Orange oil | 2.5 | 0.05 |
| Lactic acid | 10 | 0.2 |
| Octanediol | 40 | 0.8 |
| Propylene glycol | 42.5 | 0.85 |
| (pH of Stock solution 5.0) | | |

TABLE 75

Preservative composition - 5

| Ingredients | Stock (% w/w) | Products containing 2.0% stock (% w/w) |
|---|---|---|
| Lemongrass oil | 5 | 0.1 |
| Orange oil | 2.5 | 0.05 |
| Lactic acid | 10 | 0.2 |
| Octanediol | 50 | 1.0 |
| Propylene glycol | 32.5 | 0.65 |
| (pH of Stock solution 5.0) | | |

TABLE 76

Preservative composition - 6

| Ingredients | Stock (% w/w) | Products containing 2.0% stock (% w/w) |
|---|---|---|
| Lemongrass oil | 3.75 | 0.075 |
| Orange oil | 1.25 | 0.025 |
| Lactic acid | 10 | 0.2 |
| Octanediol | 50 | 1.0 |
| Propylene glycol | 35 | 0.7 |
| (pH of Stock solution 5.0) | | |

TABLE 77

Preservative composition - 7

| Ingredients | Stock (% w/w) | Products containing 2.0% stock (% w/w) |
|---|---|---|
| Lemongrass oil | 2.5 | 0.05 |
| Orange oil | 1.25 | 0.025 |
| Lactic acid | 10 | 0.2 |
| Octanediol | 50 | 1.0 |
| Propylene glycol | 36.25 | 0.725 |
| (pH of Stock solution 5.0) | | |

TABLE 78

Preservative composition - 7-A

| Ingredients | Stock (% w/w) | Products containing 2.0% stock (% w/w) |
|---|---|---|
| Lemongrass oil | 2.0 | 0.05 |
| Orange oil | 1.0 | 0.025 |
| Lactic acid | 8.0 | 0.2 |
| Octanediol | 40 | 1.0 |
| Propylene glycol | 49 | 1.225 |
| (pH of Stock solution 5.0) | | |

TABLE 79

Preservative composition - 7-B-L

| Ingredients | Stock (% w/w) | Products containing 2.5% stock (% w/w) |
|---|---|---|
| Lemongrass oil | 2.8 | 0.07 |
| Lactic acid | 8.0 | 0.2 |
| Octanediol | 40 | 1.0 |
| Propylene glycol | 49.2 | 1.23 |
| (pH of Stock solution 5.0) | | |

TABLE 80

Preservative composition - 7-B-M

| Ingredients | Stock (% w/w) | Products containing 2.5% stock (% w/w) |
|---|---|---|
| Lemongrass oil | 2.8 | 0.07 |
| Multifruit BSC | 8.0 | 0.2 |
| *Mixture of lactic, citric, tartaric, glycolic, malic acid extracted from plants (obtained from Arch Chemicals) | | |
| Octanediol | 40 | 1.0 |
| Propylene glycol | 49.2 | 1.23 |
| (pH of Stock solution 5.0) | | |

The following Tables provide the formulations of specific preservative compositions containing grapefruit seed extract and grape seed extract.

TABLE 81

Preservative composition - G-8

| Ingredients | Stock (% w/w) | Products containing 2.0% stock (% w/w) |
|---|---|---|
| Grapefruit seed extract | 10 | 0.2 |
| Lactic acid | 10 | 0.2 |
| Octanediol | 50 | 1.0 |
| Propylene glycol | 30 | 0.6 |
| (pH of Stock solution 5.0) | | |

TABLE 82

Preservative composition - G-9

| Ingredients | Stock (% w/w) | Products containing 2.0% stock (% w/w) |
|---|---|---|
| Grapefruit seed extract | 10 | 0.2 |
| Lactic acid | 10 | 0.2 |
| Octanediol | 50 | 1.0 |
| Safflower oil | 30 | 0.6 |
| (pH of Stock solution 5.0) | | |

TABLE 83

Preservative composition - G-10

| Ingredients | Stock (% w/w) | Products containing 2.0% stock (% w/w) |
|---|---|---|
| Lemongrass oil | 2.5 | 0.05 |
| Orange oil | 1.25 | 0.025 |
| Grape seed Extract | 10 | 0.2 |
| Lactic acid | 10 | 0.2 |
| Octanediol | 50 | 1.0 |
| Propylene glycol | 26.25 | 0.525 |
| (pH of Stock solution 5.0) | | |

TABLE 84

Preservative composition - G-10-A

| Ingredients | Stock (% w/w) | Products containing 2.5% stock (% w/w) |
|---|---|---|
| Lemongrass oil | 2.0 | 0.05 |
| Grape seed Extract | 8.0 | 0.2 |
| Lactic acid | 8.0 | 0.2 |
| Octanediol | 40 | 1.0 |
| Propylene glycol | 42.0 | 1.05 |
| (pH of Stock solution 5.0) | | |

TABLE 85

Preservative composition - G-10-M

| Ingredients | Stock (% w/w) | Products containing 2.0% stock (% w/w) |
|---|---|---|
| Lemongrass oil | 2.5 | 0.05 |
| Orange Oil | 1.25 | 0.025 |
| Grape seed Extract | 10 | 0.2 |
| Multifruit BSC | 10 | 0.2 |
| *Mixture of lactic, citric, tartaric, glycolic, malic acid extracted from plants(obtained from Arch Chemicals) | | |
| Octanediol | 50 | 1.0 |
| Propylene glycol | 26.25 | 0.525 |
| (pH of Stock solution 5.0) | | |

TABLE 86

Preservative composition -G-10-C

| Ingredients | Stock (% w/w) | Products containing 2.0% stock (% w/w) |
|---|---|---|
| Lemongrass oil | 2.5 | 0.05 |
| Orange Oil | 1.25 | 0.025 |
| Grape seed Extract | 10 | 0.2 |
| Citric acid | 10 | 0.2 |
| Octanediol | 50 | 1.0 |
| Propylene glycol | 26.25 | 0.525 |
| (pH of Stock solution 5.0) | | |

TABLE 87

Preservative composition -G-11

| Ingredients | Stock (% w/w) | Products containing 2.0% stock (% w/w) |
|---|---|---|
| Lemongrass oil | 3.75 | 0.075 |
| Orange Oil | 1.25 | 0.025 |
| Grape seed Extract | 10 | 0.2 |
| Lactic Acid | 10 | 0.2 |
| Octanediol | 50 | 1.0 |
| Propylene glycol | 25 | 0.5 |
| (pH of Stock solution 5.0) | | |

TABLE 88

Preservative composition -G-12

| Ingredients | Stock (% w/w) | Products containing 2.0% stock (% w/w) |
|---|---|---|
| Grape seed Extract | 15 | 0.3 |
| Lactic acid | 10 | 0.2 |
| Octanediol | 50 | 1.0 |
| Propylene glycol | 25 | 0.5 |
| (pH of Stock solution 5.0) | | |

TABLE 89

Preservative composition -G-13

| Ingredients | Stock (% w/w) | Products containing 2.5% stock (% w/w) |
|---|---|---|
| Lemongrass oil | 12 | 0.3 |
| Orange Oil | 4 | 0.1 |
| Grape seed Extract | 8.0 | 0.2 |
| Lactic Acid | 8.0 | 0.2 |
| Octanediol | 40 | 1.0 |
| Propylene glycol | 28 | 0.7 |
| (pH of Stock solution 5.0) | | |

TABLE 90

Preservative composition -G-14

| Ingredients | Stock (% w/w) | Products containing 2.5% stock (% w/w) |
|---|---|---|
| Lemongrass oil | 0.8 | 0.02 |
| Orange Oil | 0.4 | 0.01 |
| Grape seed Extract | 12 | 0.3 |
| Lactic Acid | 8.0 | 0.2 |
| Octanediol | 40 | 1.0 |
| Propylene glycol | 38.8 | 0.97 |
| (pH of Stock solution 5.0) | | |

TABLE 91

Preservative composition -G-15

| Ingredients | Stock (% w/w) | Products containing 2.5% stock (% w/w) |
|---|---|---|
| Lemongrass oil | 2.8 | 0.07 |
| Grape seed Extract | 8.0 | 0.2 |
| Lactic acid | 8.0 | 0.2 |
| Octanediol | 40 | 1.0 |
| Propylene glycol | 41.2 | 1.03 |
| (pH of Stock solution 5.0) | | |

TABLE 92

Preservative composition -G-16

| Ingredients | Stock (% w/w) | Products containing 2.5% stock (% w/w) |
|---|---|---|
| Lemongrass oil | 2.8 | 0.07 |
| Grape seed Extract | 8.0 | 0.2 |
| Lactic Acid | 8.0 | 0.2 |
| Octanediol | 28 | 0.7 |
| Propylene glycol | 53.2 | 1.33 |
| (pH of Stock solution 5.0) | | |

TABLE 93

Preservative composition -G-17

| Ingredients | Stock (% w/w) | Products containing 2.5% stock (% w/w) |
|---|---|---|
| Lemongrass oil | 2.8 | 0.07 |
| Grape seed Extract | 8 | 0.2 |
| Lactic Acid | 8 | 0.2 |
| Octanediol | 40 | 1.0 |
| Propylene glycol | 41.2 | 1.03 |
| (pH of Stock solution 5.0) | | |

The following Tables provide the formulations of specific preservative compositions containing essential oils/botanical extracts, fruit acids and alkanediol without solvents. All of the compositions ending in "L" are noted as the L series, which contain lactic acid. All of the compositions ending in "M" are noted as the M series, which contain Multifruit®BSC. Multifruit®BSC contains a mixture of lactic, citric, tartaric, glycolic, and malic acid extracted from plants (obtained from Arch Chemicals). The pH of all the preservative compositions in the following Tables were adjusted to 5.0 with 10 N. NaoH (30-70 ul/ml were required). The preservative formulations can be incorporated into various applications, including, for example, personal care products.

TABLE 94

Preservative composition -6-L

| Ingredients | Stock (% w/w) | Cream containing 1.3% stock |
|---|---|---|
| Lemongrass oil | 5.78 | 0.075 |
| Orange oil | 1.92 | 0.025 |
| Lactic Acid | 15.4 | 0.2 |
| Octanediol | 76.9 | 1.0 |

TABLE 95

Preservative composition -6-M

| Ingredients | Stock (% w/w) | Cream containing 1.3% stock |
|---|---|---|
| Lemongrass oil | 5.78 | 0.075 |
| Orange oil | 1.92 | 0.025 |
| Multifruit extract | 15.4 | 0.2 |
| Octanediol | 76.9 | 1.0 |

TABLE 96

Preservative composition -10-G-L

| Ingredients | Stock (% w/w) | Cream containing 1.5% stock |
|---|---|---|
| Lemongrass oil | 3.3 | 0.05 |
| Orange oil | 1.6 | 0.025 |
| Grapefruit seed extract | 15.0 | 0.225 |
| Lactic Acid | 13.3 | 0.2 |
| Octanediol | 66.8 | 1.0 |

TABLE 97

Preservative composition -10-G-M

| Ingredients | Stock (% w/w) | Cream containing 1.5% stock |
|---|---|---|
| Lemongrass oil | 3.3 | 0.05 |
| Orange oil | 1.6 | 0.025 |
| Grapefruit seed extract | 15 | 0.225 |
| Multifruit BSC Mixture of lactic, citric, tartaric, glycolic, malic acid extracted from plants (obtained from Arch Chemicals) | 13.3 | 0.2 |
| Octanediol | 66.8 | 1.0 |

TABLE 98

Preservative composition - 11-G-L

| Ingredients | Stock (% w/w) | Cream containing 1.5% stock |
|---|---|---|
| Lemongrass oil | 5.0 | 0.075 |
| Orange oil | 1.7 | 0.025 |
| Grapefruit seed extract | 13.3 | 0.2 |
| Lactic Acid | 13.3 | 0.2 |
| Octanediol | 66.7 | 1.0 |

TABLE 99

Preservative composition - 11-G-M

| Ingredients | Stock (% w/w) | Cream containing 1.5% stock |
|---|---|---|
| Lemongrass oil | 5.0 | 0.075 |
| Orange oil | 1.7 | 0.025 |
| Grapefruit seed extract | 13.3 | 0.2 |
| Multifruit BSC Mixture of lactic, citric, tartaric, glycolic, malic acid extracted from plants (obtained from Arch Chemicals) | 13.3 | 0.2 |
| Octanediol | 66.7 | 1.0 |

TABLE 100

Preservative composition - G-17-G

| Ingredients | Stock (% w/w) | Cream containing 2.5% stock |
|---|---|---|
| Lemongrass oil | 2.8 | 0.07 |
| Grapefruit seed extract | 8.0 | 0.2 |
| Lactic acid | 8.0 | 0.2 |
| Octanediol | 40 | 1.0 |
| Glycerine | 41.2 | 1.03 |

TABLE 101

Preservative composition - G-18-G

| Ingredients | Composition of Stock Solution (% w/w) | Cream containing 1.5% stock |
|---|---|---|
| Lemongrass oil | 4.67 | 0.07 |
| Grapefruit seed extract | 13.33 | 0.2 |
| Lactic acid | 13.33 | 0.2 |
| Octanediol | 46.67 | 0.7 |
| Glycerine | 22.0 | 0.33 | pH of stock solution is 5.0

TABLE 102

Preservative composition - G-18

| Ingredients | Composition of Stock Solution (% w/w) | Cream containing 1.5% stock |
|---|---|---|
| Lemongrass oil | 4.67 | 0.07 |
| Grapefruit seed extract | 13.33 | 0.2 |
| Lactic acid | 13.33 | 0.2 |
| Octanediol | 46.67 | 0.7 |
| Propylene glycol | 22.0 | 0.33 |

TABLE 103

Preservative composition - G-19-G

| Ingredients | Composition of Stock Solution (% w/w) | Cream containing 1.5% stock |
|---|---|---|
| Lemongrass oil | 4.67 | 0.07 |
| Grapefruit seed extract | 13.33 | 0.2 |
| Lactic acid | 13.33 | 0.2 |
| Octanediol | 46.67 | 0.5 |
| Glycerine | 22.0 | 0.53 |

TABLE 104a

Preservative composition - G-19

| Ingredients | Composition of Stock Solution (% w/w) | Cream containing 1.5% stock |
|---|---|---|
| Lemongrass oil | 4.67 | 0.07 |
| Grapefruit seed extract | 13.33 | 0.2 |
| Lactic acid | 13.33 | 0.2 |
| Octanediol | 46.67 | 0.5 |
| Propylene glycol | 22.0 | 0.53 | pH of stock solution is 5.0

TABLE 104b

Preservative composition V-1

| Ingredients | Composition of Stock Solution (% w/w) | Cream containing 2.0% stock |
|---|---|---|
| Lemongrass oil | 5.0 | 0.1 |
| Grapefruit seed extract | 10.0 | 0.2 |
| Lactic acid | 10.0 | 0.2 |
| Octanediol | 25.0 | 0.5 |
| Glycerine | 50.0 | 1.0 |

TABLE 104c

Preservative composition V-3

| Ingredients | Composition of Stock Solution (% w/w) | Cream containing 2.0% stock |
|---|---|---|
| Lemongrass oil | 5.0 | 0.1 |
| Grapefruit seed extract | 5.0 | 0.1 |
| Lactic acid | 10.0 | 0.2 |
| Octanediol | 25.0 | 0.5 |
| Glycerine | 55.0 | 1.1 |

TABLE 104d

Preservative composition V-8

| Ingredients | Composition of Stock Solution (% w/w) | Cream containing 1.5% stock |
|---|---|---|
| Lemongrass oil | 6.67 | 0.1 |
| Grapefruit seed extract | 6.67 | 0.1 |
| Lactic acid | 13.33 | 0.2 |
| Octanediol | 20.0 | 0.3 |
| Glycerine | 33.33 | 0.5 |
| Zemea | 20.0 | 0.3 |

5. EXAMPLES

Example 1

Various concentrations of basil oil and acetic, lactic, and citric acids, separately and in combination, were prepared in 10 percent SDA40-B alcohol and water, and adjusted to 100 percent. Except for citric acid, which was added by weight, all other ingredients were measured by volume. 0.9 ml of each solution were dispensed in sterile culture tubes, in triplicate, and 0.1 ml of a $10^7$ cfu/ml S. aureus culture was added to the tubes, vortexed, and then, five minutes later, 9.0 ml of drug inactivating medium was added to each tube. Serial dilutions were made with the drug inactivating medium. 0.5 ml of the dilutions were plated on trypticase soy agar ("TSA") plates. As a control, water containing 10 percent SDA40-B alcohol was processed in parallel. The plates were incubated at 37° C. for 24-48 hours and then the colony counts were determined. The results are shown in Table 105. The greater synergy was observed between basil oil and citric acid ("CA").

TABLE 105

| Compounds | $Log_{10}$ Reduction* |
|---|---|
| 1% Basil oil | 2.7 |
| 0.5% Basil oil | 1.8 |
| 1% Acetic acid (AA) | 0.2 |
| 1% Lactic acid (LA) | 2.3 |
| 1% Citric Acid (CA) | 0.1 |
| 1% Basil oil + 1% LA | 5.4 |
| 1% Basil oil + 1% AA | 3.4 |
| 1% Basil oil + 1% CA | 5.1 |
| 0.5% Basil oil + 1% CA | 5.1 |
| 0.5% Basil oil + 0.5% CA | 5.0 |
| 0.25% Basil oil + 1% CA | 5.0 |
| 0.25% Basil oil + 0.5% CA | 2.5 |

*$Log_{10}$ reduction from control bacterial counts ranging from $1 \times 10^6$ to $5 \times 10^6$.

The same methodology was used to test the antimicrobial activity of combinations of citric acid with other essential oils. The results are shown in Table 106. In these experiments, cinnamon oil and citronella oil exhibited superior antimicrobial activities in combination with citric acid.

TABLE 106

| Compounds | $Log_{10}$ Reduction* |
|---|---|
| 1% CA | 0.1 |
| 0.5% Cinnamon bark | 2.4 |
| 0.25% Cinnamon bark | 1.1 |
| 0.5% Cinnamon bark + 1% CA | 5.9 |
| 0.25% Cinnamon bark + 1% CA | 4.3 |
| 0.125% Cinnamon bark + 1% CA | 2.6 |
| 0.25% Cinnamon leaf | 2.8 |
| 0.25% Cinnamon leaf + 1% CA | 5.7 |
| 0.125% Citronella oil | 1.3 |
| 0.25% Citronella oil + 1% CA | 6.2 |
| 0.125% Citronella oil + 1% CA | 3.3 |
| 0.25% Orange oil | 0 |
| 0.25% Orange oil + 1% CA | 2.3 |
| 0.25% Lemon oil | 0.05 |
| 0.25% Lemon oil + 1% CA | 3.3 |
| 0.25% Lavender oil | 0.25 |
| 0.25% Lavender oil + 1% CA | 4.0 |
| 0.25% Clove oil | 0.1 |
| 0.25% Clove oil + 1% CA | 3.3 |
| 0.25% Tea tree oil | 0 |
| 0.25% Tea tree + 1% CA | 4.7 |
| 0.25% Farnesol | 0 |
| 0.25% Farnesol + 1% CA | 4.0 |

*$Log_{10}$ reduction from control bacterial counts ranging from $1 \times 10^6$ to $5 \times 10^6$.

Next, the same general protocol was used to test the efficacy of basil, cinnamon and citronella oils against a variety of organisms, namely E. coli, P. aeruginosa, MRSA, C. albicans, and S. aureus. The results, which demonstrates that in these experiments, combinations of cinnamon oil and citric acid exhibited superior antimicrobial action, are shown in Table 107.

TABLE 107

| Compounds | Log$_{10}$ Reductions* | | | | |
|---|---|---|---|---|---|
| | E. coli | P. aeruginosa | MRSA | C. albicans | S. aureus |
| 0.25% Basil oil + 1% CA | 6.0 | 5.5 | 5.2 | 1.5 | 5.0 |
| 0.25% Cinnamon bark oil + 1% CA | 6.0 | 6.0 | 5.2 | 4.5 | 4.3 |
| 0.25% Citronella oil + 1% CA | 6.4 | 6.4 | 6.5 | 1.0 | 6.3 |
| 0.25% Cinnamon leaf oil + 1% CA | 6.4 | 6.4 | 6.5 | 5.4 | 6.3 |
| 0.25% Eugenol + 1% CA | — | 6.5 | — | 5.5 | — |

*Log$_{10}$ reduction from control bacteria counts ranging from $1 \times 10^6$ to $5 \times 10^6$ or C. albicans ranging from $1 \times 10^5$ to $5 \times 10^5$.

Example 2

The following experiments were performed to evaluate the effectiveness of a hard surface cleaner composition comprising cinnamon leaf oil and citric acid.

Two stock solutions of a hard surface cleaner/disinfectant was prepared, with the following ingredients (the two solutions contained different amounts of cinnamon leaf oil, and therefore the amount of alcohol to bring the solution to 100% also varied).

TABLE 108

| Ingredient | Percentage (w/w) |
|---|---|
| Cinnamon leaf oil | 3.6 or 7.2% |
| Citric acid | 14.3% |
| SDA 40B alcohol | 77.2 or 75.49% (to bring the volume to 100%) |
| Pluronic surfactant L-61 | 0.7% |
| Pluronic surfactant F-127 | 0.7% |
| Pluronic surfactant F-87 | 0.7% |
| Orange oil | 2.8% |

7% of the stock hard disinfectant was diluted with water to 100%.

0.1 ml of culture containing approximately $1 \times 10^7$ colony forming units ("cfu") per milliliter was spread evenly on the surface of $2.5 \times 11$ cm$^2$ tiles using a glass rod and left at room temperature for 10 minutes to dry. After 10 minutes 0.3 ml of the diluted surface disinfectant was spread evenly on the tiles with a sterile glass rod and left for another 10 minutes to dry. The tiles were rinsed with 9.6 ml of inactivating medium (BPBNS), which was collected for testing. The collected medium was serially diluted and 0.5 ml was plated onto TSA plates and incubated at 37° C. for 18-24 hours. The colonies on the plates were counted and the values converted to log$_{10}$. Commercially available Pinesol®, which contains pine oil, was used as a basis for comparison. Pinesol® containing 15% pine oil was diluted with water as per the manufacturer's instructions to a final concentration of 0.9% pine oil. The results are shown in Table 109. The results show that the composition comprising 0.5% cinnamon leaf oil and 1% citric acid exhibited greater antimicrobial activity than the pine oil cleaner against 4 out of 5 microbes tested.

TABLE 109

| Organism | Log$_{10}$ Reductions* | | |
|---|---|---|---|
| | 0.25% cinn. oil + 1% CA | 0.5% cinn. oil + 1% CA | 0.1% Pinesol ® |
| E. coli | 5.3 | 5.3 | 5.7 |
| P. aeruginosa | 6.1 | 6.1 | 3.9 |

TABLE 109-continued

| Organism | Log$_{10}$ Reductions* | | |
|---|---|---|---|
| | 0.25% cinn. oil + 1% CA | 0.5% cinn. oil + 1% CA | 0.1% Pinesol ® |
| MRSA | 2.3 | 3.4 | 2.2 |
| C. albicans | 2.5 | 5.2 | 2.1 |
| S. aureus | 3.7 | 4.1 | 2.4 |

*Log$_{10}$ reduction from control bacterial counts (ranges from $1 \times 10^6$-$5 \times 10^6$ for all bacteria, but for C. albicans counts were $1 \times 10^5$-$5 \times 10^5$.

Example 3

Various concentrations of cinnamon leaf oil and citric acid were dissolved in SDA 40-B alcohol (10%) and water, and adjusted to 100 percent. Except for citric acid, which was added by weight, all other ingredients were measured by volume. 0.9 ml of each solution were dispensed in sterile culture tubes, in triplicate, and 0.1 ml of $10^7$ cfu/ml of S. aureus culture was added to the tubes, vortexed, and then, five minutes later, 9.0 ml of drug inactivating medium was added to each tube. Serial dilutions were made with the drug inactivating medium. 0.5 ml of the dilutions were plated on trypticase soy agar ("TSA") plates. As a control, water containing 10% percent SDA40-B alcohol was processed in parallel. The plates were incubated at 37° C. for 24-48 hours and then the colony counts were determined. The results are shown in Table 110.

TABLE 110

| Compounds | Log$_{10}$ reduction |
|---|---|
| Citric Acid 2% | 0.32 |
| Citric Acid 1.0% | 0.30 |
| Citric Acid 0.5% | 0.20 |
| Citric Acid 0.25% | 0.08 |
| Citric Acid 0.125% | 0.02 |
| Cinnamon leaf oil 0.25% | 0.52 |
| Cinnamon leaf oil 0.5% | 0.55 |
| 0.25% Cinnamon + 0.25% CA | 0.73 |
| 0.25% Cinnamon + 0.5% CA | 3.0 |
| 0.25% Cinnamon + 1.0% CA | 5.6 |
| 0.5% Cinnamon + 0.125% CA | 0.84 |
| 0.5% Cinnamon + 0.25% CA | 2.2 |
| 0.5% Cinnamon + 0.5% CA | 3.2 |
| 0.5% Cinnamon + 1.0% CA | 6.5 |
| 0.5% Cinnamon + 2.0% CA | 6.7 |

Example 4

A liquid soap, called "CN1-A" containing cinnamon oil and citric acid was prepared, having the following composition.

TABLE 111

| Ingredient | Percentage (w/w) |
| --- | --- |
| Deionized water | 59.15% |
| Polyox N 60K | 0.2% |
| Pluronic F 87 Prill | 2.0% |
| Ucare Jr 30 | 0.4% |
| D,L Panthenol 50 W | 1.0% |
| Incromide oxide L | 3.0% |
| Crosultane C-50 | 3.0% |
| Montalene C 40 | 3.0% |
| 2-Phenoxy-ethanol | 1.0% |
| Glycerine | 2.0% |
| SDA-40B alcohol | 15.5% |
| Cinnamon leaf oil | 0.5% |
| Citric acid | 1.0% |
| Orange oil | 0.2% |
| Distilled water | 7.95% |

To prepare the soap, cinnamon oil orange oil, citric acid, and phenoxyethanol are dissolved in the alcohol, the remaining ingredients are dissolved in/mixed with water, and then the alcohol and water solutions are mixed. The pH of the mixture was then adjusted to between 5.5 and 6.5 with 0.1 N NaOH.

The antimicrobial activity of the above soap was tested in parallel with commercial Softsoap® containing triclosan (Softsoap® Antibacterial; Colgate-Palmolive). 0.1 ml of a $10^8$ cfu/ml culture of each microbe tested was mixed with 0.1 ml of bovine serum and placed in a sterile culture tube. 0.8 ml of the test soap formulation was added to the tube and vortexed for 30 seconds. Then 9.0 ml DNB was added to neutralize the activity of the soap. The tube was then vortexed and serially diluted with DNB. 0.5 ml of the diluted solution was plated on TSA plates. The same soap base lacking cinnamon oil, citric acid, and orange oil, with phosphate buffered saline mixed with the culture, were used as the controls. The results are shown in Table 112.

TABLE 112

| | $Log_{10}$ reduction from control* | |
| --- | --- | --- |
| Organisms | CN-1A | Softsoap ®(0.15% TC) |
| S. aureus | 2.0 | 0.33 |
| P. aeruginosa | 2.5 | 0.6 |
| E. coli | 4.86 | 0.5 |
| MRSA | 2.7 | 0.8 |
| C. albicans | 1.43 | 0.0 |

*$log_{10}$ reduction from control microbe counts which in all cases ranged from $1 \times 10^7$-$5 \times 10^7$.

Example 5

A liquid soap, called "CN1-B" containing cinnamon oil and citric acid was prepared, having the following composition.

TABLE 113

| Ingredient | Percentage (w/w) |
| --- | --- |
| Deionized water | 63.2% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |

TABLE 113-continued

| Ingredient | Percentage (w/w) |
| --- | --- |
| Glycerine | 2.0% |
| SDA-40B alcohol | 15.5% |
| Cinnamon leaf oil | 0.5% |
| Citric acid | 1.0% |
| Orange oil | 0.2% |
| Distilled water | 7.8% |

To prepare the soap, cinnamon oil orange oil, citric acid, and phenoxyethanol are dissolved in the alcohol, the remaining ingredients are dissolved in/mixed with water, and then the alcohol and water solutions are mixed. The pH of the mixture was then adjusted to between 5.5 and 6.5 with 0.1 N NaOH.

The antimicrobial activity of the above soap was tested in parallel with commercial Dial® Antibacterial Hand Soap) containing triclosan. 0.1 ml of a $10^8$ cfu/ml culture of each microbe tested was mixed with 0.1 ml of bovine serum and placed in a sterile culture tube. 0.8 ml of the test soap formulation was added to the tube and vortexed for 30 seconds. Then 9.0 ml DNB was added to neutralize the activity of the soap. The tube was then vortexed and serially diluted with DNB. 0.5 ml of the diluted solution was plated on TSA plates. The same soap base lacking cinnamon oil, citric acid, and orange oil, with phosphate buffered saline mixed with the culture, were used as the controls. The results are shown in Table 114.

TABLE 114

| | $Log_{10}$ reduction from control* | |
| --- | --- | --- |
| Organisms | CN1-B | Dial ® soap (0.15% TC) |
| S. aureus | 5.0 | 0.36 |
| MRSA | 5.1 | 0.03 |
| E. coli | 4.45 | 0 |
| P aeruginosa | 5.9 | 0.12 |

*$log_{10}$ reduction from control microbe counts which in all cases ranged from $1 \times 10^7$ to $5 \times 10^7$ $3.4 \times 10^6$ for S. aureus, $3\text{-}5 \times 10^6$ for E. coli and $6 \times 10^5$-$1.3 \times 10^6$ for MRSA.

Example 6

The effectiveness of Softsoap® Juicy Melon (Colgate-Palmolive) with added cinnamon oil, citric acid, and/or triclosan, against MRSA was evaluated. Testing was performed essentially as set forth in the preceding example. The results are shown in Table 115.

TABLE 115

| Compounds | $Log_{10}$ reduction* |
| --- | --- |
| Soft Soap ® + 1.5% cin-cit | 3.63 |
| Soft soap ® + 0.075% TC | 0.15 |
| Soft soap ® + 0.15% TC | 0.20 |
| Soft soap ® + 0.3% TC | 0.58 |
| Soft soap ® + 0.075% TC + 1.5% Cin-Cit | 4.29 |
| Soft soap ® + 0.15% TC + 1.5% Cin-Cit | 4.87 |
| Soft soap ® + 0.3% TC + 1.5% Cin-Cit | 6.38 |

*$log_{10}$ reduction from control microbe counts which in all cases ranged from $1 \times 10^6$-$5 \times 10^6$.

Example 7

The ability of cinnamon oil and citric acid to potentiate the activity of commercial triclosan-containing soaps such as Softsoap® and Dial® Antibacterial Hand Soap containing 0.15% triclosan was tested using an assay essentially as set forth in Example 5, above. The results are shown in Table 116.

TABLE 116

| | Log$_{10}$ reduction from control* | | |
|---|---|---|---|
| | S. aureus | E. Coli | MRSA |
| Soft Soap ®-TC | 0.33 | 0.25 | 0.37 |
| Soft Soap ®-TC + CIN-Cit | 3.9 | 3.93 | 6.0 |
| Dial ® Soap-TC | 0.36 | 0 | 0.24 |
| Dial ® Soap-TC + Cin-Cit | 3.74 | 4.18 | 6.0 |

*Log$_{10}$ reduction from control bacterial counts (ranges from 3 4 × 10$^6$ for S. aureus, 3-5 × 10$^6$ for E. coli and 6 × 10$^5$-1.3 × 10$^6$ for MRSA.

In these experiments, the combination of cinnamon oil and citric acid was found to substantially improve the antimicrobial activity of the commercial soap.

Example 8

Because a major ingredient of cinnamon oil is eugenol, the effect of adding eugenol on the antimicrobial activity of commercial soaps was also tested. The assay was essentially as set forth in Example 5, above. The results are shown in Table 117.

TABLE 117

| | Log$_{10}$ reduction from control* S. aureus |
|---|---|
| Dial ® Soap-TC | 0.30 |
| Dial ® Soap-TC + 0.5% Eugenol + 1% CA | 2.32 |
| Dial ® Soap-TC + 0.0.5% cinnamon oil + 1% CA | 3.94 |

*Log$_{10}$ reduction from control bacterial counts (ranged from 3-4 × 10$^6$ for S. aureus).

These experiments showed that while adding eugenol improved the antimicrobial effect, the improvement was not as great as that observed for cinnamon oil.

Example 9

The following experiments were performed to evaluate the antibacterial activity of LG and Citric acid dissolved in alcohol, where the test organism used was S. aureus. Various amounts of LG oil and Citric acid were dissolved in SDA40-B alcohol, and then water was added to result in the EO concentration shown and an alcohol concentration of 10 percent. 0.9 ml of each solution were dispensed in sterile culture tubes, in triplicate, and 0.1 ml of a 10$^7$ cfu/ml S. aureus culture was added to the tubes, vortexed, and then, five minutes later, 9.0 ml of drug inactivating medium was added to each tube. Serial dilutions were made with drug inactivating medium. 0.5 ml of the dilutions were plated on trypticase soy agar ("TSA") plates. As a control, water containing 10 percent SDA40-B alcohol was processed in parallel. The plates were incubated at 37° C. for 24-48 hours and then the colony counts were determined. The results are shown in Table 118.

TABLE 118

| Compounds | Log$_{10}$ reduction from control |
|---|---|
| 1% Citric acid | 0.3 |
| 0.5% LG oil | 1.24 |
| 0.55 LG oil + 1% Citric acid | 5.59 |

* Log$_{10}$ reduction from control bacterial counts (control counts ranges from 1 × 10$^6$ to 5 × 10$^6$)

The results shown in Table 118 indicate that LG oil exhibits superior anti bacterial action in combination with Citric acid.

Example 10

Soaps were prepared containing one or more essential oil, 1% citric acid, and a soap base containing surfactants, emollients, thickeners etc. The pH of the Soaps ranged from 3.2-3.3.

TABLE 119

Soap Containing Lemongrass oil, and Citric acid (LG-Cit-4)
(4 represents total oil 0.4%)

| Ingredient | Percentage (w/w) |
|---|---|
| Deionized water | 63.5% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Lemongrass oil | 0.4% |

TABLE 120

Soap Containing Lemongrass oil, and Citric acid (LG-Cit-6)
(6 represents total oil 0.6%)

| Ingredient | Percentage (w/w) |
|---|---|
| Deionized water | 63.3% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Lemongrass oil | 0.6% |

TABLE 121

Soap Containing Lemongrass oil, Orange
oil (O oil) and Citric acid (LGO-Cit 6)
(6 represents total oil 0.6%)

| Ingredient | Percentage (w/w) |
|---|---|
| Deionized water | 63.3% |
| Methocel 40-101 | 0.1% |
| Pluronic F 87 Prill | 0.1% |
| Ucare Jr 30 | 0.1% |
| D,L Panthenol 50 W | 1.0% |

TABLE 121-continued

Soap Containing Lemongrass oil, Orange
oil (O oil) and Citric acid (LGO-Cit 6)
(6 represents total oil 0.6%)

| Ingredient | Percentage (w/w) |
| --- | --- |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Lemongrass oil | 0.4% |
| Citric acid | 1.0% |
| Orange oil | 0.2% |

TABLE 122

Soap Containing Lemon grass oil, Orange oil and Citric acid (LGO-Cit 7)
(7 represents total oil 0.7%)

| Ingredient | Percentage (w/w) |
| --- | --- |
| Deionized water | 63.2% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Lemongrass oil | 0.5% |
| Citric acid | 1.0% |
| Orange oil | 0.2% |

TABLE 123

Soap Containing Cinnamon oil, Orange oil and Citric acid (CO-Cit 6)
(6 represents total oil 0.6%)

| Ingredient | Percentage (w/w) |
| --- | --- |
| Deionized water | 63.3% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Cinnamon oil | 0.4% |
| Citric acid | 1.0% |
| Orange oil | 0.2% |

TABLE 124

Soap Containing Cinnamon oil, Orange oil and Citric acid (CO-Cit 7)
(7 represent total oil 0.7%)

| Ingredient | Percentage (w/w) |
| --- | --- |
| Deionized water | 63.2% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Cinnamon oil | 0.5% |
| Citric acid | 1.0% |
| Orange oil | 0.2% |

TABLE 125

Soap Containing Orange oil and Citric acid (O-Cit 2)
(2 represents total oil 0.2%)

| Ingredient | Percentage (w/w) |
| --- | --- |
| Deionized water | 63.7% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Citric acid | 1.0% |
| Orange oil | 0.2% |

TABLE 126

Soap Containing Basil oil ("B oil"), Orange oil("O oil") and Citric acid (BO-Cit 6)
(6 represents total oil 0.6%)

| Ingredient | Percentage (w/w) |
| --- | --- |
| Deionized water | 63.3% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |
| Montalene C 40 | 1.5% |
| 2-Phenoxy-ethanol | 1.0% |
| Glycerin | 2.0% |
| SDA-40B | 15.5% |
| Basil oil | 0.4% |
| Citric acid | 1.0% |
| Orange oil | 0.2% |

TABLE 127

Soap Containing Citronella oil ("CR oil"),
Orange oil("O oil"), and Citric acid (CRO-Cit 6)
(6 represents total oil 0.6%)

| Ingredient | Percentage (w/w) |
| --- | --- |
| Deionized water | 63.3% |
| Methocel 40-101 | 0.1% |
| Pluronic F 87 Prill | 0.1% |
| Ucare Jr 30 | 0.1% |
| D,L Panthenol 50 W | 1.0% |
| Incromide oxide L | 3.0% |
| Crosultane C-50 | 3.0% |

TABLE 127-continued

Soap Containing Citronella oil ("CR oil"),
Orange oil("O oil"), and Citric acid (CRO-Cit 6)
(6 represents total oil 0.6%)

| Ingredient | Percentage (w/w) |
|---|---|
| Montalene C 40 | 1.5% |
| 2-Phenoxy-ethanol | 1.0% |
| Glycerin | 2.0% |
| SDA-40B | 15.5% |
| Citronella oil | 0.4% |
| Citric acid | 1.0% |
| Orange oil | 0.2% |

Example 11

Certain soaps prepared in Example 14 were tested for antimicrobial activity.

The following method was used. A mixture of 0.1 ml of $10^7$ cfu/ml of *S. aureus* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. Soft Soap® and Dial® soaps containing 0.15% triclosan was also tested similarly at the same time. The soap base without essential oils and Citric acid containing the culture were used as controls. The results, showing 30 second kill activity, are shown in Table 128.

TABLE 128

| Soap | $Log_{10}$ reduction from control* |
|---|---|
| LG-Cit 4 | 3.9 |
| LG-Cit 6 | 4.2 |
| O-Cit 2 | 1.5 |
| LGO Cit 6 | 6.4 |

*$Log_{10}$ reduction from control bacterial counts (control counts ranges from $1 \times 10^6$ to $5 \times 10^6$)

These data show that when citric acid was used in combination with 0.4% LG oil+0.2% O oil (LGO-Cit 6) superior antibacterial activity was observed as compared to that of combination of Citric acid and LG oil 0.6% (LG-Cit 6) or the additive activity of Citric acid+0.4% LG oil (LG-Cit 4) and Citric acid+0.2% Orange oil (O-Cit 2).

Example 12

Certain soaps described in Example 10 were tested for antimicrobial activity.

The following method was used. A mixture of 0.1 ml of $10^7$ cfu/ml of *S. aureus* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hrs and the colony counts were determined. Soft Soap® and Dial® soaps containing 0.15% triclosan was also tested similarly at the same time. The soap base without essential oils and citric acid containing the culture were used as controls. The results, showing 30 second kill activity, are shown in Table 129.

TABLE 129

| Soap | $Log_{10}$ reduction from control* |
|---|---|
| LGO-Cit 6 | 6.4 |
| LGO-Cit 7 | 6.5 |
| CO-Cit 6 | 5.1 |
| CO-Cit 7 | 5.2 |
| BO-Cit 6 | 2.87 |
| CRO-Cit 6 | 4.57 |

*$Log_{10}$ reduction from control bacterial counts (ranges from $1 \times 10^6$ to $3 \times 10^6$.)

These data show that LGO-Cit Soaps were found to exhibit higher antibacterial activity compared to the other essential oil/citric acid combination soaps tested.

Example 13

The following experiments were performed to evaluate the antibacterial activity of triclosan, LG oil, and combinations of triclosan and LG oil.

Patent application WO/2007/077573 by Mukhopadhyay et al. describes an antimicrobial composition containing triclosan and an essential oil where the ratio of triclosan to the essential oil is 1:5 to 1:100 and the preferred ratio range is 1:10 to 1:90. In the example provided in United States Patent Application Publication No. 20050019431 by Modak et al., triclosan and essential oil at 1:1 ratio showed neither synergistic nor enhanced activity.

Triclosan ("TC") is often used in personal care products at a concentration of 0.15-0.3%. In order to determine whether or not TC at this concentration would enhance the activity of essential oil at 0.4-0.7% which is the concentration used in various formulations described in this application, the antibacterial activity of soaps containing triclosan; LG oil; or TC and LG oil at TC:LG weight ratios of 1:1.7 to 1:4.6 were evaluated.

To prepare the soaps, TC, LG oil or their combination were dissolved in SDA40 B alcohol and then added to Softsoap® (a formulation lacking triclosan), then diluted with water, where the amount of SDA40B alcohol used represented 5.5% of the final solution and the amount of Softsoap® used represented 92% of the final solution. Soft Soap® was used as the control in this study.

The following method was used. A mixture of 0.1 ml of $10^8$ cfu/ml of *S. aureus* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 130.

TABLE 130

| Soap | $Log_{10}$ reduction from control* |
|---|---|
| Softsoap ® + 0.15% TC | 0.70 |
| Softsoap ® + 0.3% TC | 0.81 |
| Softsoap ® + 0.5% LG oil | 0.76 |
| Softsoap ® + 0.7% LG oil | 0.75 |
| Softsoap ® + 0.15% TC + 0.5% LG oil | 0.74 |
| Softsoap ® + 0.15% TC + 0.7% LG oil | 0.92 |
| Softsoap ® + 0.3% TC + 0.5% LG oil | 0.77 |
| Softsoap ® + 0.3% TC + 0.7% LG oil | 0.77 |

*$Log_{10}$ reduction from control bacterial counts (ranges from $5.8 \times 10^7$ to $6.4 \times 10^7$ cfu)

These results indicate that no synergistic or enhanced effect was seen when triclosan was combined with LG oil at weight ratios falling within the range of 1:1.7 to 1:4.6.

Example 14

The antibacterial activity of soaps containing 1) TC-LGO-Cit 6 at weight ratios within the range of between 1:3.3 and 1:4.7 (TC:LG) and between 1:1.4 and 1:2 (LG:Citric acid) were evaluated against *S. aureus*. To prepare the soaps, triclosan/essential oil(s)/citric acid were dissolved in SDA40 B alcohol and added to Softsoap® (lacking triclosan) and diluted with water, so that the final concentration of alcohol was 5.5% and the final concentration of Softsoap® was 92 percent. A mixture of 0.1 ml of $10^7$ cfu/ml of *S. aureus* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 131.

TABLE 131

| Soap | $Log_{10}$ reduction from control* |
|---|---|
| Softsoap ® | — |
| Softsoap ® + 0.15% TC | 0.24 |
| Softsoap ® + 1% citric acid | 1.49 |
| Softsoap ® + 0.15% TC + '% citric acid | 2.01 |
| Softsoap ® + 0.15% TC + 0.5% LG oil + 1% citric acid | 2.41 |
| Softsoap ® + 0.15% TC + 0.4% LG oil + 0.2% Orange oil + 1% citric acid | 7.93 |

*$Log_{10}$ reduction from control bacterial counts (ranges from $1 \times 10^6$ to $5 \times 10^6$ cfu).

The foregoing data show that citric acid was found to enhance the activity of triclosan, and that addition of LG oil+O oil to a combination of triclosan and citric acid further enhanced the effect.

Example 15

The following experiments were performed to compare the antibacterial activity of combinations of (i) lemongrass oil citric acid+triclosan; (ii) lemongrass oil+citric acid; and (iii) cinnamon oil-citric acid+triclosan, all in a Softsoap® base.

To prepare the soaps, triclosan/essential oil/citric acid were dissolved in SDA40 B alcohol and added to Softsoap® (lacking triclosan) and diluted with water, so that the final concentration of alcohol was 5.5% and the final concentration of Softsoap® was 92 percent. A mixture of 0.1 ml of $10^8$ cfu/ml of *S. aureus* culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The results are shown in Table 132.

TABLE 132

| Soap | $Log_{10}$ reduction from control* |
|---|---|
| Softsoap ® + 0.15% TC | 0.7 |
| Softsoap ® + 0.15% TC + 0.4% LG oil + 0.2% Orange oil + 1% citric acid | 7.93 |
| Softsoap ® + 0.4% LG oil + 0.2% Orange oil + 1% citric acid | 5.73 |
| Softsoap ® + 0.15% TC + 0.4% C oil + 0.2% Orange oil + 1% citric acid | 5.50 |
| Softsoap ® + 0.4% C oil + 0.2% Orange Oil + 1% citric acid | 4.39 |

*$Log_{10}$ reduction from control bacterial counts (ranges from $6.4 \times 10^7$ to $9.9 \times 10^7$ cfu)

The above data demonstrate, among other things, that LGO-Cit+Triclosan was found to be more effective than LGO-Cit and CO-Cit+Triclosan.

Example 16

The following experiments were performed to evaluate the effect of adding various essential oil combinations, citric acid (0.5-0.7%), and SDA 40 B alcohol (5.5%) to commercial triclosan-containing soaps such as Dial® Soap and Softsoap® containing 0.15% Triclosan ("Dial® Soap-TC" and "Softsoap®-TC" respectively). A mixture of 0.1 ml of $10^8$ cfu/ml of *S. aureus* culture and 0.1 ml of bovine serum were placed in a sterile culture tube. 0.8 ml of the test soap formulation (or phosphate buffered saline as control) was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hours and the colony counts were determined. The formulations are shown in Tables 133-136. The results are shown in Table 137.

TABLE 133

Dial ® Soap TC-CO-Cit 7

| Ingredient | Percentage (w/w) |
|---|---|
| Cinnamon oil | 0.5 |
| Orange Oil | 0.2 |
| Citric acid | 1.0 |
| SDA 40 B alcohol | 5.5 |
| Dial ® Soap-TC | 92.8 |

TABLE 134

Dial ® Soap TC-LGO-Cit 7

| Ingredient | Percentage (w/w) |
|---|---|
| Lemon Grass oil | 0.5 |
| Orange Oil | 0.2 |
| Citric acid | 1.0 |
| SDA 40 B alcohol | 5.5 |
| Dial Soap ®-TC | 92.8 |

TABLE 135

Dial ® Soap TC-LG-Cit 5

| Ingredient | Percentage (w/w) |
|---|---|
| Lemon Grass oil | 0.5 |
| Citric acid | 1.0 |

TABLE 135-continued

Dial ® Soap TC-LG-Cit 5

| Ingredient | Percentage (w/w) |
|---|---|
| SDA 40 B alcohol | 5.5 |
| Dial ® Soap-TC | 92.8 |

TABLE 136

Softsoap ® TC-LGO-Cit 7

| Ingredient | Percentage (w/w) |
|---|---|
| Lemon Grass oil | 0.5 |
| Orange Oil | 0.2 |
| Citric acid | 1.0 |
| SDA 40 B alcohol | 5.5 |
| Softsoap ®-TC | 92.7 |

TABLE 137

Results

| Soap | $Log_{10}$ reduction from control* |
|---|---|
| Dial ® Soap TC | 0.36 |
| Dial ® Soap-TC-CO-Cit 7 | 3.9 |
| Dial ® Soap-TC-LG-Cit 5 | 3.35 |
| Dial ® Soap-TC-LGO-Cit 7 | 5.09 |
| Softsoap ®-TC | 0.33 |
| Softsoap ®-TC-LGO-Cit 7 | 4.66 |
| Softsoap ®-TC + 1% citric acid | 2.64 |

*$Log_{10}$ reduction from control bacterial counts (ranges from $2.0 \times 10^8$ to $3.5 \times 10^8$ cfu)

The above results indicate that citric acid was found to enhance the activity of soaps containing triclosan; the combination of citric acid and essential oils was found to increase the antimicrobial activity of soap containing triclosan, and superior antimicrobial action was associated with a combination of citric acid, lemongrass and orange oils, and triclosan.

Example 17

The pH of soaps containing 1% citric acid typically ranges between 3.2-3.3. To determine whether or not the superior efficacy observed with the combination of essential oils and citric acid is due to the acidic pH, certain EO/citric acid containing-soaps were adjusted to pH 6.0 with 10 N sodium hydroxide and their antibacterial efficacy tested and compared to the corresponding soaps without pH adjustment. For the evaluation of antimicrobial activity, a mixture of 0.1 ml of $10^7$ cfu/ml of *S. aureus* culture (ATCC #6538) and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hrs and the colony counts were determined. The results are shown in Table 138. ("Softsoap®-TC" is Softsoap® containing 0.15 percent triclosan).

TABLE 138

| Soap | $Log_{10}$ reduction from control* |
|---|---|
| CO-Cit + Softsoap ®-TC pH 3.25 | 3.9 |
| CO-Cit + Softsoap ®-TC pH 6.0 | 3.25 |
| CLGO-Cit + Softsoap ®-TC pH 3.25 | 5.1 |
| CLGO-Cit + Softsoap ®-TC pH 6.0 | 5.65 |

*$Log_{10}$ reduction from control bacterial counts (ranges from $1 \times 10^6$ to $5 \times 10^6$.)

Conclusion: The efficacy was similar at both pH values tested. This indicates that the superior activity of essential oils and citric acid observed is not due to the acidic pH.

Example 18

Household cleansers were prepared comprising citric acid (1-2%), alcohol, and either (i) lemongrass oil; (ii) a combination of lemongrass oil and pine oil; (iii) a combination of lemongrass oil and orange oil; or (iv) a combination of pine oil and orange oil. The antimicrobial effectiveness of these formulations were tested and compared to commercial Pinesol® cleanser (containing 8.7 percent pine oil and other ingredients including detergent and other cleaning agents) as a control.

TABLE 139

Stock solution of hard surface Disinfectant-LG-Cit 2

| Ingredient | Percentage (w/w) |
|---|---|
| Lemongrass oil | 2.0 |
| Citric Acid | 20.0 |
| SDA 40B alcohol | 76.5 |
| Pluronic Surfactant L-61 | 0.5 |
| Pluronic Surfactant F-127 | 0.5 |
| Pluronic Surfactant F-87 | 0.5 |

TABLE 140

Stock solution of hard surface Disinfectant.-LGP-Cit 4

| Ingredient | Percentage (w/w) |
|---|---|
| Lemongrass oil | 1.0 |
| Pine oil | 3.0 |
| Citric Acid | 20.0 |
| SDA 40B alcohol | 74.5 |
| Pluronic Surfactant L-61 | 0.5 |
| Pluronic Surfactant F-127 | 0.5 |
| Pluronic Surfactant F-87 | 0.5 |

TABLE 141

Stock solution of hard surface Disinfectant.-P-Cit 5

| Ingredient | Percentage (w/w) |
|---|---|
| Pine oil | 5.0 |
| Citric Acid | 20.0 |
| SDA 40B alcohol | 73.5 |
| Pluronic Surfactant L-61 | 0.5 |
| Pluronic Surfactant F-127 | 0.5 |
| Pluronic Surfactant F-87 | 0.5 |

After tenfold dilution of each stock solution the disinfectant contained the following percentages (w/w) of each ingredient.

TABLE 142

| Disinfectant | Ingredients |
| --- | --- |
| Surface Disinfectant-LG cit 2 | 0.2% Lemon grass oil |
| | 2% Citric acid |
| | 7.65% Alcohol |
| | 0.15% surfactants |
| Surface Disinfectant-LG P cit 4 | 0.3% Pine oil |
| | 0.1% Lemon grass oil |
| | 2% Citric Acid |
| | 7.45% alcohol |
| | 0.15% Surfactants |
| Surface Disinfectant-P cit 5 | 0.5% Pine oil |
| | 2% Citric acid |
| | 7.45% alcohol |
| | 0.15% surfactants |

To prepare the solution of Pinesol® to serve as control, as per the manufacturer's instruction, 6 ml of the Pinesol® containing 8.5% pine oil was diluted to 100 ml. This diluted sample contained 0.52% pine oil.

To test the antimicrobial activity, 0.1 ml of culture containing approximately $1 \times 10^7$ colony forming units ("cfu") of S. aureus per milliliter was spread evenly on the surface of $2.5 \times 11$ cm$^2$ tiles using a glass rod and left at room temperature for 10 minutes to dry. After 10 minutes 0.3 ml of the diluted surface disinfectant was spread evenly on the tiles with a sterile glass rod and left for another 10 minutes to dry. The tiles were rinsed with 9.6 ml of inactivating medium (BPBNS), which was collected for testing. The collected medium was serially diluted and 0.5 ml was plated onto TSA plates and incubated at 37° C. for 18-24 hours. The colonies on the plates were counted and the values converted to $\log_{10}$.

TABLE 143

| | $\log_{10}$ reduction from control bacterial counts* | | | |
| --- | --- | --- | --- | --- |
| Organism | Disinfectant LG-Cit | Disinfectant LGP-Cit | Disinfectant P-Cit | Pine Sol |
| S. aureus | 3.56 | 1.89 | 0.81 | 2.4 |

*$\log_{10}$ reduction from control bacterial counts (ranges from $1 \times 10^6$-$5 \times 10^6$)

These data indicate that a surface cleaner containing 0.2% LG oil and 2.0% Citric acid was found to be considerably more effective than a cleaner containing 0.5% Pine oil and 2% Citric acid as well as commercial Pinesol® Surface cleaner containing 0.52% Pine oil. The cleanser containing 0.3% Pine oil+0.1% LG oil+2% Citric acid was also found to be more effective than the one containing 0.5% Pine oil and 2% Citric acid.

Example 19

The following stock solution was prepared.

TABLE 144

Stock Solution of hard surface Disinfectant.-POCit 7

| Ingredient | Percentage (w/w) |
| --- | --- |
| Pine oil | 5.0 |
| Orange oil | 2.0 |
| Citric Acid | 10.0 |
| SDA 40B alcohol | 53.5 |
| Pluronic Surfactant L-61 | 0.5 |
| Pluronic Surfactant F-127 | 0.5 |
| Pluronic Surfactant F-87 | 0.5 |

7.2% of the stock hard disinfectant was diluted with water to 100% before use. These diluted samples contained the following concentrations of active ingredients.

TABLE 145

| Disinfectant | Ingredients |
| --- | --- |
| Surface Disinfectant-PO Cit 7 | 0.5% Pine oil |
| | 0.2% Orange oil |
| | 1% Citric Acid |
| | 5.35% alcohol |
| | 0.15% Surfactants |

The following stock solution was prepared:

TABLE 146

Stock Solution of hard surface Disinfectant.-LGOCit 7

| Ingredient | Percentage (w/w) |
| --- | --- |
| Lemongrass oil | 5.0 |
| Orange oil | 2.0 |
| Citric Acid | 10.0 |
| SDA 40B alcohol | 53.5 |
| Pluronic Surfactant L-61 | 0.5 |
| Pluronic Surfactant F-127 | 0.5 |
| Pluronic Surfactant F-87 | 0.5 |

7.2% of the stock hard disinfectant was diluted with water to 100% before use. This diluted samples contained the following concentrations of active ingredients:

TABLE 147

| Disinfectant | Ingredients |
| --- | --- |
| Surface Disinfectant-LGO Cit 7 | 0.5% LG oil |
| | 0.2% Orange oil |
| | 1% Citric Acid |
| | 5.35% alcohol |
| | 0.15% Surfactants |

The method used in Example 18 was used to test antimicrobial activity.

TABLE 148

| | S. aureus | P. aeruginosa | E. coli |
| --- | --- | --- | --- |
| $\log_{10}$ reduction in bacteria-PO-Cit 7 | 0.6 | 5.1 | 5.1 |
| $\log_{10}$ reduction in bacteria-LGO-Cit 7 | 5.9 | 4.8 | 5.09 |

*$\log_{10}$ reduction from control bacterial counts (ranges from $1 \times 10^6$-$5 \times 10^6$)

The foregoing data indicate that LGO-Cit is effective against both gram positive and gram negative organisms while PO Cit is not very effective against the Gram positive organism S. aureus.

Example 20

The following experiments were carried out using either soap or surface disinfectants containing the EO(s)/citric acid combinations indicated. The test organism used was Candida albicans.

Where soap was employed, the following method was used. A mixture of 0.1 ml of $10^7$ cfu/ml of C. albicans culture and 0.1 ml of bovine serum were placed in a sterile culture tube. 0.8 ml of the test soap formulation was added to the tube and vortexed for 30 seconds. 9.0 ml DFN was added to the tube to neutralize the activity of the soap; this tube was then vortexed and serially diluted with DFN. 0.5 ml of the diluted solution was plated on trypticase soy agar plates, incubated at 37° C. for 24-48 hrs and the colony counts were determined. The results, showing 30 second kill activity, are shown in Table 149.

Where surface disinfectant was employed, the following method was used. 0.1 ml of culture containing approximately $1 \times 10^7$ colony forming units ("cfu") of *C. albicans* per milliliter was spread evenly on the surface of $2.5 \times 11$ cm$^2$ tiles using a glass rod and left at room temperature for 10 minutes to dry. After 10 minutes 0.3 ml of the diluted surface disinfectant was spread evenly on the tiles with a sterile glass rod and left for another 10 minutes to dry. The tiles were rinsed with 9.6 ml of inactivating medium (BPBNS), which was collected for testing. The collected medium was serially diluted and 0.5 ml was plated onto TSA plates and incubated at 37° C. for 18-24 hours. The colonies on the plates were counted and the values converted to $\log_{10}$.

TABLE 149

| Formulation | Log$_{10}$ reduction from control* |
|---|---|
| CO-Cit 6 Soap | 1.02 |
| LGO-Cit 6 Soap | 1.27 |
| CO-Cit 7 Surface Disinfectant | 5.2 |
| LGO-Cit 7 Surface Disinfectant | 4.81 |

*Control counts range from $1 \times 10^6$ to $5 \times 10^6$

These results show that CO groups and LGO groups show similar activity against *C. albicans*.

Example 21

Evaluation of the rapid antibacterial activity of various soap formulations was performed as follows.

Method of evaluation of rapidity of kill of soaps. The rapid antimicrobial efficacy of the soaps containing LG and various combinations were tested as follows. A mixture of 0.1 ml of $10^9$ cfu/ml of bacterial cultures and 0.1 ml of bovine serum was placed in a sterile culture tube. 0.8 ml of the test soap formulation was added to the tube and vortexed for 30 seconds. 9.0 ml drug neutralizing fluid (DNF) was added to the tube to neutralize the activity of the soap, this tube was vortexed and serially diluted with DNF. 0.5 ml of the diluted solution was plated on trypticase soy agar plates, incubated at 37° C. for 24-48 hours and the colony counts were determined. The soap base without essential oils citric acid, secondary alcohol and Incroquat containing the culture were also tested. PBS was used as the control. LG-O-Cit 5 comprises 0.3 percent (weight/weight) lemongrass oil, 0.3 percent (weight/weight) orange oil, 1.0 percent (weight/weight) citric acid, 1.0 percent (weight/weight) 2-phenoxyethanol and 15 percent (weight/weight) SDA-40B alcohol. LG-O-Cit 4 comprises 0.3 percent (weight/weight) lemongrass oil, 0.1 percent (weight/weight) orange oil, 1.0 percent (weight/weight) citric acid, 1.0 percent (weight/weight) 2-phenoxyethanol and 15 percent (weight/weight) SDA-40B alcohol. The amount of alkanediol, where present, is 0.3 percent (weight/weight). The complete formulations for the soaps specified are set forth in section 4.9, above. The results are shown in Table 150 below.

TABLE 150

Enhancement of the antibacterial activity of LG-O-Cit composition by 0.3% of alkanediols (Test Organism: *S. aureus*)

| Soap formulations | Log$_{10}$ reduction from control |
|---|---|
| Base | 1.8 |
| LG-O-Cit 5 | 3.7 |
| 1,2 decanediol (0.3%) | 0.6 |
| LG-O-Cit 5 + 1,2 decanediol | 4.5 |
| LG-O-Cit 4 | 3.6 |
| LG-O-Cit 4 + 1,2 decanediol | 4.8 |
| LG-O-Cit 4 + 1,2 dodecanediol | 4.5 |
| LG-O-Cit 4 + 1,2 Tetradecanediol | 4.5 |

*Log$_{10}$ reduction from Control bacterial counts (ranges from $2 \times 10^8$-$5 \times 10^8$)

The results shown in Table 150 indicate that the alkanediols tested enhanced the antibacterial activity of LG and O oil and citric acid disinfectant composition at a concentration of 0.3 percent (weight/weight).

Example 22

The method described in Example 21, above, was used to evaluate the antibacterial activity of soap formulations comprising 0.5 percent of alkanediols. LG-O-Cit 4A comprises 0.3 percent (weight/weight) lemongrass oil, 0.1 percent (weight/weight) orange oil, 1.0 percent (weight/weight) citric acid, 1.0 percent (weight/weight) 2-phenoxyethanol and 17 percent (weight/weight) SDA-40B alcohol. The amount of alkanediol, where present, is 0.5 percent (weight/weight). The complete formulations for the soaps specified are set forth in section 4.6, above. The results are shown in Table 151 below.

TABLE 151

Enhancement of the antibacterial activity of LG-O-Cit A Composition by 0.5% of alkanediols
Rapid antimicrobial activity (30 second Kill)
(Test Organism *S. aureus*)

| Soap formulations | Log$_{10}$ reduction from control |
|---|---|
| Base | 0.8 |
| LG-O-Cit 4A | 4.1 |
| 1,2 decanediol(0.5%) | 1.4 |
| LG-O-Cit 4A + 1,2 decanediol | 6.0 |
| LG-O-Cit 4A + 1,2 dodecanediol | 6.1 |
| LG-O-Cit 4A + 1,12 dodecanediol | 6.0 |
| LG-O-Cit 4A + 1,2 Tetradecanediol | 6.0 |
| LG-O-Cit4A + 0.25%1,2decanediol + 0.25% 1,12Dodecanediol | 6.0 |
| Cn-O-Cit4A | 3.7 |
| Cn-O-Cit4A + 1,2 decanediol | 4.9 |

(pH of all the soaps ranged from 4.5-4.6)
*Log$_{10}$ reduction from Control bacterial counts (ranges from $2 \times 10^8$-$5 \times 10^8$)

The results shown in Table 151 indicate that alkanediols at 0.5% concentration showed significant enhancement of the antibacterial activity of LG+O oil+citric acid or Cn+O oil and citric acid disinfectant composition.

Example 23

To evaluate the effect of decanediol on the antibacterial activity of citric acid or citric acid in combination with essential oils, the following experiments were performed. The compounds indicated below were incorporated into soft soap lacking triclosan and the activity was evaluated. Activity was measured as described in Example 22. The results are shown in Table 152.

TABLE 152

Rapid antimicrobial activity (30 second Kill)
(Test Organism *S. aureus*)

| Soap formulations (% w/w) | Log$_{10}$ reduction from control |
|---|---|
| Plain Soft soap | 0.2 |
| 0.5 decanediol | 1.4 |
| 1.0 citric acid | 1.3 |
| 0.5 decanediol + 1 citric acid | 6.5 |
| 0.3 + 0.1 LG + O | 0.1 |
| 0.5 decanediol + 1 citric acid + 0.3 + 0.1 LG + O | 7.0 |
| 0.25 decanediol + 0.5 citric | 4.7 |
| 0.15 + 0.06 LG + O | 0.1 |
| 0.25 decanediol + 0.5 citric + 0.15 + 0.06 LG + O | 5.6 |

*Log$_{10}$ reduction from PBS(Control) bacterial counts (ranges from $7 \times 10^7$-$1 \times 10^8$)

The results shown in Table 152 indicate that decanediol and citric acid exhibit synergistic activity, and that further addition of essential oil enhances the activity. The use of decanediol+citric acid+essential oils in soap even at low concentrations was found to show superior antibacterial activity.

Example 24

To determine the effect of LG-O-Cit-1,2 decanediol on the antibacterial activity of triclosan-containing soap, the following experiments were performed.

Dial® soap containing 0.15% Triclosan (Dial-T Soap) was used for this test. The following formulation was prepared. The antibacterial activity was then tested using the method set forth in Example 21. The results are shown in Table 153.

TABLE 153

Dial ®-T Soap Containing LG-O-Cit 4 and 0.5% 1,2 decanediol

| Ingredient | Percentage (w/w) |
|---|---|
| Dial ®-T soap | 90.0 |
| SDA 40B | 8.1 |
| Lemon grass oil | 0.3 |
| Orange oil | 0.1 |
| Citric acid | 1.0 |
| 1,2 decanediol | 0.5 |

Original pH was 3.2 pH adjusted to 4.5 with 10.N NaOH.

TABLE 154

Enhancement of the activity of Triclosan by LG-O-Cit-1,2 Decanediol
Rapid antimicrobial activity (30 second Kill)
(Test Organism *S. aureus*)

| Soap formulations | Log$_{10}$ reduction from control |
|---|---|
| Dial ®-T soap | 0.7 |
| Dial ®-T Soap + LG-O-Cit 4 | 5.5 |
| Dial ®-T Soap + LG-O-Cit4-0.5% 1,2 decanediol | 8.0 |

*Log$_{10}$ reduction from Control bacterial counts (ranges from $2 \times 10^8$-$5 \times 10^8$)

The foregoing results indicate that decanediol enhances the activity of Dial®-T Soap+LG-O-Cit 4.

Example 25

The antibacterial activity of LG-O-CitA-D-T Lotion, having the following formulation, was tested in a pigskin model.

TABLE 155

| Ingredient | Percentage (w/w) |
|---|---|
| Water | 65.6 |
| U Care-JR 30M | 0.25 |
| PolyoxWSR-205 | 0.1 |
| Incroquat TMS Behenyl | 2.0 |
| Isopropyl myristate | 1.0 |
| Acetulan | 1.0 |
| Vitamin E | 0.2 |
| Zinc stearate | 0.2 |
| Polawax NF | 2.75 |
| Glycerin | 2.0 |
| Allantoin | 0.2 |
| Dimethicone copolyol (Q2-5220) | 2.5 |
| Citric acid | 1.0 |
| 1,2 decanediol | 0.5 |
| Tocopheryl acetate | 0.5 |
| Glyceryl stearate (Arlacel165) | 1.0 |
| Butylene glycol | 3.0 |
| SDA-40-B | 15 |
| Lemongrass oil | 0.5 |
| Tea tree oil | 0.5 |
| Orange oil | 0.1 |
| 1,2 Decanediol (Symclairol) | 0.5 |
| Triclosan | 0.3 |
| (pH adjusted to 4.5-5.0) | |

The pigskin model assay was as follows. Six sets of 3×3 cm$^2$ pig skin each mounted on a petriplate were rinsed in 70% isopropanol, and air dried. One piece of the pair was contaminated with 300 of $10^8$ efu of MRSA culture; the two pieces were then rubbed against each other for 30 seconds, and left at 37° C. to dry for one hour. 3 pairs were used for control and another 3 pairs were used for the test, which was as follows.

To one piece of the pair from the control, 0.1 gm of placebo cream same as LG-O-Cit4-D (above) without SDA-40-B, lemongrass oil, tea tree oil, orange oil, 1,2 decanediol (Symclairol) was applied, and rubbed against the other piece for 15 seconds and left at 37° C. for 1 hour. The same procedure was repeated with the test skins in which LG-O-CitA-D-T was applied. Following this, 0.2 ml dilution media (DM) was added to one skin piece and both pieces rubbed again for 15 seconds. The surviving organisms were recovered from the skin by rinsing each piece with 9.9 ml of DM. The washing fluid from both pieces was collected in one petri dish, mixed and transferred to a culture tube from which further serial dilutions were made. Aliquots from the dilutions were plated on TSA plates and incubated for 24-48 hours at 37° C. before colony counts (baseline counts) were determined. The results are shown in Table 156.

TABLE 156

Reduction of Bacterial growth 1 hour post treatment

| Treatment cream | Bacterial counts (cfu/skin) | Log$_{10}$ reduction from control counts |
|---|---|---|
| PBS | $2.2 \times 10^6$ | — |
| Placebo cream(control) | $2.0 \times 10^6$ | — |
| LG-O-Cit A-D-T Lotion | $7.6 \times 10^3$ | 2.37 |

Example 26

The antibacterial activity of preservative compositions was evaluated.

TABLE 157

Preservative composition A

| Ingredient | Percentage (w/w) |
|---|---|
| Lemongrass oil | 10 |
| Farnesol | 10 |
| Orange oil | 5 |
| lactic acid | 7 |
| 1,2 decanediol | 7 |
| SDA 40 B alcohol | 61 |

TABLE 158

Preservative composition B

| Ingredient | Percentage (w/w) |
|---|---|
| Lemongrass oil | 15 |
| Farnesol | 15 |
| Orange oil | 10 |
| lactic acid | 10 |
| SDA 40 B alcohol | 50 |

TABLE 159

Preservative composition C

| Ingredient | Percentage (w/w) |
|---|---|
| Farnesol | 17 |
| Citric acid | 7 |
| 1,2 decanediol | 7 |
| SDA 40 B alcohol | 69 |

TABLE 160

Preservative composition D

| Ingredient | Percentage (w/w) |
|---|---|
| Lemongrass oil | 15 |
| Orange oil | 5 |
| Lactic acid | 10 |
| 1,2 decanediol | 20 |
| 1,2 Octanediol | 20 |
| SDA 40 B alcohol | 30 |

TABLE 161

Preservative composition E

| Ingredient | Percentage (w/w) |
|---|---|
| Lemongrass oil | 15 |
| Orange oil | 5 |
| Lactic acid | 10 |
| 1,2 Octanediol | 40 |
| SDA 40 B alcohol | 30 |

The pH of these solutions are adjusted to 5.0. 0.5-5.0% of these preservatives can be used in various formulations.

Evaluation of the Preservative efficacy of Composition A and 13. The following

Cream base was prepared to incorporate the preservative before testing.

TABLE 162

Preservative composition F

| Ingredient | Percentage (w/w) |
|---|---|
| Water | 70.24 |
| Ucare JR 40 | 0.3 |
| Polowax | 3.0 |
| Incroquat Behenyl TMS | 3.0 |
| Petroleum jelly | 5.0 |
| Stearyl alcohol | 7.0 |
| Propylene glycol | 2.0 |
| Isopropyl myristate | 4.0 |
| Sorbitan oleate | 2.0 |
| Polyoxyl 40 stearate | 2.0 |

An overnight culture of bacteria grown in Trypticase Soy Broth (TSB) was diluted with TSB to obtain $10^8$ CFU organism/ml. For the test samples, 2% of the preservative was added to 10 grams of the cream and mixed well. From this sample, 1 gram aliquots were placed into 10 ml sterile plastic culture tubes and 0.1 ml (100 microliters) of the test inoculum was added and vortexed until uniformly blended. The tubes were then placed into incubators at 37° C. All tubes were incubated for a total of 3 days. At the end of the incubation period 9.0 ml of Butterfield Phosphate Buffered solution with neutralizer was added to the incubated cultured sample and vortexed until completely mixed. The samples were serially diluted and then plated in Trypticase soy agar (TSA). the plates were incubated at 37° C. temperature for 24-48 hours and the counts were read. The results are shown in Table 163, below.

TABLE 163

$Log_{10}$ Reduction from control growth

| | S. aureus | P. aeruginosa |
|---|---|---|
| Control | — | — |
| Preserv A | 7.8 | 8.0 |
| Preserv B | 6.7 | 4.0 |

Control growth for *S. aureus* and *P aeruginosa* are $6.5 \times 10^8$ and $1 \times 10^8$ cfu/gm respectively.

Example 27

The following experiments were performed to evaluate wound dressings impregnated with essential oils, citric acid and decanediol.

TABLE 164

Antimicrobial Impregnation solution

| Ingredient | Percentage (w/w) |
|---|---|
| Lemongrass oil | 0.3 |
| Orange oil | 0.1 |
| Tea tree oil | 0.5 |
| *Calandula* oil | 0.5 |
| Citric acid | 1.0 |
| Olive oil | 5.0 |
| Propylene glycol | 10 |

TABLE 164-continued

Antimicrobial Impregnation solution

| Ingredient | Percentage (w/w) |
|---|---|
| Decanediol | 0.5 |
| SDA 40 B alcohol | 51.7 |
| U care JR 30 | 0.4 |
| Water | 30 |

TABLE 165

Antimicrobial/anti inflammatory Impregnation solution

| Ingredient | Percentage (w/w) |
|---|---|
| Lemongrass oil | 0.3 |
| Orange oil | 0.1 |
| Tea tree oil | 0.5 |
| *Calandula* oil | 0.5 |
| Citric acid | 1.0 |
| Olive oil | 5.0 |
| Propylene glycol | 10 |
| Decanediol | 0.5 |
| SDA 40 B alcohol | 51.0 |
| U care JR 30 | 0.4 |
| Curcumin | 0.3 |
| Water | 29.7 |

Wound dressings (Dukal non adherent pad) were dipped into the antimicrobial impregnation solution and dried for 24 hours. The dressings were cut into 1 cm² and the zones of inhibition against various organisms were determined.

Zones of inhibition test. 1×1 cm² piece of each dressing was placed on Trypticase soy agar plate seeded on the surface with 0.3 mL of $10^8$ colony forming units (CFU)/mL) of the test organism. The plates were incubated at 37° C. for 24 hours. The zone of inhibition around the catheter segments, excluding the diameter of patch was measured. The results are shown in Table 166.

TABLE 166

Antimicrobial Impregnation solution

| Organism | Zone of inhibition (mm) |
|---|---|
| S. aureus | 7.0 |
| MRSA | 8.0 |
| P. aeruginosa | 5.0 |
| C. albicans | 9.0 |

Example 28

The following experiment was performed to evaluate the efficacy of creams containing preservative compositions.

Creams containing 2.0%-3.0% of preservative compositions were prepared and tested according to the following method.

TABLE 167

Formulation

| Ingredients | Percentage (w/w) |
|---|---|
| Water | 70.24 |
| Ucare JR 40 | 0.3 |
| Polowax | 3.0 |
| Incroquat Behenyl TMS | 3.0 |

TABLE 167-continued

Formulation

| Ingredients | Percentage (w/w) |
|---|---|
| Petroleum Jelly | 5.0 |
| Stearyl alcohol | 7.0 |
| Propylene glycol | 2.0 |
| Isopropyl myristate | 4.0 |
| Sorbitan oleate | 2.0 |
| Polyoxyl 40 stearate | 2.0 |

An overnight culture of bacteria grown in Trypticase Soy Broth (TSB) was diluted with TSB to obtain 108 CFU organism/ml. For the test samples, 2% of the preservative was added to 10 grams of the cream and mixed well. From this sample, 1 gram aliquots were placed into 10 ml sterile plastic culture tubes and 0.1 ml (100 microliters) of the test inoculum was added and vortexed until uniformly blended. The tubes were then placed into incubators under the following temperatures: 30° C. for *Aspergillus niger* and 37° C. for the remaining three microbes. All tubes were incubated for a total of 3 days. At the end of the incubation period, 9.0 ml of Butterfield Phosphate Buffered solution with neutralizer was added to the incubated cultured sample and vortexed until completely mixed. The samples were serially diluted and then plated in Trypticase soy agar (TSA). The plates were incubated at 37° C. temperature for 24-48 hours, and the counts were read. Placebo cream was tested similarly and used as the control. The following Table reflects the results of the testing.

TABLE 168

$Log_{10}$ Reduction from control growth

| Preservative | S. aureus | P. aeruginosa | Aspergillus niger |
|---|---|---|---|
| F | 6.8 | 4.65 | 5.0 |
| G | 7.3 | 5.8 | 5.1 |
| H | 5.5 | 5.0 | 3.0 |
| I | 6.5 | 5.0 | 4.9 |
| J | 5.5 | 4.5 | 3.0 |
| K | 5.8 | 4.8 | 4.0 |
| L | 6.0 | 5.2 | 3.8 |
| M | 6.8 | 5.5 | 5.0 |

Control growth for *S. aureus* and *P. aeruginosa* were $6.5×10^8$ and $1×10^8$ cfu/gm, respectively, and for *A. niger* was $6×10^4$-$1×10^5$. Based on these results, all of the above preservative compositions were effective.

Example 29

The following experiment was carried out to evaluate the synergistic effect of botanical extract, essential oil and fruit acids in a soap base.

Antibacterial efficacy of Grape fruit seed extract (GFSE) either alone or in combination with citric acid was determined by Method A (discussed below) and the results are shown in Table 169. Citric acid alone or a mixture of fruit acids such as lactic, citric, tartaric, glycolic and malic (Multi Fruit® BSC from Arch chemicals) were used.

Method A: 0.8 gms of plain Softsoap containing the following combinations (Table 169) was mixed with 0.1 ml of *S. aureus* culture ($10^8$ cfu/ml) and 0.1 ml bovine serum. After 30 seconds, 9 ml of drug neutralizing media (DNB) was added and mixed. Then, serial dilutions were made with DNB and plated on Trypticase Soy agar. Table 169 shows the results of the Log reduction from control counts.

TABLE 169

| Log₁₀ reduction from control counts | | |
|---|---|---|
| Group | (% w/w) | Log reduction |
| GSE | 0.3 | 0.87 |
| citric acid | 1.0 | 0.7 |
| GSE + citric | 0.3 + 1.0 | 3.28 |
| Lemon Grass oil (LG) | 0.2 | 0.04 |
| LG + Citric | 0.2 + 1.0 | 1.5 |
| GSE + LG + citric | 0.3 + 0.2 + 1.0 | 5.35 |
| Lactic acid | 0.2 | 0.5 |
| GSE + Lactic acid | 0.3 + 0.2 | 3.2 |

Example 30

The following example demonstrates preservative compositions containing low concentrations of essential oil/botanical extract.

The following preservative compositions were prepared and tested for their effectiveness. The preservative compositions contain the following: total Essential oil/botanical extracts concentration ranges from 1.0-20%, fruit acids ranging from 10-20%, alkanediols ranging from 30-80%, and alcohol ranging from 0-40%, phenoxy ethanol ranging from 0-40%, propylene glycol ranging from 0-80%, and vegetable oil ranging from 0-50%. Tables 170-179 provide the formulations of specific preservative compositions with essential oil and fruit acids.

TABLE 170

Preservative composition -1

| Ingredients | Stock (% w/w) | Products containing 1.75% stock (% w/w) |
|---|---|---|
| Lemongrass oil | 5.6 | 0.1 |
| Orange oil | 2.8 | 0.05 |
| Lactic acid | 11.4 | 0.2 |
| Octanediol | 40 | 0.7 |
| Phenoxyethanol | 40 | 0.7 |
| (pH of Stock solution 5.0) | | |

TABLE 171

Preservative composition -2

| Ingredients | Stock (% w/w) | Products containing 2.0% stock (% w/w) |
|---|---|---|
| Lemongrass oil | 3.75 | 0.075 |
| Orange oil | 1.25 | 0.025 |
| Lactic acid | 15 | 0.3 |
| Octanediol | 40 | 0.8 |
| Phenoxyethanol | 40 | 0.8 |
| (pH of Stock solution 5.0) | | |

TABLE 172

Preservative composition -3

| Ingredients | Stock (% w/w) | Products containing 2.0% stock (% w/w) |
|---|---|---|
| Lemongrass oil | 2.0 | 0.04 |
| Orange oil | 0.5 | 0.01 |
| Lactic acid | 10 | 0.2 |
| Octanediol | 60 | 1.2 |
| Phenoxyethanol | 27.5 | 0.55 |
| (pH of Stock solution 5.0) | | |

TABLE 173

Preservative composition -4

| Ingredients | Stock (% w/w) | Products containing 2.0% stock (% w/w) |
|---|---|---|
| Lemongrass oil | 5 | 0.1 |
| Orange oil | 5.0 | 0.1 |
| Lactic acid | 10 | 0.2 |
| Octanediol | 40 | 0.8 |
| Propylene glycol | 40.0 | 0.8 |
| (pH of Stock solution 5.0) | | |

TABLE 174

Preservative composition -5

| Ingredients | Stock (% w/w) | Products containing 2.0% stock (% w/w) |
|---|---|---|
| Lemongrass oil | 5 | 0.1 |
| Orange oil | 2.5 | 0.05 |
| Lactic acid | 10 | 0.2 |
| Octanediol | 50 | 1.0 |
| Propylene glycol | 32.5 | 0.65 |
| (pH of Stock solution 5.0) | | |

TABLE 175

Preservative composition - 6

| Ingredients | Stock (% w/w) | Products containing 2.0% stock (% w/w) |
|---|---|---|
| Lemongrass oil | 3.75 | 0.075 |
| Orange oil | 1.25 | 0.025 |
| Lactic acid | 10 | 0.2 |
| Octanediol | 50 | 1.0 |
| Propylene glycol | 35 | 0.7 |
| (pH of Stock solution 5.0) | | |

TABLE 176

Preservative composition - 7

| Ingredients | Stock (% w/w) | Products containing 2.0% stock (% w/w) |
|---|---|---|
| Lemongrass oil | 2.5 | 0.05 |
| Orange oil | 1.25 | 0.025 |
| Lactic acid | 10 | 0.2 |
| Octanediol | 50 | 1.0 |
| Propylene glycol | 36.25 | 0.725 |
| (pH of Stock solution 5.0) | | |

TABLE 177

Preservative composition - 7-A

| Ingredients | Stock (% w/w) | Products containing 2.5% stock (% w/w) |
|---|---|---|
| Lemongrass oil | 2.0 | 0.05 |
| Orange oil | 1.0 | 0.025 |
| Lactic acid | 8.0 | 0.2 |
| Octanediol | 40 | 1.0 |
| Propylene glycol | 49 | 1.225 |
| (pH of Stock solution 5.0) | | |

TABLE 178

Preservative composition - 7-B-L

| Ingredients | Stock (% w/w) | Products containing 2.5% stock (% w/w) |
|---|---|---|
| Lemongrass oil | 2.8 | 0.07 |
| Lactic acid | 8.0 | 0.2 |
| Octanediol | 40 | 1.0 |
| Propylene glycol | 49.2 | 1.23 |
| (pH of Stock solution 5.0) | | |

TABLE 179

Preservative composition - 7-B-M

| Ingredients | Stock (% w/w) | Products containing 2.5% stock (% w/w) |
|---|---|---|
| Lemongrass oil | 2.8 | 0.07 |
| Multifruit BSC | 8.0 | 0.2 |
| * Mixture of lactic, citric, tartaric, glycolic, malic acid extracted from plants (obtained from Arch Chemicals) | | |
| Octanediol | 40 | 1.0 |
| Propylene glycol | 49.2 | 1.23 |
| (pH of Stock solution 5.0) | | |

Tables 180-192 provide the formulations of specific preservative compositions containing grapefruit seed extract and grape seed extract.

TABLE 180

Preservative composition - G-8

| Ingredients | Stock (% w/w) | Products containing 2.0% stock (% w/w) |
|---|---|---|
| Grapefruit seed extract | 10 | 0.2 |
| Lactic acid | 10 | 0.2 |
| Octanediol | 50 | 1.0 |
| Propylene glycol | 30 | 0.6 |
| (pH of Stock solution 5.0) | | |

TABLE 181

Preservative composition - G-9

| Ingredients | Stock (% w/w) | Products containing 2.0% stock (% w/w) |
|---|---|---|
| Grapefruit seed extract | 10 | 0.2 |
| Lactic acid | 10 | 0.2 |
| Octanediol | 50 | 1.0 |

TABLE 181-continued

Preservative composition - G-9

| Ingredients | Stock (% w/w) | Products containing 2.0% stock (% w/w) |
|---|---|---|
| Safflower oil | 30 | 0.6 |
| (pH of Stock solution 5.0) | | |

TABLE 182

Preservative composition - G-10

| Ingredients | Stock (% w/w) | Products containing 2.0% stock (% w/w) |
|---|---|---|
| Lemongrass oil | 2.5 | 0.05 |
| Orange oil | 1.25 | 0.025 |
| Grape seed Extract | 10 | 0.2 |
| Lactic acid | 10 | 0.2 |
| Octanediol | 50 | 1.0 |
| Propylene glycol | 26.25 | 0.525 |
| (pH of Stock solution 5.0) | | |

TABLE 183

Preservative composition - G-10-A

| Ingredients | Stock (% w/w) | Products containing 2.5% stock (% w/w) |
|---|---|---|
| Lemongrass oil | 2.0 | 0.05 |
| Grape seed Extract | 8.0 | 0.2 |
| Lactic acid | 8.0 | 0.2 |
| Octanediol | 40 | 1.0 |
| Propylene glycol | 42.0 | 1.05 |
| (pH of Stock solution 5.0) | | |

TABLE 184

Preservative composition - G-10-M

| Ingredients | Stock (% w/w) | Products containing 2.0% stock (% w/w) |
|---|---|---|
| Lemongrass oil | 2.5 | 0.05 |
| Orange Oil | 1.25 | 0.025 |
| Grape seed Extract | 10 | 0.2 |
| Multifruit BSC | 10 | 0.2 |
| * Mixture of lactic, citric, tartaric, glycolic, malic acid extracted from plants(obtained from Arch Chemicals) | | |
| Octanediol | 50 | 1.0 |
| Propylene glycol | 26.25 | 0.525 |
| (pH of Stock solution 5.0) | | |

TABLE 185

Preservative composition - G-10-C

| Ingredients | Stock (% w/w) | Products containing 2.0% stock (% w/w) |
|---|---|---|
| Lemongrass oil | 2.5 | 0.05 |
| Orange Oil | 1.25 | 0.025 |
| Grape seed Extract | 10 | 0.2 |

TABLE 185-continued

Preservative composition - G-10-C

| Ingredients | Stock (% w/w) | Products containing 2.0% stock (% w/w) |
|---|---|---|
| Citric acid | 10 | 0.2 |
| Octanediol | 50 | 1.0 |
| Propylene glycol | 26.25 | 0.525 |
| (pH of Stock solution 5.0) | | |

TABLE 186

Preservative composition - G-11

| Ingredients | Stock (% w/w) | Products containing 2.0% stock (% w/w) |
|---|---|---|
| Lemongrass oil | 3.75 | 0.075 |
| Orange Oil | 1.25 | 0.025 |
| Grape seed Extract | 10 | 0.2 |
| Lactic Acid | 10 | 0.2 |
| Octanediol | 50 | 1.0 |
| Propylene glycol | 25 | 0.5 |
| (pH of Stock solution 5.0) | | |

TABLE 187

Preservative composition - G-12

| Ingredients | Stock (% w/w) | Products containing 2.0% stock (% w/w) |
|---|---|---|
| Grape seed Extract | 15 | 0.3 |
| Lactic acid | 10 | 0.2 |
| Octanediol | 50 | 1.0 |
| Propylene glycol | 25 | 0.5 |
| (pH of Stock solution 5.0) | | |

TABLE 188

Preservative composition - G-13

| Ingredients | Stock (% w/w) | Products containing 2.5% stock (% w/w) |
|---|---|---|
| Lemongrass oil | 12 | 0.3 |
| Orange Oil | 4 | 0.1 |
| Grape seed Extract | 8.0 | 0.2 |
| Lactic Acid | 8.0 | 0.2 |
| Octanediol | 40 | 1.0 |
| Propylene glycol | 28 | 0.7 |
| (pH of Stock solution 5.0) | | |

TABLE 189

Preservative composition - G-14

| Ingredients | Stock (% w/w) | Products containing 2.5% stock (% w/w) |
|---|---|---|
| Lemongrass oil | 0.8 | 0.02 |
| Orange Oil | 0.4 | 0.01 |
| Grape seed Extract | 12 | 0.3 |
| Lactic Acid | 8.0 | 0.2 |
| Octanediol | 40 | 1.0 |
| Propylene glycol | 38.8 | 0.97 |
| (pH of Stock solution 5.0) | | |

TABLE 190

Preservative composition - G-15

| Ingredients | Stock (% w/w) | Products containing 2.5% stock (% w/w) |
|---|---|---|
| Lemongrass oil | 0.8 | 0.075 |
| Grape seed Extract | 12 | 0.2 |
| Lactic acid | 8.0 | 0.2 |
| Octanediol | 40 | 1.0 |
| Propylene glycol | 41.2 | 1.03 |
| (pH of Stock solution 5.0) | | |

TABLE 191

Preservative composition - G-16

| Ingredients | Stock (% w/w) | Products containing 2.5% stock (% w/w) |
|---|---|---|
| Lemongrass oil | 2.8 | 0.07 |
| Grape seed Extract | 8.0 | 0.2 |
| Lactic Acid | 8.0 | 0.2 |
| Octanediol | 28 | 0.7 |
| Propylene glycol | 53.2 | 1.33 |
| (pH of Stock solution 5.0) | | |

TABLE 192

Preservative composition - G-17

| Ingredients | Stock (% w/w) | Products containing 2.5% stock (% w/w) |
|---|---|---|
| Lemongrass oil | 2.8 | 0.07 |
| Grape seed Extract | 8 | 0.2 |
| Lactic Acid | 8 | 0.2 |
| Octanediol | 40 | 1.0 |
| Propylene glycol | 41.2 | 1.03 |
| (pH of Stock solution 5.0) | | |

Tables 193-198 provide the formulations of specific preservative compositions containing essential oils/botanical extracts, fruit acids and alkanediol without solvents. All of the compositions ending in "L" are noted as the L series, which contain lactic acid. All of the compositions ending in "M" are noted as the M series, which contain Multifruit®BSC.

Multifruit®BSC contains a mixture of lactic, citric, tartaric, glycolic, and malic acid extracted from plants (obtained from Arch Chemicals). The pH of all the preservative compositions in Tables 193-198 were adjusted to 5.0 with 10 N. NaoH (30-70 ul/ml were required).

TABLE 193

Preservative composition - 6-L

| Ingredients | Stock (% w/w) | Cream containing 1.3% stock |
|---|---|---|
| Lemongrass oil | 5.78 | 0.075 |
| Orange oil | 1.92 | 0.025 |
| Lactic Acid | 15.4 | 0.2 |
| Octanediol | 76.9 | 1.0 |

TABLE 194

Preservative composition - 6-M

| Ingredients | Stock (% w/w) | Cream containing 1.3% stock |
|---|---|---|
| Lemongrass oil | 5.78 | 0.075 |
| Orange oil | 1.92 | 0.025 |
| Multifruit extract | 15.4 | 0.2 |
| Octanediol | 76.9 | 1.0 |

TABLE 195

Preservative composition - 10-G-L

| Ingredients | Stock (% w/w) | Cream containing 1.5% stock |
|---|---|---|
| Lemongrass oil | 3.3 | 0.05 |
| Orange oil | 1.6 | 0.025 |
| Grapefruit seed extract | 15.0 | 0.225 |
| Lactic Acid | 13.3 | 0.2 |
| Octanediol | 66.8 | 1.0 |

TABLE 196

Preservative composition - 10-G-M

| Ingredients | Stock (% w/w) | Cream containing 1.5% stock |
|---|---|---|
| Lemongrass oil | 3.3 | 0.05 |
| Orange oil | 1.6 | 0.025 |
| Grapefruit seed extract | 15 | 0.225 |
| Multifruit BSC | 13.3 | 0.2 |
| Mixture of lactic, citric, tartaric, glycolic, malic acid extracted from plants (obtained from Arch Chemicals) | | |
| Octanediol | 66.8 | 1.0 |

TABLE 197

Preservative composition - 11-G-L

| Ingredients | Stock (% w/w) | Cream containing 1.5% stock |
|---|---|---|
| Lemongrass oil | 5.0 | 0.075 |
| Orange oil | 1.7 | 0.025 |
| Grapefruit seed extract | 13.3 | 0.2 |
| Lactic Acid | 13.3 | 0.2 |
| Octanediol | 66.7 | 1.0 |

TABLE 198

Preservative composition - 11-G-M

| Ingredients | Stock (% w/w) | Cream containing 1.5% stock |
|---|---|---|
| Lemongrass oil | 5.0 | 0.075 |
| Orange oil | 1.7 | 0.025 |
| Grapefruit seed extract | 13.3 | 0.2 |
| Multifruit BSC | 13.3 | 0.2 |
| Mixture of lactic, citric, tartaric, glycolic, malic acid extracted from plants (obtained from Arch Chemicals) | | |
| Octanediol | 66.7 | 1.0 |

Example 31

The following example evaluates preservative activity of the formulations noted in preceding examples containing low concentrations of essential oils and botanical extract.

Test Method B. Test inoculums were prepared as follows.
Bacteria: $10^8$ CFU organism/ml.
Yeast (*C. albicans*): $10^7$ CFU organism/ml.
Fungi (*Aspergillus niger*): $10^6$ cfu organism/ml.

For the test samples, preservative was added to 10 grams of the cream at a concentration Of 1.5-2%. and mixed well. From this sample, 1 gram aliquots were placed into 10 ml sterile plastic culture tubes and 0.1 ml (100 micro liters) of the test inoculums was added and vortexed until uniformly blended. The tubes were then placed into incubators under the following temperatures: 30° C. for *Aspergillus niger* and 37° C. for the remaining three microbes. All tubes were incubated for a total of 1-2 days. At the end of the incubation period, 9.0 ml of Butterfield Phosphate Buffered solution with neutralizer was added to the incubated cultured sample and vortexed until completely mixed. The samples were serially diluted and then plated in Trypticase soy agar (TSA). The plates were incubated at 37° C. temperature for 24-48 hours, and the counts were read. Placebo cream was tested similarly and used as the control. Table 199 shows the results of the testing. In order for effective preservation, the log reduction should be 3 or more within 72 hours.

TABLE 199

$Log_{10}$ Reduction from control growth

| Preservative | S. aureus | P. aeruginosa | Aspergillus niger |
|---|---|---|---|
| 1 | 7.5 | 7.5 | 4.0 |
| 2 | 7.5 | 7.5 | 4.2 |
| 3 | 7.5 | 7.8 | 4.6 |
| 5 | 7.3 | 7.8 | 3.3 |
| 6 | 7.5 | 7.8 | 2.8 |
| 7 | 7.5 | 7.8 | 2.5 |
| 7A | 7.5 | 7.8 | 2.8 |

The Control had 7.5-7.8 $log_{10}$ colony counts for bacteria and 4.6 for *A. niger*. The results of *S. aureus* and *P. aeruginosa* are after 24 hours incubation and that of *Aspergillus Niger* is after 2 days 2% preservative added to the cream.

Conclusion: All the preservatives were effective. However the groups containing phenoxyethanol were more effective in the case of *A. niger*.

TABLE 200

$Log_{10}$ Reduction from control (cream with no preservative) growth

| Preservative | S. aureus | P. aeruginosa | Aspergillus niger |
|---|---|---|---|
| G-8 | 7.5 | 7.8 | 2.7 |
| G-10 | 7.3 | 7.8 | 3.4 |
| G_10M | 7.3 | 7.3 | 3.6 |
| G-10C | 7.5 | 7.8 | 3.5 |
| G-11 | 7.5 | 7.8 | 4.5 |
| G-12 | 7.5 | 7.8 | 2.8 |

The results of *S. aureus* and *P. aeruginosa* are after 24 hours incubation and that of *Aspergillus .Niger* is after 2 days. 2% preservative added to the cream.

Conclusion: Groups containing Grape fruit seed extract and essential oils are more effective than grapefruit seed extract in the case of *A. niger*.

TABLE 201

| Preservative | Log₁₀ Reduction from control growth | | |
|---|---|---|---|
| | S. aureus | P. aeruginosa | Aspergillus niger |
| 6-L | 7.5 | 7.8 | 2..0 |
| 6-M | 7.3 | 7.8 | 2.2 |
| 10-G-L | 6.3 | 7.8 | 2.2 |
| 10-G-M | 7.5 | 7.8 | 2.4 |
| 11-G-L | 7.5 | 7.8 | 2.2 |
| 11-G-M | 7.5 | 7.8 | 2.4 |

The results of *S. aureus* and *P. aeruginosa* are after 24 hours incubation and that of *Aspergillus Niger* is after 2-3 days Figures in Parenthesis are the log reduction after 3 days incubation. 1.5% preservative added to the cream Conclusion: Multifruit groups are more effective against *A. Niger*. However, all these groups which do not have solvents are highly effective against bacteria, but slightly less effective against *A. Niger*. It appears that the solvents releases sufficient amount of oil/extracts to inactivate *A. Niger*.

Example 32

The following example evaluates the synergistic activity of essential oils and plant extracts with citric acid against *S. aureus*.

TABLE 202

| Compounds % | Log₁₀ Reduction |
|---|---|
| 1 Citric acid | 0.7 |
| 0.2 Grape fruit seed extract | 0.64 |
| 0.2 Grape fruit seed extract + 1 Citric acid | 5.91 |
| 0.5 Lemongrass oil + 1 Citric acid | 5.66 |
| 0.3 Lemongrass oil + 0.2 Grape fruit seed extract + 1 Citric acid | 7.31 |
| 0.25 Manuka oil | 0.94 |
| 0.25 Manuka oil + 1 Citric acid | 5.85 |
| 0.25 Rosemary oil | 0.48 |
| 0.25 Rose Mary oil + 1 Citric acid | 2.0 |
| 0.25 Pomegranate oil | 0.49 |
| 0.25 Pomegranate oil + 1 Citric acid | 7.31 |
| 0.25 Pomegranate extract | 0.40 |
| 0.25 Pomegranate extract + 1 Citric acid | 6.21 |
| 0.25 *Calendula* oil | 0.50 |
| 0.25 *Calendula* oil + 1 Citric acid | 3.07 |

Log₁₀ reduction from control bacterial counts that range from 1×10⁷ to 5×10⁷.

Conclusion: All the essential oils or extracts tested showed synergistic activity with citric acid but Pomegranate oil has more synergistic activity compared to others. Rosemary showed least synergism with citric acid. Lemongrass and grapefruit seed extract together with citric acid had more synergistic activity than lemongrass or grapefruit seed extract alone.

Example 33

The following example demonstrates the use of glycerine as a solvent in preservative compositions containing low concentrations of essential oil/botanical extract.

The following preservative compositions were prepared and tested for their effectiveness.

TABLE 203

| Preservative composition - G-17-G | | |
|---|---|---|
| Ingredients | Stock (% w/w) | Cream containing 2.5% stock |
| Lemongrass oil | 2.8 | 0.07 |
| Grapefruit seed extract | 8.0 | 0.2 |
| Lactic acid | 8.0 | 0.2 |
| Octanediol | 40 | 1.0 |
| Glycerine | 41.2 | 1.03 |

The pH of the stock solution is 5.0. Glycerine is a good alternative solvent for those individuals who have skin sensitivity to propylene glycol, which has been shown to absorb through the skin, or phenoxyethanol, which may be irritating to certain individuals.

The formulation was tested against different organisms for its antimicrobial effects. The data are shown in the following Table.

TABLE 204

| Organism | Log₁₀ reduction from control bacterial counts |
|---|---|
| A. niger | 4.93 |
| S. aureus | 7.3 |
| P. aureginosa | 7.8 |

The data demonstrate that the preservative formulation containing glycerine as the solvent is also an effective antimicrobial preservative composition.

Example 34

The following example demonstrates the use of low concentrations of solvents in preservative formulations. The following preservative compositions were prepared.

TABLE 205

| Preservative composition - G-18-G | | |
|---|---|---|
| Ingredients | Composition of Stock Solution (% w/w) | Cream containing 1.5% stock |
| Lemongrass oil | 4.67 | 0.07 |
| Grapefruit seed extract | 13.33 | 0.2 |
| Lactic acid | 13.33 | 0.2 |
| Octanediol | 46.67 | 0.7 |
| Glycerine | 22.0 | 0.33 |
| (pH of Stock solution 5.0) | | |

TABLE 206

| Preservative composition - G-18 | | |
|---|---|---|
| Ingredients | Composition of Stock Solution (% w/w) | Cream containing 1.5% stock |
| Lemongrass oil | 4.67 | 0.07 |
| Grapefruit seed extract | 13.33 | 0.2 |
| Lactic acid | 13.33 | 0.2 |
| Octanediol | 46.67 | 0.7 |
| Propylene glycol | 22.0 | 0.33 |
| (pH of Stock solution 5.0) | | |

TABLE 207

Preservative composition - G-19-G

| Ingredients | Composition of Stock Solution (% w/w) | Cream containing 1.5% stock |
|---|---|---|
| Lemongrass oil | 4.67 | 0.07 |
| Grapefruit seed extract | 13.33 | 0.2 |
| Lactic acid | 13.33 | 0.2 |
| Octanediol | 46.67 | 0.5 |
| Glycerine | 22.0 | 0.53 |

(pH of Stock solution 5.0)

TABLE 208

Preservative composition - G-19

| Ingredients | Composition of Stock Solution (% w/w) | Cream containing 1.5% stock |
|---|---|---|
| Lemongrass oil | 4.67 | 0.07 |
| Grapefruit seed extract | 13.33 | 0.2 |
| Lactic acid | 13.33 | 0.2 |
| Octanediol | 46.67 | 0.5 |
| Propylene glycol | 22.0 | 0.53 |

(pH of Stock solution 5.0)

TABLE 209

Preservative composition V-1

| Ingredients | Composition of Stock Solution (% w/w) | Cream containing 2.0% stock |
|---|---|---|
| Lemongrass oil | 5.0 | 0.1 |
| Grapefruit seed extract | 10.0 | 0.2 |
| Lactic acid | 10.0 | 0.2 |
| Octanediol | 25.0 | 0.5 |
| Glycerine | 50.0 | 1.0 |

TABLE 210

Preservative composition V-3

| Ingredients | Composition of Stock Solution (% w/w) | Cream containing 2.0% stock |
|---|---|---|
| Lemongrass oil | 5.0 | 0.1 |
| Grapefruit seed extract | 5.0 | 0.1 |
| Lactic acid | 10.0 | 0.2 |
| Octanediol | 25.0 | 0.5 |
| Glycerine | 55.0 | 1.1 |

TABLE 211

Preservative composition V-8

| Ingredients | Composition of Stock Solution (% w/w) | Cream containing 1.5% stock |
|---|---|---|
| Lemongrass oil | 6.67 | 0.1 |
| Grapefruit seed extract | 6.67 | 0.1 |
| Lactic acid | 13.33 | 0.2 |
| Octanediol | 20.0 | 0.3 |
| Glycerine | 33.33 | 0.5 |
| Zemea | 20.0 | 0.3 |

Example 35

The following experiment was carried out to evaluate the synergistic effect of botanical extract, essential oil and fruit acids in a soap base.

Method A: 0.8 gms of plain Softsoap containing the following combination was mixed with 0.1 ml of *S. aureus* culture ($10^8$ cfu/ml) and 0.1 ml bovine serum. After 30 seconds, 9 ml of drug neutralizing media (DNB) was added and mixed. Then, serial dilutions were made with DNB and plated on Trypticase Soy agar.

The stock solution of the soap compositions (LG-6 soaps) is summarized in the following Table. 10-20% of the stock solutions maybe used to prepare specific soap formulations.

TABLE 212

Stock compositions for LG-6 soaps

| Ingredient | % (w/w) |
|---|---|
| Lemongrass oil | 4.29 |
| Grapefruit seed extract | 2.85 |
| Orange oil | 1.42 |
| Alkanediols | 7.14 |
| Fruit Acids | 14.29 |
| Alcohol | 70.0 |

The following soap formulations were prepared.

TABLE 213

LG-6-O

| Ingredient | % (w/w) |
|---|---|
| Lemongrass oil | 0.3 |
| Grapefruit seed extract | 0.2 |
| Orange oil | 0.1 |
| Octanediol | 0.5 |
| SDA 3C | 4.9 |
| Citric Acid | 1.0 |
| Softsoap Base (Colgate Palmolive) | 93.0 |

TABLE 214

LG-6-S

| Ingredient | % (w/w) |
|---|---|
| Lemongrass oil | 0.3 |
| Grapefruit seed extract | 0.2 |
| Orange oil | 0.1 |
| Symclariol | 0.5 |
| Phenoxyethanol | 1.0 |
| SDA 3C | 3.9 |
| Citric Acid | 1.0 |
| Softsoap Base (Colgate Palmolive) | 93.0 |

TABLE 215

LG-6-O-TC

| Ingredient | % (w/w) |
|---|---|
| Lemongrass oil | 0.3 |
| Grapefruit seed extract | 0.2 |
| Orange oil | 0.1 |
| Octanediol | 0.5 |
| SDA 3C | 4.75 |
| Citric Acid | 1.0 |

TABLE 215-continued

LG-6-O-TC

| Ingredient | % (w/w) |
| --- | --- |
| Triclosan | 0.15 |
| Softsoap Base (Colgate Palmolive) | 93.0 |

The stock solution of alternative soap compositions (LG-19 Soaps) is summarized in the following Table. 10%-20% of the stock solutions may be used to prepare specific soap formulations.

TABLE 216

Stock compositions for LG-19 soaps

| Ingredient | % (w/w) |
| --- | --- |
| Lemongrass oil | 1.56 |
| Grapefruit seed extract | 1.04 |
| Orange oil | 0.52 |
| Alkanediols | 2.60 |
| Fruit Acids | 5.21 |
| Alcohol | 89.06 |

The following soap formulations were prepared.

TABLE 217

LG-19-O

| Ingredient | % (w/w) |
| --- | --- |
| Water | 63.1 |
| Methocil (40-101) | 0.2 |
| U-care Jr | 0.3 |
| Pluronic F-87 | 1.0 |
| Montalene C-40 | 2.0 |
| Incromine oxide L | 8.0 |
| Crosultane C-50 | 3.0 |
| Glycerine | 2.0 |
| Polyoxyl SR-N-60K | 0.2 |
| SDA 40 B | 17.1 |
| Citric acid | 1.0 |
| Lemongrass oil | 0.3 |
| Orange oil | 0.1 |
| Grapefruit seed extract | 0.2 |
| Phenoxy ethanol | 1.0 |
| Octanediol | 0.5 |

TABLE 218

LG-19-S

| Ingredient | % (w/w) |
| --- | --- |
| Water | 63.1 |
| Methocil (40-101) | 0.2 |
| U-care Jr | 0.3 |
| Pluronic F-87 | 1.0 |
| Montalene C-40 | 2.0 |
| Incromine oxide L | 8.0 |
| Crosultane C-50 | 3.0 |
| Glycerine | 2.0 |
| Polyoxyl SR-N-60K | 0.2 |
| SDA 40 B | 17.1 |
| Citric acid | 1.0 |
| Lemongrass oil | 0.3 |
| Orange oil | 0.1 |
| Grapefruit seed extract | 0.2 |
| Phenoxy ethanol | 1.0 |
| Symclariol | 0.5 |

The following table contains the test data of the LG-6-O composition.

TABLE 219

Effect of LG-6-O against S. aureus

| Compounds | $Log_{10}$ reduction from control* |
| --- | --- |
| Dial ® Soap-TC (0.15% TC) | 0.33 |
| LOG 1 | 6.01 |

*Log reduction from control bacterial counts ranged from $1\text{-}4 \times 10^7$.

Various patent and non-patent publications are cited herein, the contents of which are hereby incorporated by reference in their entireties.

We claim:

1. A hand soap, hand sanitizer or hand cream composition that achieves more than about 4 Log10 reduction from control bacterial counts within 30 seconds of contact, comprising:
   a. 0.01 to 0.7% w/w lemongrass oil;
   b. 0.01 to 0.5% w/w orange oil;
   c. 0.1 to 0.5% w/w grapefruit seed extract;
   d. 0.125 to 1% w/w citric acid;
   e. 0.3 to 10% w/w of a combination of octanediol and 1,3 propanediol;
   f. one or more additional ingredients selected from the group consisting of: cationic surfactants, nonionic surfactants, amphoteric surfactants, cellulose polymers, cetearyl Alcohol, behentrimonium methosulfate, stearyl alcohol, glycerin, almond oil, jojoba oil, avocado oil, silicone polymers, silicone oil and combinations thereof; and
   g. 0.5 to 20% w/w of an alcohol selected from the group consisting of: ethanol, isopropanol, phenoxyethanol and combinations thereof.

2. The hand soap, hand sanitizer or hand cream composition of claim 1, wherein the one or more additional ingredients include 0.5 to 10% w/w nonionic surfactant selected from the group consisting of: poly(ethylene oxide), poly(propylene oxide), poly(ethylene oxide) block copolymer surfactant, a poloxamer, cocoamido propylamine oxide and combinations thereof.

3. The hand soap, hand sanitizer or hand cream composition of claim 1, wherein the one or more additional ingredients include 0.05 to 2% w/w cationic surfactant selected from the group consisting of: benzalkonium chloride, guar hydroxypropyltrimonium chloride and combinations thereof.

4. The hand soap, hand sanitizer or hand cream composition of claim 1, wherein the one or more additional ingredients include cellulose polymer selected from the group consisting of: cationic hydroxyethyl cellulose, hydroxypropyl methylcellulose and combinations thereof.

5. The hand soap, hand sanitizer or hand cream composition of claim 1, further comprising:
   i. 1 to 5% w/w aloe; and
   j. 5 to 5% w/w calendula oil or extract.

6. A surface disinfectant composition that achieves more than about 4 Log10 reduction from control bacterial counts within 30 seconds of contact, comprising:
   a. 0.5 to 3% w/w lemongrass oil;
   b. 0.1 to 0.5% w/w orange oil;
   c. 0.1 to 0.5% w/w grapefruit seed extract;
   d. 0.125 to 2% w/w citric acid;
   e. 0.3 to 10% w/w of a combination of octanediol and 1,3 propanediol;

f. 0.5 and 10% w/w surfactant selected from the group consisting of nonionic surfactants, cationic surfactants, amphoteric surfactants and combinations thereof;
g. 5 to 51% w/w alcohol selected from the group consisting of ethanol, isopropanol and combinations thereof; and
h. water.

7. A surface disinfectant composition that achieves more than about 4 Log10 reduction from control bacterial counts within 5 minutes of contact, comprising:
a. 0.01 to 0.5% w/w lemongrass oil;
b. 0.01 to 0.5% w/w orange oil;
c. 0.01 to 0.5% w/w grapefruit seed extract;
d. 0.2 to 1% w/w citric acid;
e. 0.3 to 1% w/w of a combination of octanediol and 1,3-propanediol;
f. 0.5 to 2% w/w surfactant selected from selected from nonionic surfactants, cationic surfactants and combinations thereof;
g. 0.5 to 15% w/w alcohol selected from the group consisting of ethanol, isopropanol and combinations thereof; and
i. water.

8. A hand soap composition of claim 1, comprising:
a. 0.01 to 0.5% w/w lemongrass oil;
b. 0.01 to 0.5% w/w orange oil;
c. 0.1 to 0.5% w/w grapefruit seed extract;
d. 0.125 to 1% w/w citric acid;
e. 1 to 10% w/w of a combination of octanediol and 1,3 propanediol;
f. 5 to 10% w/w of one or more nonionic surfactants;
g. 0.05 to 2% w/w of one or more cationic surfactants;
h. one or more cellulose polymers selected from the group consisting of: cationic hydroxyethyl cellulose, hydroxypropyl methyl cellulose and combinations thereof;
i. one or more emollients selected from the group consisting of glycerin, aloe, and calendula extract;
j. 0.1 to 1% w/w silicone polymer; and
k. 0.5 to 20% w/w of an alcohol selected from the group consisting of: ethanol, isopropanol, phenoxyethanol and combinations thereof.

9. A hand sanitizer composition of claim 1, further comprising:
a. 0.1 to 0.2% w/w lemongrass oil;
b. 0.01 to 0.5% w/w orange oil;
c. 0.1 to 0.2% w/w grapefruit seed extract;
d. 0.125 to 1% w/w citric acid;
e. 1 to 10% w/w of a combination of octanediol and 1,3 propanediol;
f. 0.2 to 0.5% w/w hydroxypropyl methyl cellulose;
g. one or more emollients selected from the group consisting of glycerin, aloe gel, and calendula extract;
h. 0.05 to 2% cocoamido propyl betaine;
i. 0.1 to 1% w/w silicone polymer; and
j. 0.5 to 20% w/w of an alcohol selected from the group consisting of: ethanol, isopropanol, phenoxyethanol and combinations thereof.

10. A composition that achieves more than about 4 Log10 reduction from control bacterial counts within 5 minutes of contact, the composition comprising:
a. 0.1 to 0.7% w/w orange oil;
b. 0.2 to 0.5% w/w lemongrass oil;
c. 0.2 to 0.225% w/w grapefruit seed extract;
d. 0.25 to 2% citric acid;
e. 0.3 to 10% of a combination of octanediol and 1,3-propanediol; and
f. 0.5 to 20% w/w of an alcohol selected from the group consisting of: ethanol, isopropanol, phenoxyethanol and combinations thereof.

11. The composition of claim 10, in the form of a soap, further comprising:
g. 1.5 to 11% of one or more surfactants; and
h. 1.5 to 3% of a foaming agent comprising a coconut oil based surfactant.

12. The composition of claim 10, in the form of a surface cleaner, further comprising:
g. 1.5 to 2.1% of one or more nonionic surfactants; and
h. 0.2 to 0.5 cinnamon oil or pine oil.

13. The composition of claim 10, in the form of a teat dip for treating mastitis, further comprising:
g. 5 to 15% glycerin;
h. 0.1 to 5% of one or more anti-irritants;
i. 0.2 to 1% of a vehicle containing gelling agent; and
j. 50 to 80% water.

14. A cleansing wipe, wound covering, wound care item or steri-strip having a surface comprising the composition of claim 10.

15. A wipe having a surface comprising the surface cleaner composition of claim 12.

* * * * *